United States Patent
Kim

(10) Patent No.: US 8,075,595 B2
(45) Date of Patent: Dec. 13, 2011

(54) SYSTEMS AND METHODS FOR POSTERIOR DYNAMIC STABILIZATION OF THE SPINE

(75) Inventor: Daniel H. Kim, Mountain View, CA (US)

(73) Assignee: The Board of Trustees of The Leland Stanford Junior University, Palo Alto, CA (US)

( * ) Notice: Subject to any disclaimer, the term of this patent is extended or adjusted under 35 U.S.C. 154(b) by 875 days.

(21) Appl. No.: 11/006,495

(22) Filed: Dec. 6, 2004

(65) Prior Publication Data

US 2006/0084984 A1    Apr. 20, 2006

Related U.S. Application Data

(63) Continuation-in-part of application No. 10/970,366, filed on Oct. 20, 2004.

(51) Int. Cl.
*A61B 17/70* (2006.01)

(52) U.S. Cl. .......... 606/257; 606/279; 606/264

(58) Field of Classification Search ............ 606/246, 606/253, 256, 257, 258, 259, 263, 279, 105
See application file for complete search history.

(56) References Cited

U.S. PATENT DOCUMENTS

| | | | |
|---|---|---|---|
| 602,580 A | 4/1898 | Haskins et al. |
| 802,844 A | 10/1905 | Covell et al. |
| 2,051,248 A | 8/1936 | Dunn |
| 3,807,394 A | 4/1974 | Attenborough |
| 4,611,582 A | 9/1986 | Duff |
| 4,743,260 A | 5/1988 | Burton |
| 5,015,247 A | 5/1991 | Michelson |
| 5,092,866 A | 3/1992 | Breard et al. |
| 5,129,388 A | 7/1992 | Vignaud et al. |
| 5,171,279 A | 12/1992 | Mathews |
| 5,180,393 A | 1/1993 | Commarmond |
| 5,282,863 A | 2/1994 | Burton |
| 5,368,594 A | 11/1994 | Martin et al. |
| 5,375,823 A | 12/1994 | Navas |
| 5,387,212 A | 2/1995 | Yuan et al. |
| 5,415,661 A | 5/1995 | Holmes |
| 5,437,669 A | 8/1995 | Yuan et al. |
| 5,437,672 A | 8/1995 | Alleyne |

(Continued)

FOREIGN PATENT DOCUMENTS

EP    767636    1/1999

(Continued)

OTHER PUBLICATIONS

Co-pending U.S. Appl. No. 11/033,452.

(Continued)

*Primary Examiner* — Thomas C. Barrett
*Assistant Examiner* — Andrew Yang
(74) *Attorney, Agent, or Firm* — Meyertons, Hood, Kivlin, Kowert & Goetzel, P.C.; Eric B. Meyertons

(57) ABSTRACT

Systems and devices for dynamically stabilizing the spine are provided. The systems include a superior component for attachment to a superior vertebra of a spinal motion segment and an inferior component for attachment to an inferior vertebral of a spinal motion segment. The interconnection between the two components enables the spinal motion segment to move in a manner that mimics the natural motion of the spinal motion segment. Methods are also provided for stabilizing the spine and for implanting the subject systems.

20 Claims, 68 Drawing Sheets

U.S. PATENT DOCUMENTS

| | | | |
|---|---|---|---|
| 5,443,467 A | 8/1995 | Biedermann et al. | |
| 5,474,555 A | 12/1995 | Puno et al. | |
| 5,480,401 A | 1/1996 | Navas | |
| 5,484,437 A | 1/1996 | Michelson | |
| 5,489,308 A | 2/1996 | Kuslich et al. | |
| 5,522,843 A | 6/1996 | Zang | |
| 5,527,312 A | 6/1996 | Ray | |
| 5,540,688 A | 7/1996 | Navas | |
| 5,571,191 A | 11/1996 | Fitz | |
| 5,609,636 A | 3/1997 | Kohrs et al. | |
| 5,616,142 A | 4/1997 | Yuan et al. | |
| 5,645,599 A | 7/1997 | Samani | |
| 5,658,337 A | 8/1997 | Kohrs et al. | |
| 5,672,175 A * | 9/1997 | Martin | 606/86 A |
| 5,720,751 A | 2/1998 | Jackson | |
| 5,738,586 A | 4/1998 | Arriaga | |
| 5,741,253 A | 4/1998 | Michelson | |
| 5,776,135 A | 7/1998 | Errico et al. | |
| RE36,211 E | 5/1999 | Nonomura | |
| 5,964,761 A | 10/1999 | Kambin | |
| 6,014,588 A | 1/2000 | Fitz | |
| 6,033,406 A | 3/2000 | Mathews | |
| RE36,758 E | 6/2000 | Fitz | |
| 6,080,155 A | 6/2000 | Michelson | |
| 6,080,157 A | 6/2000 | Cathro et al. | |
| 6,083,224 A | 7/2000 | Gertzbein et al. | |
| 6,096,038 A | 8/2000 | Michelson | |
| 6,132,464 A | 10/2000 | Martin | |
| 6,200,322 B1 | 3/2001 | Branch et al. | |
| 6,241,730 B1 | 6/2001 | Alby | |
| 6,264,656 B1 | 7/2001 | Michelson | |
| 6,267,764 B1 | 7/2001 | Elberg | |
| 6,267,765 B1 | 7/2001 | Taylor et al. | |
| 6,270,498 B1 | 8/2001 | Michelson | |
| 6,273,914 B1 | 8/2001 | Papas | |
| 6,287,764 B1 | 9/2001 | Hildebrand et al. | |
| 6,419,703 B1 | 7/2002 | Fallin et al. | |
| 6,485,518 B1 | 11/2002 | Cornwall et al. | |
| 6,530,929 B1 | 3/2003 | Justis et al. | |
| 6,540,747 B1 | 4/2003 | Marino | |
| 6,547,795 B2 | 4/2003 | Schneiderman | |
| 6,558,390 B2 | 5/2003 | Cragg | |
| 6,562,038 B1 | 5/2003 | Morrison | |
| 6,562,046 B2 | 5/2003 | Sasso | |
| 6,565,605 B2 | 5/2003 | Goble et al. | |
| 6,579,319 B2 | 6/2003 | Goble et al. | |
| 6,610,091 B1 | 8/2003 | Reiley | |
| 6,626,904 B1 | 9/2003 | Jammet et al. | |
| 6,626,905 B1 | 9/2003 | Schmiel et al. | |
| 6,626,944 B1 | 9/2003 | Taylor et al. | |
| 6,645,248 B2 | 11/2003 | Casutt | |
| 6,669,697 B1 | 12/2003 | Pisharodi | |
| 6,669,729 B2 | 12/2003 | Chin | |
| 6,695,842 B2 | 2/2004 | Zucherman et al. | |
| 6,716,245 B2 | 4/2004 | Pasquet et al. | |
| 6,749,613 B1 | 6/2004 | Conchy et al. | |
| 6,749,614 B2 | 6/2004 | Teitelbaum et al. | |
| 6,761,720 B1 | 7/2004 | Senegas et al. | |
| 6,783,527 B2 | 8/2004 | Drewry et al. | |
| 6,802,844 B2 | 10/2004 | Ferree | |
| 6,802,845 B2 | 10/2004 | Shirado et al. | |
| 6,805,697 B1 | 10/2004 | Helm et al. | |
| 6,811,567 B2 | 11/2004 | Reiley | |
| 6,821,277 B2 | 11/2004 | Teitelbaum | |
| 6,835,205 B2 | 12/2004 | Atkinson et al. | |
| 6,835,207 B2 | 12/2004 | Zacouto et al. | |
| 6,875,212 B2 | 4/2005 | Shaolian et al. | |
| 6,899,716 B2 | 5/2005 | Cragg | |
| 6,902,580 B2 | 6/2005 | Fallin et al. | |
| 6,949,123 B2 | 9/2005 | Reiley | |
| 6,966,910 B2 | 11/2005 | Ritland | |
| 6,966,930 B2 | 11/2005 | Arnin et al. | |
| 6,974,478 B2 * | 12/2005 | Reiley et al. | 623/17.11 |
| 6,986,771 B2 | 1/2006 | Paul et al. | |
| 6,989,011 B2 | 1/2006 | Paul et al. | |
| 6,991,632 B2 | 1/2006 | Ritland | |
| 7,011,660 B2 | 3/2006 | Sherman et al. | |
| 7,011,685 B2 | 3/2006 | Arnin et al. | |
| 7,029,475 B2 | 4/2006 | Panjabi | |
| 7,051,451 B2 | 5/2006 | Augostino et al. | |
| 7,052,497 B2 | 5/2006 | Sherman et al. | |
| 7,056,321 B2 | 6/2006 | Pagliuca et al. | |
| 7,060,068 B2 | 6/2006 | Tromanhauser et al. | |
| 7,066,957 B2 | 6/2006 | Graf | |
| 7,070,598 B2 | 7/2006 | Lim et al. | |
| 7,074,238 B2 | 7/2006 | Stinson et al. | |
| 7,079,883 B2 | 7/2006 | Marino et al. | |
| 7,083,621 B2 | 8/2006 | Shaolian et al. | |
| 7,083,622 B2 | 8/2006 | Simonson | |
| 7,083,649 B2 | 8/2006 | Zucherman et al. | |
| 7,087,055 B2 | 8/2006 | Lim et al. | |
| 7,090,698 B2 | 8/2006 | Goble et al. | |
| 7,108,705 B2 | 9/2006 | Davison et al. | |
| 7,125,410 B2 | 10/2006 | Freudiger et al. | |
| 7,137,985 B2 | 11/2006 | Jahng | |
| 7,182,783 B2 | 2/2007 | Trieu | |
| 7,188,626 B2 | 3/2007 | Foley et al. | |
| 7,207,992 B2 | 4/2007 | Ritland | |
| 7,229,441 B2 | 6/2007 | Trieu et al. | |
| 7,252,673 B2 | 8/2007 | Lim | |
| 7,282,065 B2 | 10/2007 | Kirschman | |
| 7,294,129 B2 | 11/2007 | Hawkins et al. | |
| 7,306,603 B2 | 12/2007 | Boehm, Jr. et al. | |
| 7,329,258 B2 | 2/2008 | Studer | |
| 7,335,200 B2 | 2/2008 | Carli et al. | |
| 7,341,587 B2 | 3/2008 | Molz, IV et al. | |
| 7,354,453 B2 | 4/2008 | McAfee | |
| 7,361,196 B2 | 4/2008 | Fallin et al. | |
| 7,377,921 B2 | 5/2008 | Studer et al. | |
| 7,377,942 B2 | 5/2008 | Berry | |
| 7,406,775 B2 | 8/2008 | Funk et al. | |
| 7,476,238 B2 | 1/2009 | Panjabi | |
| 7,691,131 B2 * | 4/2010 | Graf | 606/256 |
| 7,776,071 B2 | 8/2010 | Fortin et al. | |
| 7,828,823 B2 | 11/2010 | Rogeau et al. | |
| 7,935,134 B2 | 5/2011 | Reglos et al. | |
| 7,998,175 B2 | 8/2011 | Kim et al. | |
| 8,025,680 B2 | 9/2011 | Hayes et al. | |
| 2001/0037111 A1 | 11/2001 | Dixon et al. | |
| 2002/0065557 A1 | 5/2002 | Goble et al. | |
| 2002/0068975 A1 | 6/2002 | Teitelbaum et al. | |
| 2002/0072800 A1 | 6/2002 | Goble et al. | |
| 2002/0082600 A1 | 6/2002 | Shaolian et al. | |
| 2002/0095154 A1 | 7/2002 | Atkinson | |
| 2002/0120270 A1 | 8/2002 | Trieu et al. | |
| 2002/0123806 A1 | 9/2002 | Reiley | |
| 2002/0133155 A1 * | 9/2002 | Ferree | 606/61 |
| 2002/0151895 A1 | 10/2002 | Soboleski et al. | |
| 2002/0198526 A1 | 12/2002 | Shaolian et al. | |
| 2003/0004572 A1 | 1/2003 | Goble et al. | |
| 2003/0028250 A1 | 2/2003 | Reiley et al. | |
| 2003/0032965 A1 | 2/2003 | Schneiderman | |
| 2003/0040797 A1 | 2/2003 | Fallin et al. | |
| 2003/0055427 A1 | 3/2003 | Graf | |
| 2003/0093078 A1 | 5/2003 | Ritland | |
| 2003/0171749 A1 | 9/2003 | Le Couedic et al. | |
| 2003/0171750 A1 | 9/2003 | Chin | |
| 2003/0208202 A1 | 11/2003 | Falahee | |
| 2003/0208203 A1 | 11/2003 | Lim et al. | |
| 2003/0220642 A1 | 11/2003 | Freudiger | |
| 2003/0220643 A1 | 11/2003 | Ferree | |
| 2003/0229347 A1 | 12/2003 | Sherman et al. | |
| 2003/0236520 A1 | 12/2003 | Lim et al. | |
| 2004/0002708 A1 | 1/2004 | Ritland | |
| 2004/0006341 A1 | 1/2004 | Shaolian et al. | |
| 2004/0006344 A1 | 1/2004 | Nguyen et al. | |
| 2004/0039384 A1 | 2/2004 | Boehm et al. | |
| 2004/0049189 A1 | 3/2004 | Le Couedic et al. | |
| 2004/0064140 A1 | 4/2004 | Taylor et al. | |
| 2004/0073215 A1 | 4/2004 | Carli | |
| 2004/0080418 A1 | 4/2004 | Dahlborn et al. | |
| 2004/0082954 A1 | 4/2004 | Teitelbaum et al. | |
| 2004/0087947 A1 | 5/2004 | Lim et al. | |
| 2004/0092931 A1 | 5/2004 | Taylor et al. | |
| 2004/0116927 A1 * | 6/2004 | Graf | 606/61 |
| 2004/0127989 A1 | 7/2004 | Dooris et al. | |
| 2004/0138662 A1 | 7/2004 | Landry et al. | |

| | | | | | | |
|---|---|---|---|---|---|---|
| 2004/0143265 A1 | 7/2004 | Landry et al. | | 2005/0197700 A1 | 9/2005 | Boehm, Jr. et al. |
| 2004/0143270 A1 | 7/2004 | Zucherman et al. | | 2005/0197705 A1 | 9/2005 | Arnin et al. |
| 2004/0147928 A1 | 7/2004 | Landry et al. | | 2005/0203511 A1 | 9/2005 | Wilson-MacDonald et al. |
| 2004/0193158 A1 | 9/2004 | Lim et al. | | 2005/0203513 A1 | 9/2005 | Jahng et al. |
| 2004/0215190 A1 | 10/2004 | Nguyen et al. | | 2005/0203514 A1 | 9/2005 | Jahng et al. |
| 2004/0225289 A1 | 11/2004 | Biedermann et al. | | 2005/0203517 A1 | 9/2005 | Jahng et al. |
| 2004/0230201 A1 | 11/2004 | Yuan et al. | | 2005/0209593 A1 | 9/2005 | Kolb |
| 2004/0230304 A1 | 11/2004 | Yuan et al. | | 2005/0209694 A1 | 9/2005 | Loeb |
| 2004/0236328 A1 | 11/2004 | Paul et al. | | 2005/0215999 A1 | 9/2005 | Birkmeyer et al. |
| 2004/0236329 A1 | 11/2004 | Panjabi | | 2005/0216000 A1 | 9/2005 | Colleran et al. |
| 2004/0267260 A1 | 12/2004 | Mack et al. | | 2005/0222569 A1 | 10/2005 | Panjabi |
| 2005/0010217 A1 | 1/2005 | Dalton | | 2005/0234551 A1 | 10/2005 | Fallin et al. |
| 2005/0010953 A1 | 1/2005 | Carney et al. | | 2005/0235508 A1 | 10/2005 | Augostino et al. |
| 2005/0010954 A1 | 1/2005 | Binder | | 2005/0240264 A1 | 10/2005 | Tokish, Jr. et al. |
| 2005/0010956 A1 | 1/2005 | Moon et al. | | 2005/0240265 A1 | 10/2005 | Kuiper et al. |
| 2005/0021031 A1 | 1/2005 | Foley et al. | | 2005/0245928 A1 | 11/2005 | Colleran et al. |
| 2005/0027361 A1 | 2/2005 | Reiley | | 2005/0245930 A1 | 11/2005 | Timm et al. |
| 2005/0033295 A1 | 2/2005 | Wisnewski | | 2005/0249697 A1 | 11/2005 | Uhrich et al. |
| 2005/0033434 A1 | 2/2005 | Berry | | 2005/0261682 A1 | 11/2005 | Ferree |
| 2005/0033439 A1 | 2/2005 | Gordon et al. | | 2005/0261685 A1 | 11/2005 | Fortin et al. |
| 2005/0038432 A1 | 2/2005 | Shaolian et al. | | 2005/0273167 A1 | 12/2005 | Triplett et al. |
| 2005/0038440 A1 | 2/2005 | Larson et al. | | 2005/0277921 A1 | 12/2005 | Eisermann et al. |
| 2005/0043742 A1 | 2/2005 | Bruneau et al. | | 2005/0277922 A1 | 12/2005 | Trieu et al. |
| 2005/0043797 A1 | 2/2005 | Lee | | 2005/0288670 A1 | 12/2005 | Panjabi et al. |
| 2005/0043799 A1 | 2/2005 | Reiley | | 2006/0015100 A1 | 1/2006 | Panjabi et al. |
| 2005/0049705 A1 | 3/2005 | Hale et al. | | 2006/0036240 A1 | 2/2006 | Colleran et al. |
| 2005/0049708 A1 | 3/2005 | Atkinson et al. | | 2006/0036244 A1 | 2/2006 | Spitler et al. |
| 2005/0055096 A1 | 3/2005 | Serhan et al. | | 2006/0036255 A1 | 2/2006 | Pond et al. |
| 2005/0056979 A1 | 3/2005 | Studer et al. | | 2006/0052785 A1 | 3/2006 | Augostino et al. |
| 2005/0065514 A1 | 3/2005 | Studer | | 2006/0058791 A1 | 3/2006 | Broman et al. |
| 2005/0065515 A1 | 3/2005 | Jahng | | 2006/0079894 A1 | 4/2006 | Colleran et al. |
| 2005/0065516 A1* | 3/2005 | Jahng ............................ 606/61 | | 2006/0084976 A1 | 4/2006 | Borgstrom et al. |
| 2005/0065517 A1 | 3/2005 | Chin | | 2006/0084982 A1 | 4/2006 | Kim |
| 2005/0070917 A1 | 3/2005 | Justis | | 2006/0084984 A1 | 4/2006 | Kim |
| 2005/0080418 A1 | 4/2005 | Simonson et al. | | 2006/0084987 A1 | 4/2006 | Kim |
| 2005/0080486 A1 | 4/2005 | Fallin et al. | | 2006/0084991 A1 | 4/2006 | Borgstrom et al. |
| 2005/0085813 A1 | 4/2005 | Spitler et al. | | 2006/0085072 A1 | 4/2006 | Funk et al. |
| 2005/0085815 A1 | 4/2005 | Harms et al. | | 2006/0106380 A1 | 5/2006 | Colleran |
| 2005/0085912 A1 | 4/2005 | Arnin et al. | | 2006/0106394 A1 | 5/2006 | Colleran |
| 2005/0101953 A1 | 5/2005 | Simonson | | 2006/0142759 A1 | 6/2006 | Arnin et al. |
| 2005/0101956 A1 | 5/2005 | Simonson | | 2006/0149238 A1 | 7/2006 | Sherman et al. |
| 2005/0102028 A1 | 5/2005 | Arnin et al. | | 2006/0149239 A1 | 7/2006 | Winslow et al. |
| 2005/0113927 A1 | 5/2005 | Malek | | 2006/0149254 A1 | 7/2006 | Lauryssen et al. |
| 2005/0119748 A1 | 6/2005 | Reiley et al. | | 2006/0149272 A1 | 7/2006 | Winslow et al. |
| 2005/0124991 A1 | 6/2005 | Jahng | | 2006/0149289 A1 | 7/2006 | Winslow et al. |
| 2005/0125066 A1 | 6/2005 | McAfee | | 2006/0149373 A1 | 7/2006 | Winslow et al. |
| 2005/0131405 A1 | 6/2005 | Molz, IV et al. | | 2006/0149374 A1 | 7/2006 | Winslow et al. |
| 2005/0131406 A1 | 6/2005 | Reiley et al. | | 2006/0149375 A1 | 7/2006 | Yuan et al. |
| 2005/0131407 A1* | 6/2005 | Sicvol et al. ...................... 606/61 | | 2006/0149383 A1 | 7/2006 | Arnin et al. |
| 2005/0131408 A1 | 6/2005 | Sicvol et al. | | 2006/0149389 A1 | 7/2006 | Romagnoli |
| 2005/0131409 A1 | 6/2005 | Chervitz et al. | | 2006/0173454 A1 | 8/2006 | Spitler et al. |
| 2005/0131422 A1 | 6/2005 | Anderson et al. | | 2006/0189983 A1 | 8/2006 | Fallin et al. |
| 2005/0131537 A1 | 6/2005 | Hoy et al. | | 2006/0189984 A1 | 8/2006 | Fallin et al. |
| 2005/0131538 A1 | 6/2005 | Chervitz et al. | | 2006/0190083 A1 | 8/2006 | Arnin et al. |
| 2005/0131545 A1 | 6/2005 | Chervitz et al. | | 2006/0195086 A1 | 8/2006 | Sybert |
| 2005/0143737 A1 | 6/2005 | Pafford et al. | | 2006/0195088 A1 | 8/2006 | Sacher et al. |
| 2005/0143823 A1 | 6/2005 | Boyd et al. | | 2006/0200137 A1 | 9/2006 | Soboleski et al. |
| 2005/0149020 A1 | 7/2005 | Jahng et al. | | 2006/0217718 A1 | 9/2006 | Chervitz et al. |
| 2005/0154390 A1 | 7/2005 | Biedermann et al. | | 2006/0217719 A1 | 9/2006 | Albert et al. |
| 2005/0154461 A1 | 7/2005 | Humphreys et al. | | 2006/0235388 A1 | 10/2006 | Justis et al. |
| 2005/0154464 A1 | 7/2005 | Humphreys et al. | | 2006/0235414 A1 | 10/2006 | Lim et al. |
| 2005/0154465 A1 | 7/2005 | Hodges et al. | | 2006/0241642 A1 | 10/2006 | Arnin et al. |
| 2005/0154466 A1 | 7/2005 | Humphreys et al. | | 2006/0241758 A1 | 10/2006 | Peterman et al. |
| 2005/0154467 A1 | 7/2005 | Peterman et al. | | 2006/0241759 A1 | 10/2006 | Trieu |
| 2005/0165396 A1 | 7/2005 | Fortin et al. | | 2006/0241768 A1 | 10/2006 | Trieu |
| 2005/0171543 A1 | 8/2005 | Timm et al. | | 2006/0241769 A1 | 10/2006 | Gordon et al. |
| 2005/0171608 A1 | 8/2005 | Peterman et al. | | 2006/0247623 A1 | 11/2006 | Anderson et al. |
| 2005/0171609 A1 | 8/2005 | Humphreys et al. | | 2006/0247632 A1 | 11/2006 | Winslow et al. |
| 2005/0171610 A1 | 8/2005 | Humphreys et al. | | 2006/0247633 A1 | 11/2006 | Winslow et al. |
| 2005/0177156 A1 | 8/2005 | Timm et al. | | 2006/0247637 A1 | 11/2006 | Colleran et al. |
| 2005/0177157 A1 | 8/2005 | Jahng | | 2006/0247650 A1 | 11/2006 | Yerby et al. |
| 2005/0177164 A1 | 8/2005 | Walters et al. | | 2006/0247769 A1 | 11/2006 | Molz et al. |
| 2005/0177166 A1 | 8/2005 | Timm et al. | | 2006/0247773 A1 | 11/2006 | Stamp |
| 2005/0177240 A1 | 8/2005 | Blain | | 2006/0260483 A1 | 11/2006 | Hartmann et al. |
| 2005/0182400 A1 | 8/2005 | White | | 2006/0264934 A1 | 11/2006 | Fallin |
| 2005/0182401 A1 | 8/2005 | Timm et al. | | 2006/0264962 A1 | 11/2006 | Chin et al. |
| 2005/0182409 A1 | 8/2005 | Callahan et al. | | 2006/0265074 A1 | 11/2006 | Krishna et al. |
| 2005/0187548 A1 | 8/2005 | Butler | | 2006/0271198 A1 | 11/2006 | McAfee |
| 2005/0192574 A1 | 9/2005 | Blain | | 2006/0276801 A1 | 12/2006 | Yerby et al. |

| | | | |
|---|---|---|---|
| 2006/0276897 A1 | 12/2006 | Winslow et al. | |
| 2006/0282075 A1 | 12/2006 | Labrom et al. | |
| 2006/0282077 A1 | 12/2006 | Labrom et al. | |
| 2006/0282078 A1 | 12/2006 | Labrom et al. | |
| 2006/0282079 A1 | 12/2006 | Labrom et al. | |
| 2006/0282080 A1 | 12/2006 | Albert et al. | |
| 2006/0293657 A1 | 12/2006 | Hartmann | |
| 2007/0005062 A1 | 1/2007 | Lange et al. | |
| 2007/0005063 A1 | 1/2007 | Bruneau et al. | |
| 2007/0016191 A1 | 1/2007 | Culbert et al. | |
| 2007/0016193 A1 | 1/2007 | Ritland | |
| 2007/0016195 A1 | 1/2007 | Winslow et al. | |
| 2007/0016196 A1 | 1/2007 | Winslow et al. | |
| 2007/0016218 A1 | 1/2007 | Winslow et al. | |
| 2007/0016296 A1 | 1/2007 | Triplett et al. | |
| 2007/0043358 A1 | 2/2007 | Molz et al. | |
| 2007/0043359 A1 | 2/2007 | Altarac | |
| 2007/0049931 A1 | 3/2007 | Justis et al. | |
| 2007/0055257 A1 | 3/2007 | Vaccaro et al. | |
| 2007/0073289 A1 | 3/2007 | Kwak et al. | |
| 2007/0100341 A1 | 5/2007 | Reglos et al. | |
| 2007/0118122 A1 | 5/2007 | Butler et al. | |
| 2007/0161988 A1 | 7/2007 | Drewry et al. | |
| 2007/0161997 A1 | 7/2007 | Thramann et al. | |
| 2007/0239159 A1 | 10/2007 | Altarac et al. | |
| 2008/0045951 A1 | 2/2008 | Fanger et al. | |
| 2008/0097441 A1 | 4/2008 | Hayes et al. | |
| 2008/0154307 A1 | 6/2008 | Colleran et al. | |
| 2008/0262554 A1 | 10/2008 | Reglos et al. | |
| 2009/0030465 A1 | 1/2009 | Altarac et al. | |
| 2009/0228045 A1 | 9/2009 | Hayes et al. | |
| 2010/0036423 A1 | 2/2010 | Hayes et al. | |

FOREIGN PATENT DOCUMENTS

| | | | |
|---|---|---|---|
| EP | 0767636 B1 | 1/1999 | |
| EP | 1138268 A1 | 10/2001 | |
| EP | 0951246 B1 | 7/2003 | |
| EP | 1056408 B1 | 12/2003 | |
| EP | 1145602 B1 | 3/2004 | |
| EP | 1415602 | 5/2004 | |
| EP | 0986339 B1 | 10/2004 | |
| EP | 1399078 B1 | 12/2004 | |
| EP | 1303225 B1 | 5/2005 | |
| EP | 1415603 A3 | 7/2005 | |
| EP | 1810624 | 7/2007 | |
| EP | 1810624 A1 | 7/2007 | |
| FR | 2728454 | 6/1996 | |
| WO | WO 91/16018 | 10/1991 | |
| WO | WO 94/26192 | 11/1994 | |
| WO | WO 96/00049 | 1/1996 | |
| WO | WO 98/48717 | 11/1998 | |
| WO | WO 98/55038 | 12/1998 | |
| WO | WO 00/62684 | 10/2000 | |
| WO | WO 01/30248 A1 | 5/2001 | |
| WO | WO 01/41681 | 6/2001 | |
| WO | WO 02/38060 A1 | 5/2002 | |
| WO | WO 02/065954 A1 | 8/2002 | |
| WO | WO 02/067793 | 9/2002 | |
| WO | WO-02067793 A3 | 9/2002 | |
| WO | WO 02/102259 | 12/2002 | |
| WO | WO 03/047442 A1 | 6/2003 | |
| WO | WO 03/075805 A1 | 9/2003 | |
| WO | WO 03/094699 A2 | 11/2003 | |
| WO | 03101350 | 12/2003 | |
| WO | WO 03/101350 | 12/2003 | |
| WO | WO-2004008949 A3 | 1/2004 | |
| WO | WO-2004047617 A3 | 6/2004 | |
| WO | WO 2005/030031 A2 | 4/2005 | |
| WO | WO 2005/030066 A1 | 4/2005 | |
| WO | WO 2005/030067 A1 | 4/2005 | |
| WO | WO-2005030029 | 4/2005 | |
| WO | WO 2005/041799 A1 | 5/2005 | |
| WO | WO 2005/044152 A1 | 5/2005 | |
| WO | WO-2005046515 | 5/2005 | |
| WO | WO 2005/053572 A3 | 6/2005 | |
| WO | WO 2005/055874 A2 | 6/2005 | |
| WO | 2005065516 | 7/2005 | |
| WO | WO 2005/065515 A1 | 7/2005 | |
| WO | WO 2005/065516 A2 | 7/2005 | |
| WO | WO 2005/067824 A1 | 7/2005 | |
| WO | WO 2005/070278 A2 | 8/2005 | |
| WO | WO 2005/070349 A1 | 8/2005 | |
| WO | WO 2005/070350 A2 | 8/2005 | |
| WO | WO 2005/070351 A1 | 8/2005 | |
| WO | WO 2005/070352 A2 | 8/2005 | |
| WO | WO 2005/070353 A1 | 8/2005 | |
| WO | WO 2005/070354 A2 | 8/2005 | |
| WO | WO-2005077113 | 8/2005 | |
| WO | WO 2005/079426 A2 | 9/2005 | |
| WO | WO 2005/079672 A2 | 9/2005 | |
| WO | WO 2005/079711 A1 | 9/2005 | |
| WO | WO 2005/084590 A1 | 9/2005 | |
| WO | WO 2005/087121 A1 | 9/2005 | |
| WO | WO 2005/092223 A2 | 10/2005 | |
| WO | WO-2005094704 | 10/2005 | |
| WO | WO-2006016371 | 2/2006 | |
| WO | WO-2006017507 | 2/2006 | |
| WO | 2006045091 | 4/2006 | |
| WO | WO-2006042188 | 4/2006 | |
| WO | WO-2006042189 | 4/2006 | |
| WO | WO-2006047363 | 5/2006 | |
| WO | WO-2006063107 | 6/2006 | |
| WO | WO-2006102443 | 9/2006 | |
| WO | WO-2006108067 | 10/2006 | |
| WO | WO-2006125142 A2 | 11/2006 | |
| WO | 2007014119 | 2/2007 | |
| WO | WO-2007021588 | 2/2007 | |
| WO | WO-2007075375 | 7/2007 | |
| WO | 2007117366 | 10/2007 | |
| WO | 2007136612 | 11/2007 | |
| WO | 2008069835 | 6/2008 | |
| WO | 2008153747 | 12/2008 | |
| WO | 2009042489 | 4/2009 | |
| WO | 2009100190 | 8/2009 | |
| WO | 2010019791 | 2/2010 | |

OTHER PUBLICATIONS

Co-pending U.S. Appl. No. 11/427,738.
Co-pending U.S. Appl. No. 11/436,407.
U.S. Appl. No. 60/701,660.
International Search Report and Written Opinion for application No. PCT/US07/11573, Mail Date Apr. 23, 2008, 8 pages.
International Search Report and Written Opinion for application No. PCT/US06/28586, Mail Date Apr. 27, 2007, 14 pages.
International Search Report and Written Opinion for application No. PCT/US07/04726, Mail Date Jul. 8, 2008, 7 pages.
International Search Report and Written Opinion for application No. PCT/US05/38021, Mail Date Apr. 10, 2006, 7 pages.
International Search Report for Application No. PCT/US07/11597; Applicant: Vertiflex, Inc.; Date Mailed: Oct. 2, 2008 (2 pages).
Final Office Action for U.S. Appl. No. 10/970,366, Mail Date: Oct. 5, 2009, 8 pages.
Non-Final Office Action for U.S. Appl. No. 10/970,366, Mail Date: Nov. 25, 2008, 7 pages.
Non-Final Office Action for U.S. Appl. No. 11/033,452, Mail Date: Dec. 11, 2008, 6 pages.
Non-Final Office Action for U.S. Appl. No. 11/033,452, Mail Date: 10/13, 2009, 7 pages.
Non-Final Office Action for U.S. Appl. No. 11/436,407, Mail Date: Jun. 12, 2009, 13 pages.
Non-Final Office Action for U.S. Appl. No. 11/427,738, Mail Date: Dec. 29, 2009, 8 pages.
Non-Final Office Action for U.S. Appl. No. 11/362,366, Mail Date: Apr. 7, 2009, 6 pages.
International Search Report for application No. PCT/US07/11597, Applicant: Vertiflex, Inc.; Mail Date Oct. 2, 2008, 2 pages.
International Preliminary Report on Patentability (mailed on Nov. 17, 2008) and Written Opinion (mailed on Oct. 2, 2008) for application No. PCT/US07/11597, Applicant: Vertiflex, Inc.; 6 pages.
Non-Final Office Action for U.S. Appl. No. 11/427,738 mailed on Mar. 10, 2009.
Non-Final Office Action for U.S. Appl. No. 11/427,738 mailed on Aug. 5, 2010.

International Search Report (mailed on Apr. 23, 2008) for application No. PCT/US07/11573. pp. 1.
International Preliminary Report on Patentability (issued on Nov. 17, 2008) and Written Opinion (mailed on Apr. 23, 2008) for application No. PCT/US07/11573. pp. 4.
International Search Report (mailed on Jul. 27, 2007) for application No. PCT/US06/28586. pp. 2.
International Preliminary Report on Patentability (issued on Jan. 22, 2008) and Written Opinion (mailed on Jul. 27, 2007,) for application No. PCT/US06/28586. pp. 9.
International Search Report (mailed on Dec. 19, 2008) for Application No. PCT/US2008/006598, pp. 2.
International Preliminary Report on Patentability (mailed on Dec. 1, 2009) and Written Opinion (mailed on Dec. 19, 2008) for Application No. PCT/US2008/006598, pp. 5.
International Search Report (mailed on Mar. 31, 2009) for Application No. PCT/US2008/076815, pp. 3.
International Preliminary Report on Patentability (mailed on Mar. 24, 2010) and Written Opinion (mailed on Mar. 31, 2009) for Application No. PCT/US2008/076815, pp. 5.
International Search Report for application No. PCT/US09/033174, Mail Date Aug. 27, 2009. 2 pages.
International Preliminary Report on Patentability (issued on Aug. 10, 2010) and Written Opinion (mailed on Aug. 27, 2009) for application No. PCT/US09/033174, 5 pages.
International Search Report and Written Opinion for application No. PCT/US09/053740, Mail Date Mar. 24, 2010. 4 pages.
International Preliminary Report on Patentability and Written Opinion for application No. PCT/US09/053740, Mail Date Mar. 24, 2010. 11 pages.
International Preliminary Report on Patentability (issued on Aug. 26, 2008) and Written Opinion (mailed on Jul. 8, 2008) for application No. PCT/US07/04726, 4 pages.
International Search Report (mailed on Jul. 8, 2008) for application no. PCT/US07/04726. pp. 1.
Requirement for Restriction/Election for U.S. Appl. No. 10/970,366 mailed on Apr. 3, 2008.
Non-Final Office Action for U.S. Appl. No. 10/970,366 mailed on Aug. 5, 2010.
European Supplementary Search Report for Application No. EP05816030; Applicant: Vertiflex, Inc.; Date Mail: Sep. 7, 2009. pp. 6.
Final Office Action for U.S. Appl. No. 11/033,452 mailed on Aug. 5, 2010.
International Search Report (mailed on Apr. 10, 2006) for application No. PCT/US05/38021. pp. 1.
International Preliminary Report on Patentability (issued on Apr. 24, 2007) and Written Opinion (mailed on Apr. 10, 2008) for application No. PCT/US05/38021. pp. 4.
Examiner's First Report on Australian Patent Application No. 2005295209 mailed on Jun. 22, 2010. pp. 3.
Non-Final Office Action for U.S. Appl. No. 11/436,407 mailed on Oct. 29, 2010.
Final Office Action for U.S. Appl. No. 11/362,366 mailed on Apr. 23, 2010, pp. 6.
Final Office Action for U.S. Appl. No. 11/436,407 mailed on Apr. 5, 2010.
Final Office Action for U.S. Appl. No. 10/970,366 mailed on Jan. 13, 2011.
Advisory Action for U.S. Appl. No. 11/006,495 mailed on Dec. 30, 2010.
Non-Final Office Action for U.S. Appl. No. 11/033,452 mailed on Dec. 23, 2010.
Non-Final Office Action for U.S. Appl. No. 11/362,366 mailed on Mar. 18, 2011.
Non-Final Office Action for U.S. Appl. No. 12/154,540 mailed on Apr. 11, 2011.
Non-Final Office Action for U.S. Appl. No. 12/233,212 mailed on Apr. 5, 2011.
Non-Final Office Action for U.S. Appl. No. 12/366,089 mailed on Apr. 12, 2011.
Advisory Action for U.S. Appl. No. 10/970,366 mailed on Apr. 28, 2011.
Non-Final Office Action for U.S. Appl. No. 11/006,495 mailed on Mar. 31, 2011.
Communication pursuant to Article 94(3) EPC for Application No. EP05816030; Applicant: Vertiflex, Inc.; Date Mail: May 2, 2011. pp. 9.
Non-Final Office Action for U.S. Appl. No. 10/970,366 mailed on Aug. 29, 2011.

* cited by examiner

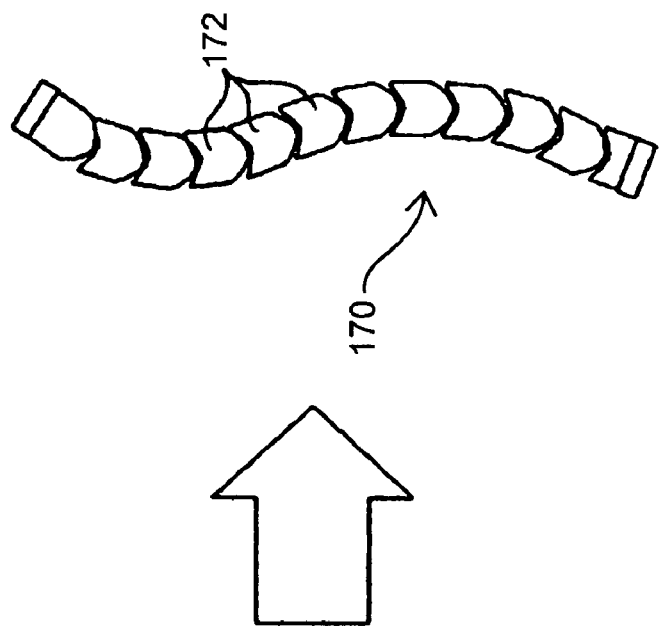
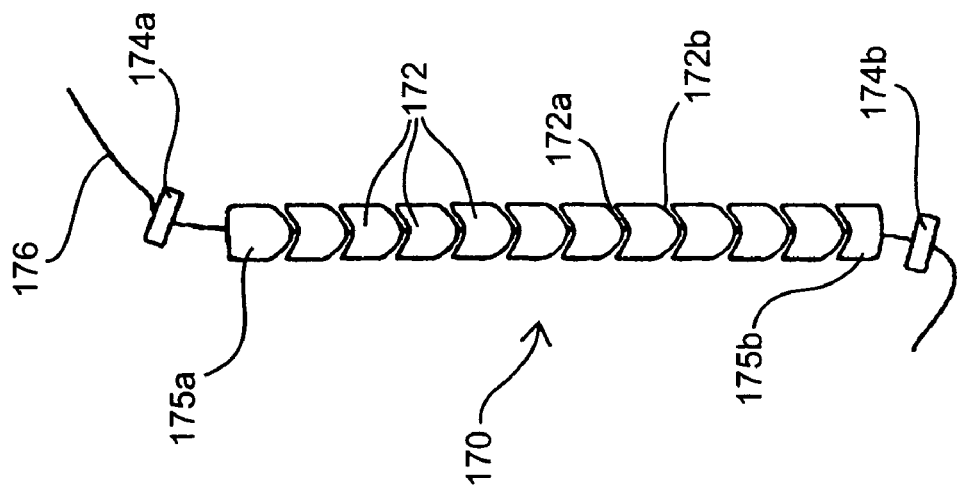
FIG. 18B
FIG. 18A

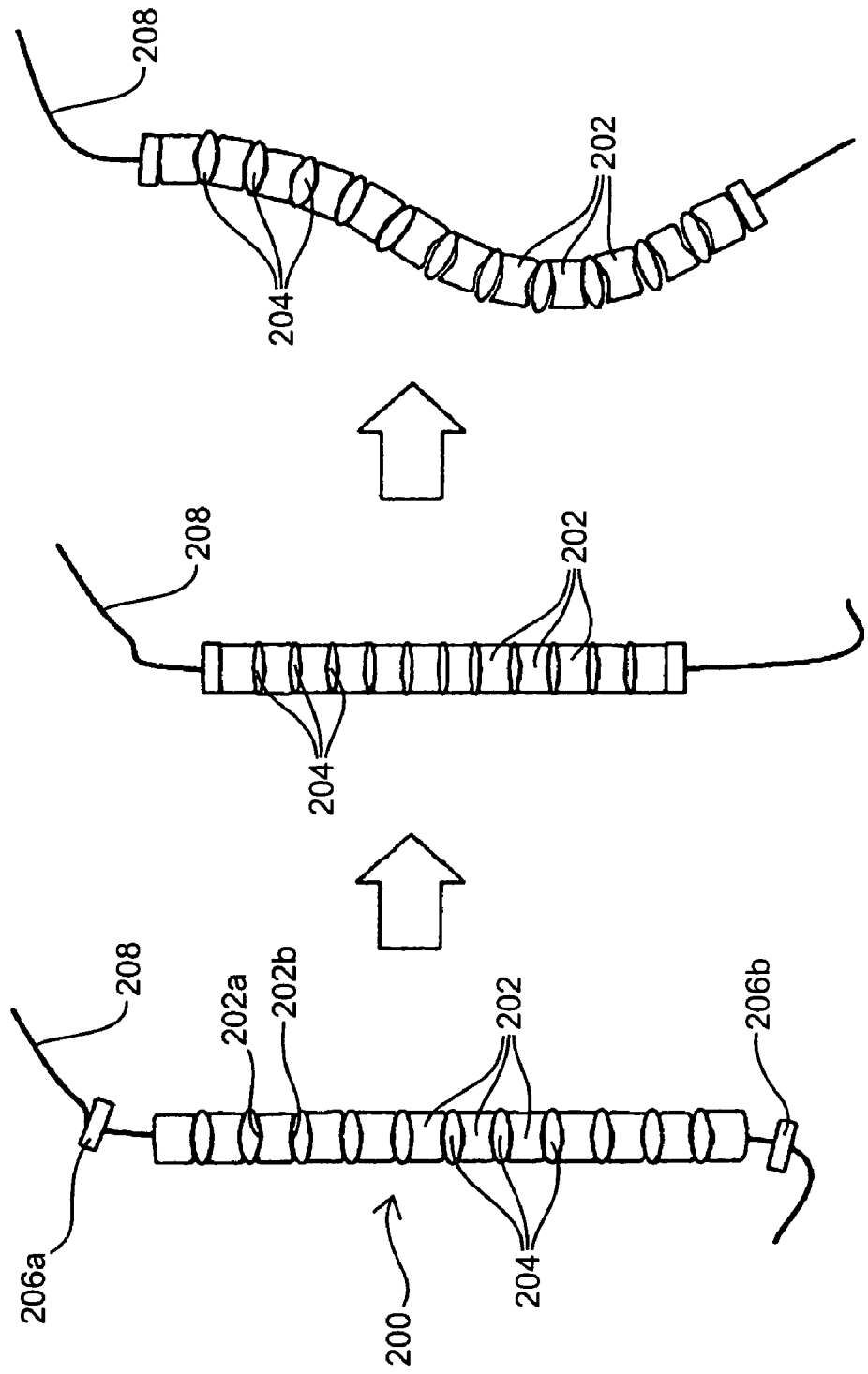

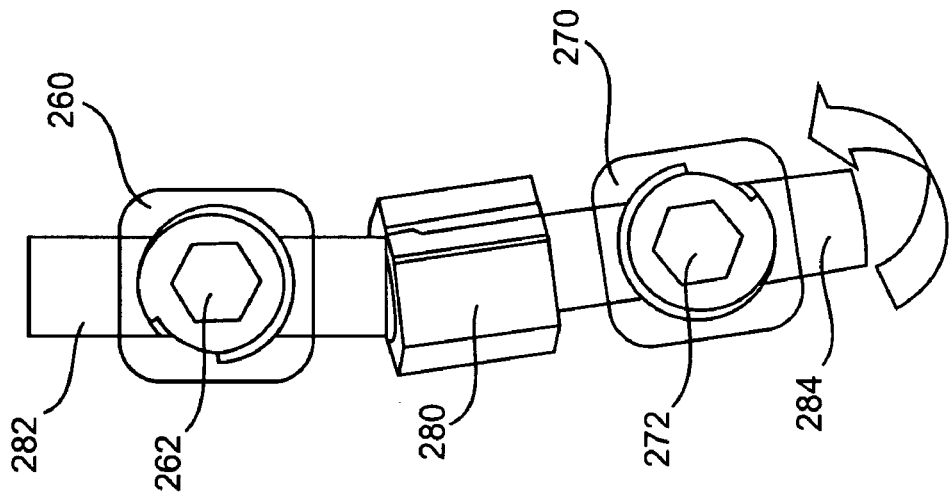
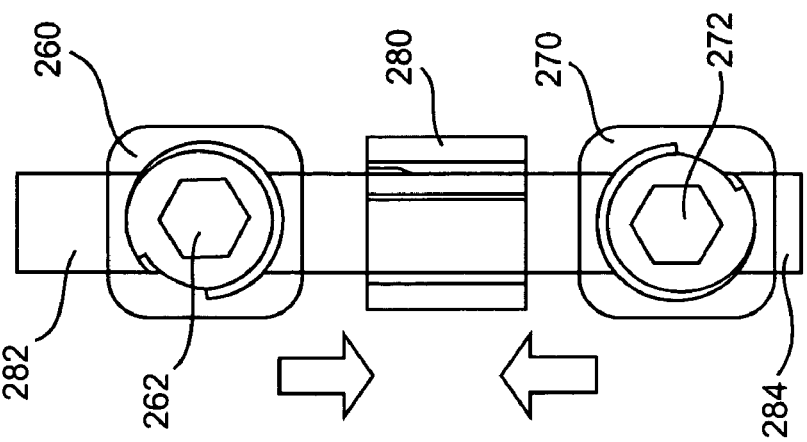

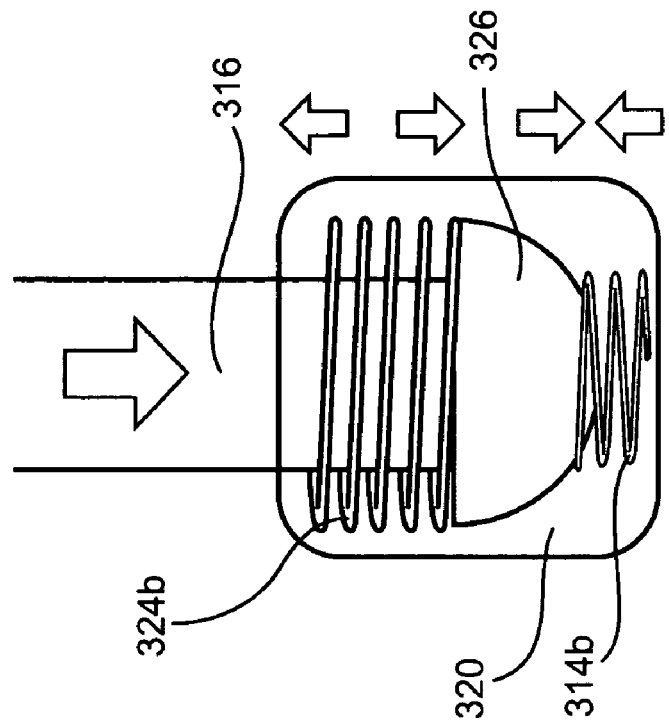
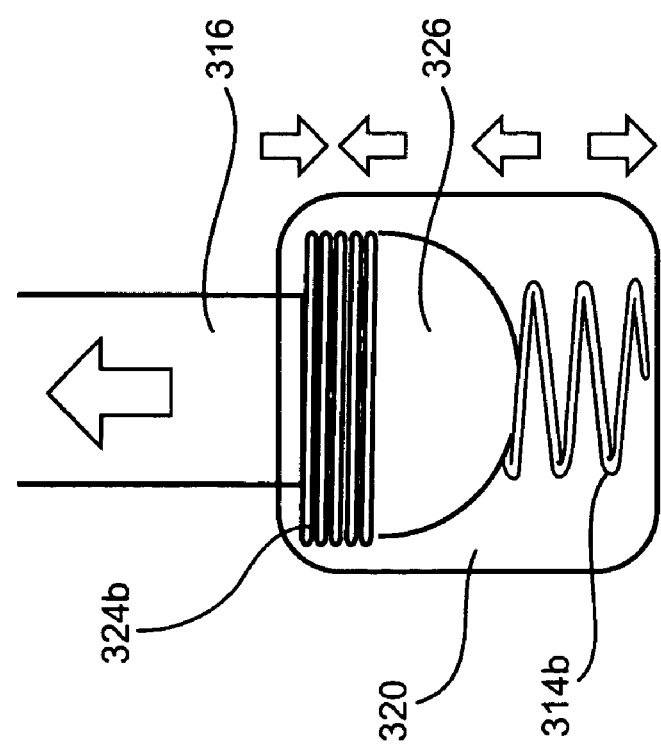

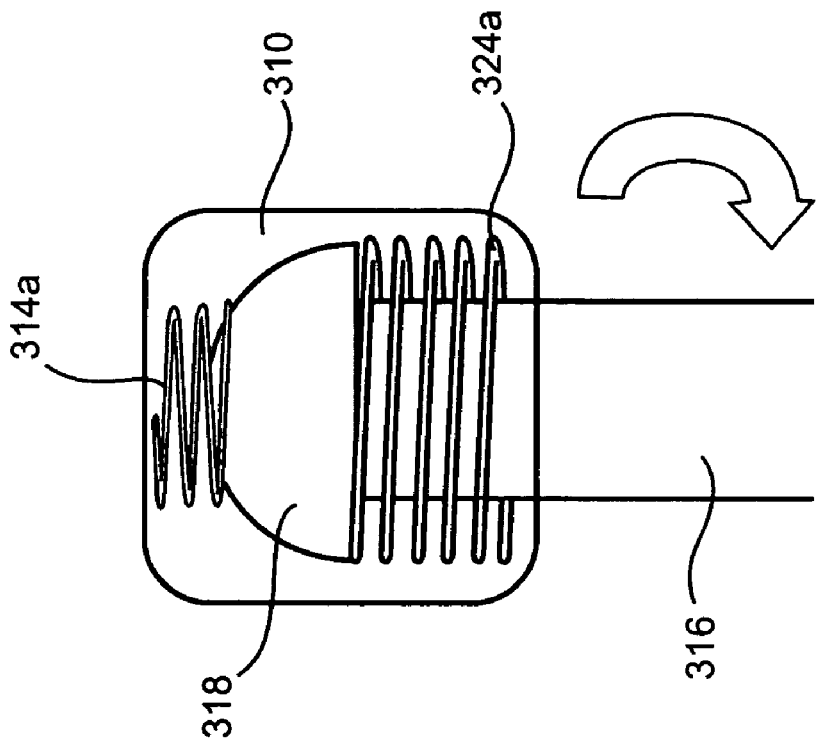
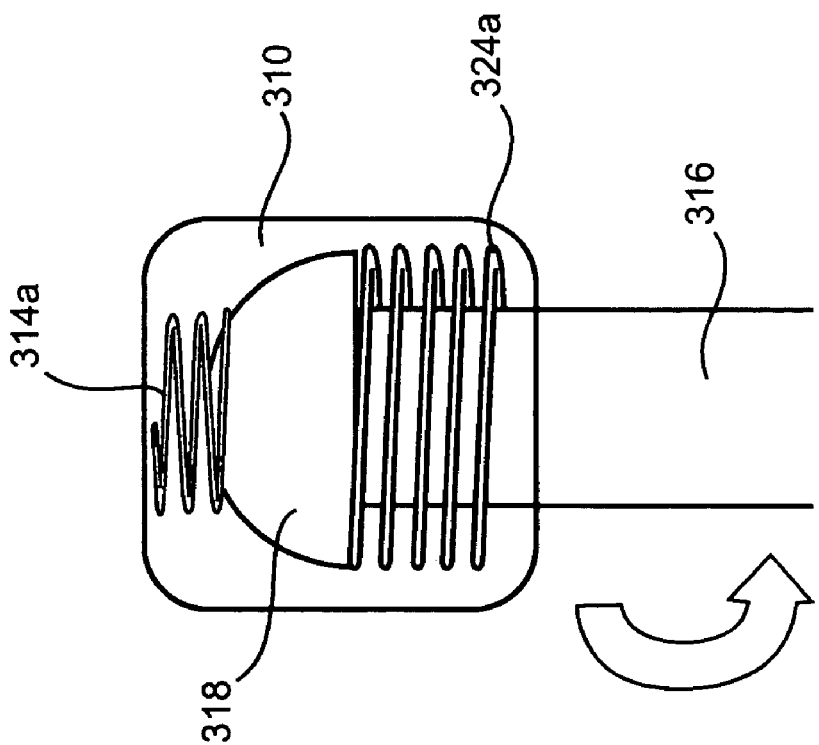

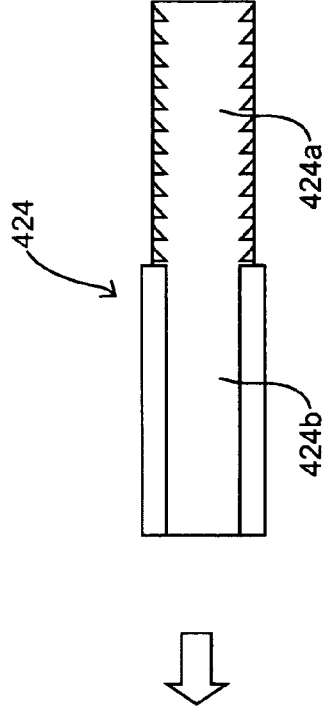
FIG. 35A
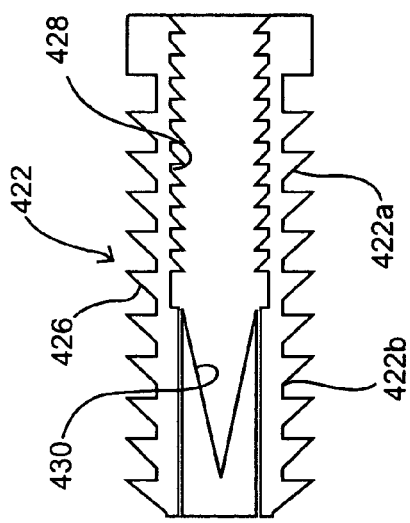
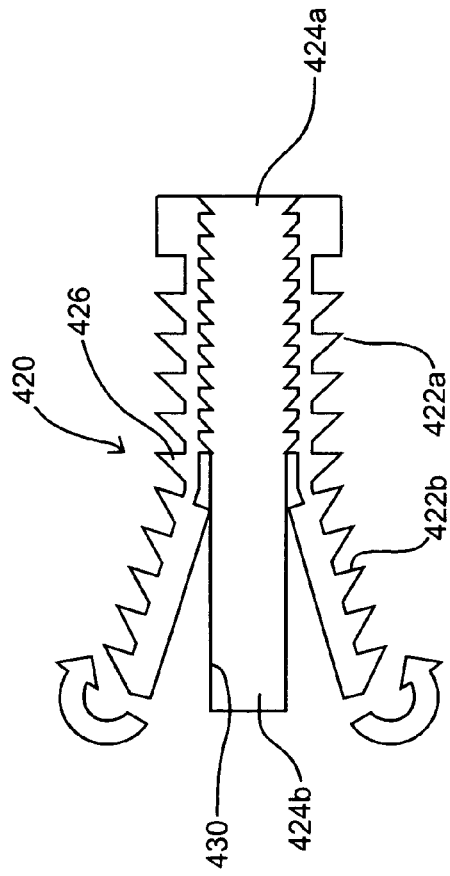
FIG. 35B

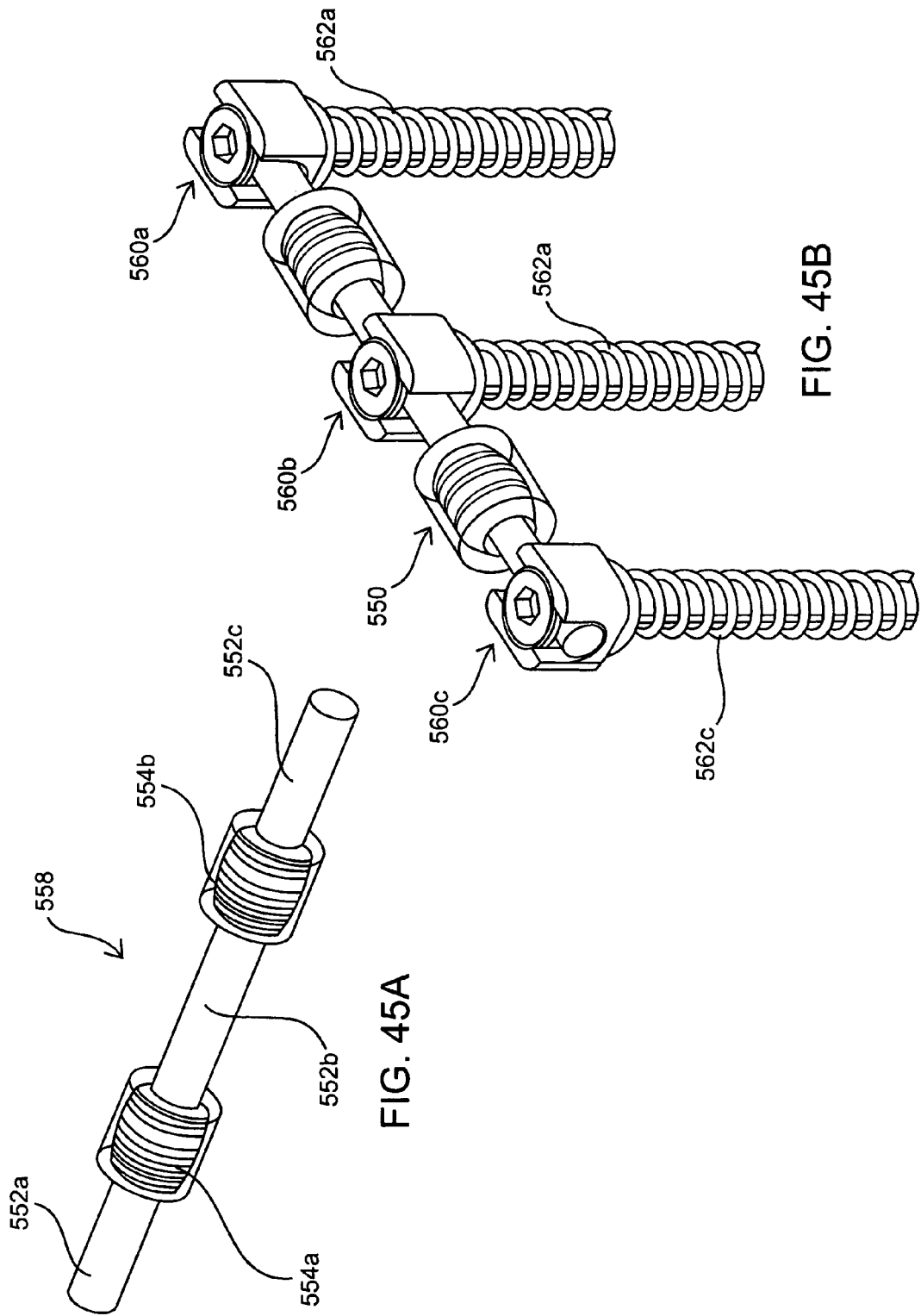

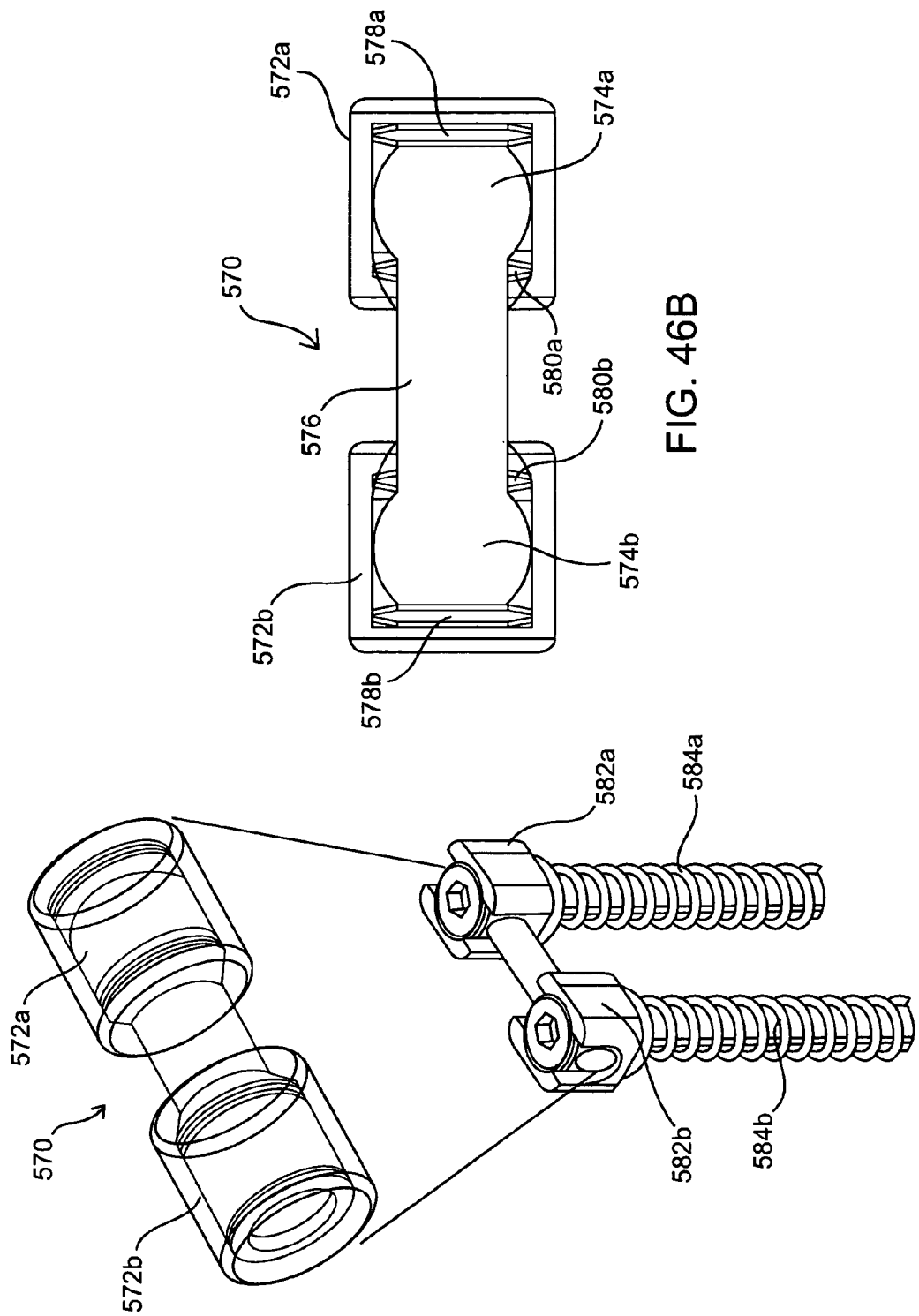

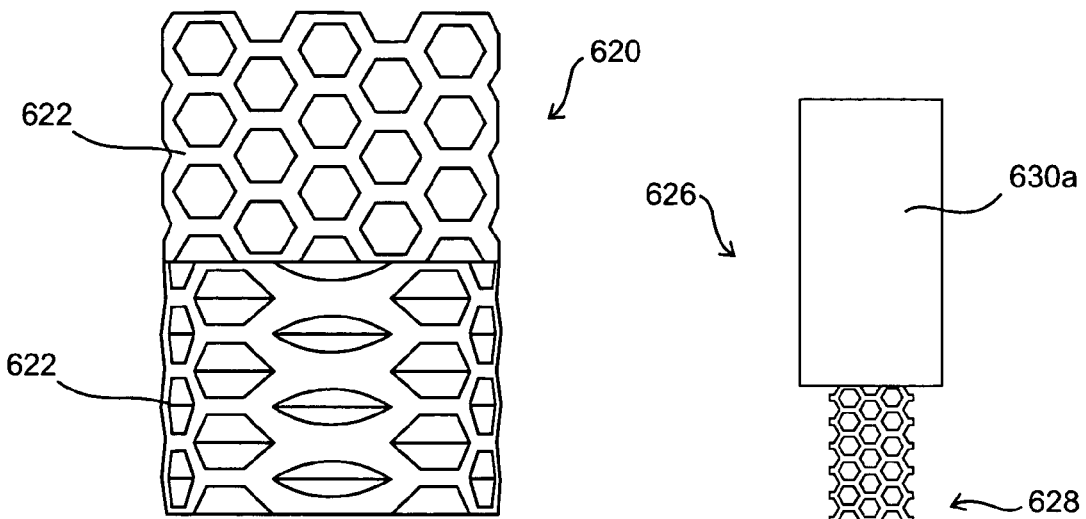
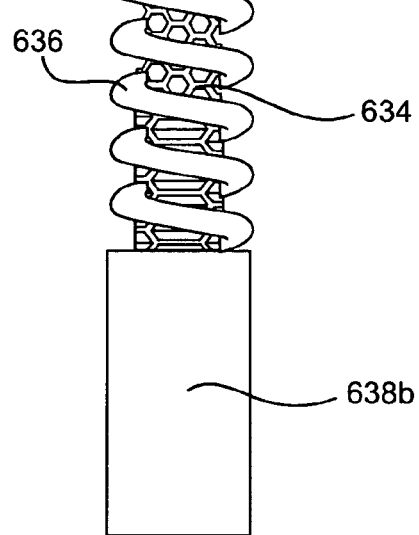
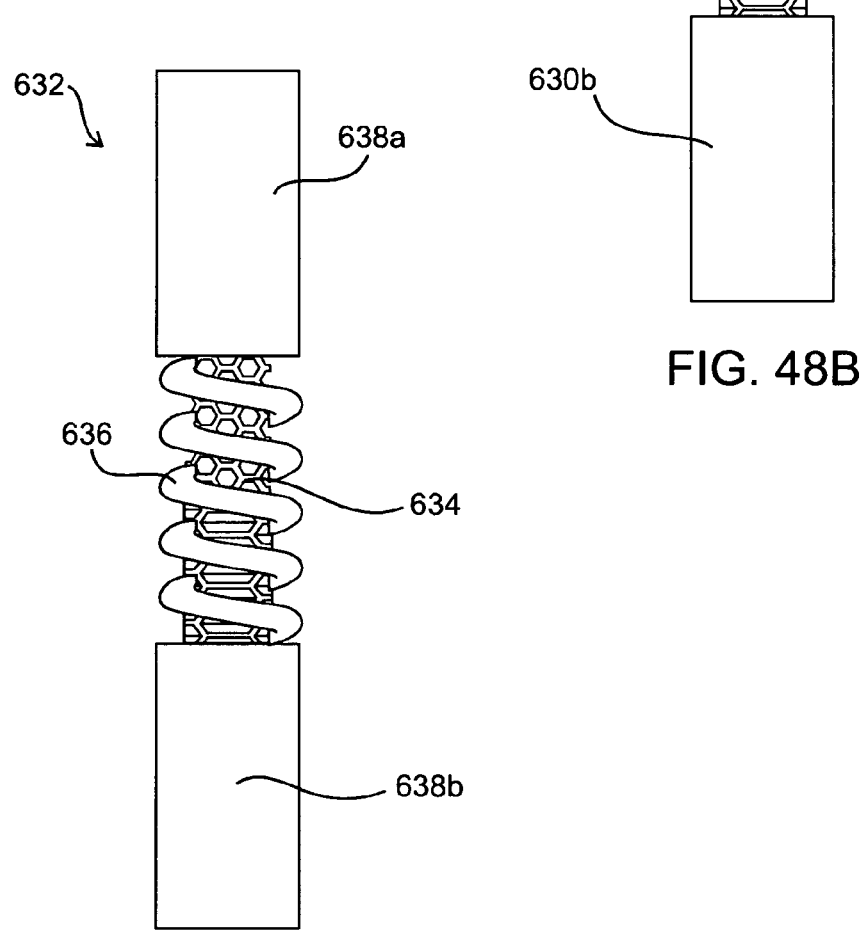
FIG. 48A
FIG. 48B
FIG. 48C

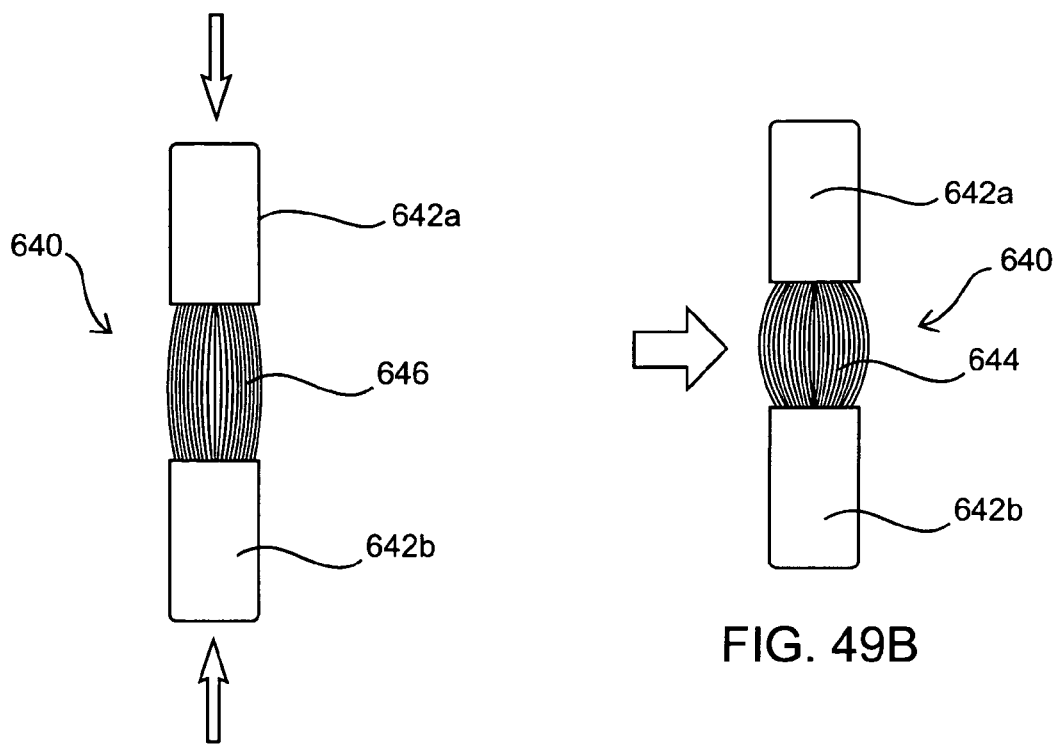
FIG. 49A
FIG. 49B
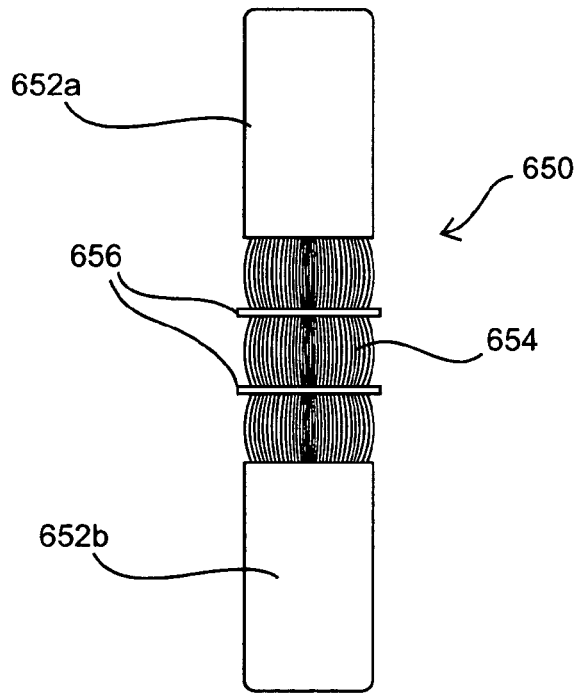
FIG. 50 ly, inferior
SYSTEMS AND METHODS FOR POSTERIOR DYNAMIC STABILIZATION OF THE SPINE

CROSS-REFERENCE TO RELATED APPLICATIONS

This application is a continuation-in-part of U.S. patent application Ser. No. 10/970,366, filed on Oct. 20, 2004, incorporated herein by reference.

FIELD OF THE INVENTION

The present invention is directed towards the treatment of spinal disorders and pain. More particularly, the present invention is directed to systems and methods of treating the spine, which eliminate pain and enable spinal motion, which effectively mimics that of a normally functioning spine.

BACKGROUND OF THE INVENTION

FIG. 1A illustrates a portion of the human spine having a superior vertebra 2 and an inferior vertebra 4, with an intervertebral disc 6 located in between the two vertebral bodies. The superior vertebra 2 has superior facet joints 8a and 8b, inferior facet joints 10a and 10b, posterior arch 16 and spinous process 18. Pedicles 3a and 3b interconnect the respective superior facet joints 8a, 8b to the vertebral body 2. Extending laterally from superior facet joints 8a, 8b are transverse processes 7a and 7b, respectively. Extending between each inferior facet joints 10a and 10b and the spinous process 18 are lamina 5a and 5b, respectively. Similarly, inferior vertebra 4 has superior facet joints 12a and 12b, superior pedicles 9a and 9b, transverse processes 11a and 11b, inferior facet joints 14a and 14b, lamina 15a and 15b, posterior arch 20, spinous process 22.

The superior vertebra with its inferior facets, the inferior vertebra with its superior facets, the intervertebral disc, and seven spinal ligaments (not shown) extending between the superior and inferior vertebrae together comprise a spinal motion segment or functional spine unit. Each spinal motion segment enables motion along three orthogonal axis, both in rotation and in translation. The various spinal motions are illustrated in FIGS. 2A-2C. In particular, FIG. 2A illustrates flexion and extension motions and axial loading, FIG. 2B illustrates lateral bending motion and FIG. 2C illustrated axial rotational motion. A normally functioning spinal motion segment provides physiological limits and stiffness in each rotational and translational direction to create a stable and strong column structure to support physiological loads.

Traumatic, inflammatory, metabolic, synovial, neoplastic and degenerative disorders of the spine can produce debilitating pain that can affect a spinal motion segment's ability to properly function. The specific location or source of spinal pain is most often an affected intervertebral disc or facet joint. Often, a disorder in one location or spinal component can lead to eventual deterioration or disorder, and ultimately, pain in the other.

Spine fusion (arthrodesis) is a procedure in which two or more adjacent vertebral bodies are fused together. It is one of the most common approaches to alleviating various types of spinal pain, particularly pain associated with one or more affected intervertebral discs. While spine fusion generally helps to eliminate certain types of pain, it has been shown to decrease function by limiting the range of motion for patients in flexion, extension, rotation and lateral bending. Furthermore, the fusion creates increased stresses on adjacent non-fused motion segments and accelerated degeneration of the motion segments. Additionally, pseudarthrosis (resulting from an incomplete or ineffective fusion) may not provide the expected pain-relief for the patient. Also, the device(s) used for fusion, whether artificial or biological, may migrate out of the fusion site creating significant new problems for the patient.

Various technologies and approaches have been developed to treat spinal pain without fusion in order to maintain or recreate the natural biomechanics of the spine. To this end, significant efforts are being made in the use of implantable artificial intervertebral discs. Artificial discs are intended to restore articulation between vertebral bodies so as to recreate the full range of motion normally allowed by the elastic properties of the natural disc. Unfortunately, the currently available artificial discs do not adequately address all of the mechanics of motion for the spinal column.

It has been found that the facet joints can also be a significant source of spinal disorders and debilitating pain. For example, a patient may suffer from arthritic facet joints, severe facet joint tropism, otherwise deformed facet joints, facet joint injuries, etc. These disorders lead to spinal stenosis, degenerative spondylolithesis, and/or isthmic spondylotlisthesis, pinching the nerves which extend between the affected vertebrae.

Current interventions for the treatment of facet joint disorders have not been found to provide completely successful results. Facetectomy (removal of the facet joints) may provide some pain relief; but as the facet joints help to support axial, torsional, and shear loads that act on the spinal column in addition to providing a sliding articulation and mechanism for load transmission, their removal inhibits natural spinal function. Laminectomy (removal of the lamina, including the spinal arch and the spinous process) may also provide pain relief associated with facet joint disorders; however, the spine is made less stable and subject to hypermobility. Problems with the facet joints can also complicate treatments associated with other portions of the spine. In fact, contraindications for disc replacement include arthritic facet joints, absent facet joints, severe facet joint tropism, or otherwise deformed facet joints due to the inability of the artificial disc (when used with compromised or missing facet joints) to properly restore the natural biomechanics of the spinal motion segment.

While various attempts have been made at facet joint replacement, they have been inadequate. This is due to the fact that prosthetic facet joints preserve existing bony structures and therefore do not address pathologies which affect facet joints themselves. Certain facet joint prostheses, such as those disclosed in U.S. Pat. No. 6,132,464, are intended to be supported on the lamina or the posterior arch. As the lamina is a very complex and highly variable anatomical structure, it is very difficult to design a prosthesis that provides reproducible positioning against the lamina to correctly locate the prosthetic facet joints. In addition, when facet joint replacement involves complete removal and replacement of the natural facet joint, as disclosed in U.S. Pat. No. 6,579,319, the prosthesis is unlikely to endure the loads and cycling experienced by the vertebra. Thus, the facet joint replacement may be subject to long-term displacement. Furthermore, when facet joint disorders are accompanied by disease or trauma to other structures of a vertebra (such as the lamina, spinous process, and/or transverse processes) facet joint replacement is insufficient to treat the problem(s).

Most recently, surgical-based technologies, referred to as "dynamic posterior stabilization," have been developed to address spinal pain resulting from more than one disorder, when more than one structure of the spine have been compromised. An objective of such technologies is to provide the support of fusion-based implants while maximizing the natural biomechanics of the spine. Dynamic posterior stabilization systems typically fall into one of two general categories: (1) interspinous spacers and (2) posterior pedicle screw-based systems.

Examples of interspinous spacers are disclosed in U.S. Pat. No. Re. 36,211, U.S. Pat. Nos. 5,645,599, 6,695,842, 6,716,245 and 6,761,720. The spacers, which are made of either a hard or compliant material, are placed between adjacent spinous processes. Because the interspinous spacers involve attachment to the spinous processes, use of these types of systems is limited to applications where the spinous processes are uncompromised and healthy.

Examples of pedicle screw-based systems are disclosed in U.S. Pat. Nos. 5,015,247, 5,484,437, 5,489,308, 5,609,636 and 5,658,337, 5,741,253, 6,080,155, 6,096,038, 6,264,656 and 6,270,498. These types of systems involve the use of screws which are positioned in the vertebral body through the pedicle. Certain types of these pedicle screw-based systems may be used to augment compromised facet joints, while others require removal of the spinous process and/or the facet joints for implantation. One such system, the Zimmer Spine Dynesys® employs a cord which is extended between the pedicle screws and a fairly rigid spacer which is passed over the cord and positioned between the screws. While this system is able to provide load sharing and restoration of disc height, because it is so rigid, it does not effective in preserving the natural motion of the spinal segment into which it is implanted. Other pedicle screw-based systems employ articulating joints between the pedicle screws.

With the limitations of current spine stabilization technologies, there is clearly a need for an improved means and method for dynamic posterior stabilization of the spine which address the drawbacks of prior devices. In particular, it would be highly beneficial to have a dynamic stabilization system that enables the spine to mimic the motion of one or more healthy, uncompromised vertebral segments without limiting natural extension/flexion and lateral bending movement. It would be additionally beneficial if such a system could be used to treat all spinal indications regardless of pain source, prevent or slow the deterioration of the intervertebral discs, and be used in conjunction with prosthetic intervertebral discs.

SUMMARY OF THE INVENTION

The present invention provides methods, systems and devices for dynamically stabilizing the spine are provided. The systems include a superior component for attachment to a superior vertebra of a spinal motion segment and an inferior component for attachment to an inferior vertebra of a spinal motion segment. The interconnection between the two components enables the spinal motion segment to move in a manner that mimics the natural motion of the spinal motion segment. In various embodiments, the superior and/or inferior components includes a strut member for interfacing or adjustably interconnecting between the two components wherein forward translation of the superior vertebra relative to the inferior vertebra is prevented. In certain embodiments, the strut or struts include at least one joint which may be compressible and/or distractable. In other embodiments, the length, stiffness or shape of the strut may be adjustable. The systems may be configured to include additional components for the treatment of more than one spinal segment. Moreover, they may be configured for implantation without the removal of any portion of the spinal motion segment. Still yet, certain of the systems include a prosthetic intervertebral disk member interconnected to the strut.

The present invention also includes methods for stabilizing at least one spinal motion segment where the methods involve implantation of the subject systems. Implantation of the systems usually requires the use of one or more pedicle screws for attaching the components to the vertebrae. Certain of the implantation methods may be performed without resecting any portion of the spinal motion segment.

These and other objects, advantages, and features of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIGS. 18A and 18B illustrate uncompressed and compressed states of the strut, ligament or band of the system of FIGS. 17A and 17B.

FIGS. 19A, 19B and 19C illustrate various states of another embodiment of a strut, ligament or band usable with the system of FIGS. 17A and 17B.

FIGS. 24A and 24B illustrate dorsal views of the system of FIG. 23A in flexion and extension motion, respectively.

FIGS. 27A, 27B, 27C and 27D illustrate the joint of FIG. 25C in flexion, extension, and left and right lateral bending motions, respectively.

FIGS. 35A and 35B illustrate an embodiment of a pedicle screw usable with the systems of the present invention.

FIGS. 45A and 45B illustrate a multilevel embodiment of the strut of FIGS. 43A and 43B and FIGS. 44A-44D.

FIGS. 46A and 46B illustrate another embodiment of an interconnecting member of the present invention.

FIG. 48A illustrates another material having another honeycomb configuration suitable for use with an interconnecting member of the present invention. FIGS. 48B and 48C illustrate interconnecting members employing the material of FIG. 48A.

FIGS. 49A and 49B illustrate another embodiment of an interconnecting member of the present invention utilizing a fiber structure.

FIG. 50 illustrates another embodiment of an interconnecting member of the present invention utilizing a fiber structure.

DETAILED DESCRIPTION OF THE INVENTION

Before the subject devices, systems and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs.

It must be noted that as used herein and in the appended claims, the singular forms "a", "an", and "the" include plural referents unless the context clearly dictates otherwise. Thus, for example, reference to "a spinal segment" may include a plurality of such spinal segments and reference to "the screw" includes reference to one or more screws and equivalents thereof known to those skilled in the art, and so forth.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Figure 1A:
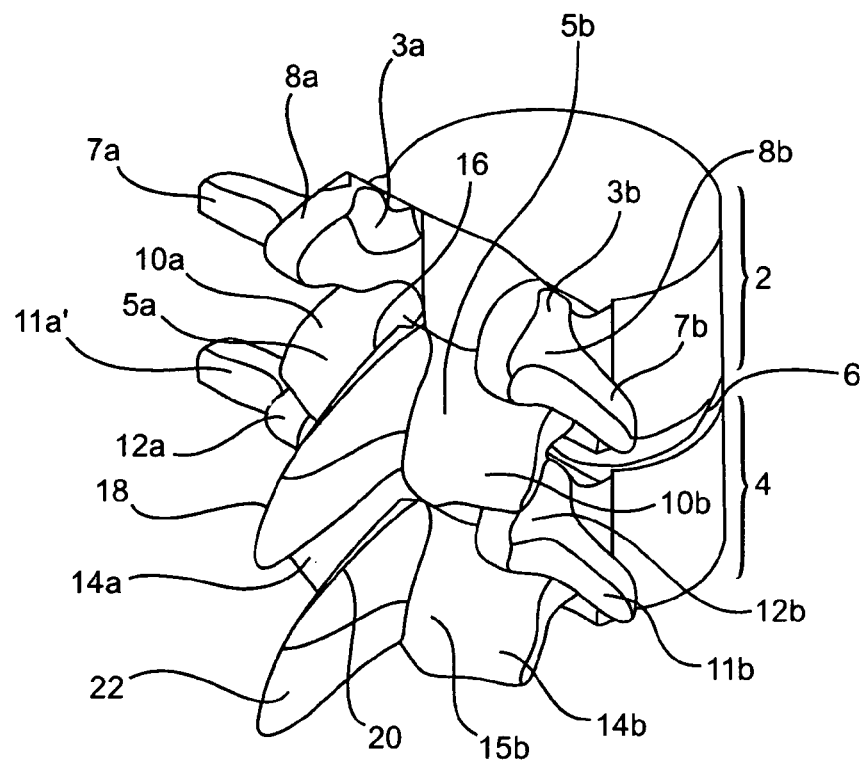
FIGS. 1A and 1B illustrate perspective views of a portion of the human spine having two vertebral segments, where the spinous process and the lamina of the superior vertebra have been resected in FIG. 1B.
Figure 1B:
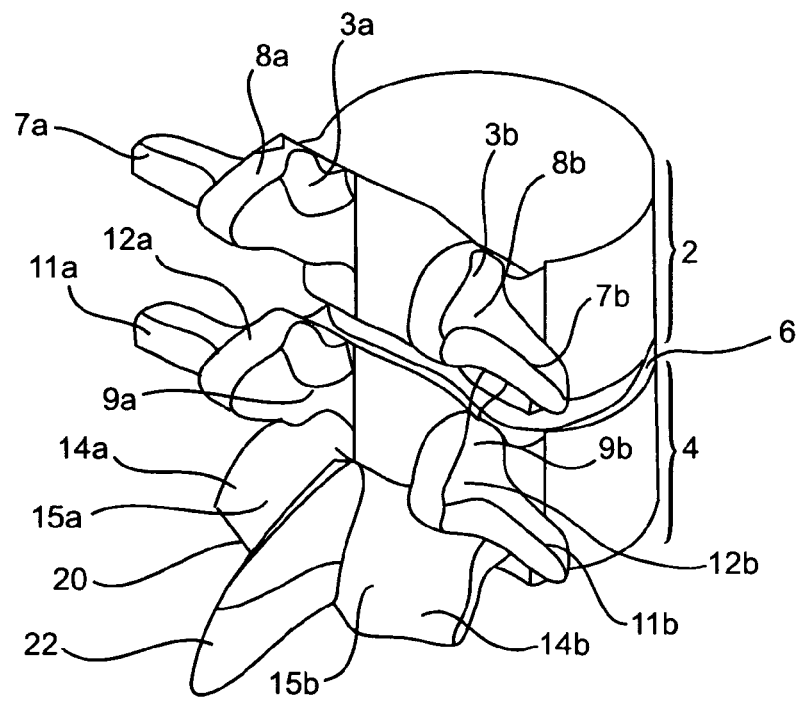
Figure 2A:
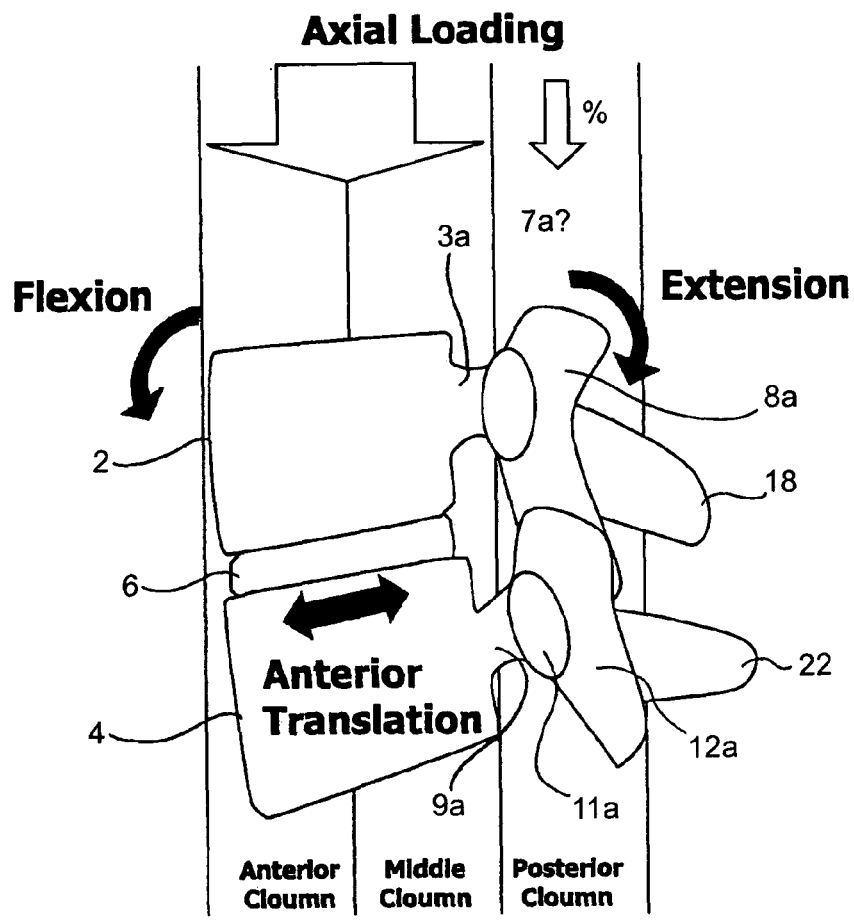
FIGS. 2A, 2B and 2C illustrate left side, dorsal and top views, respectively, of the spinal segments of FIG. 1A under going various motions.
Figure 2B:
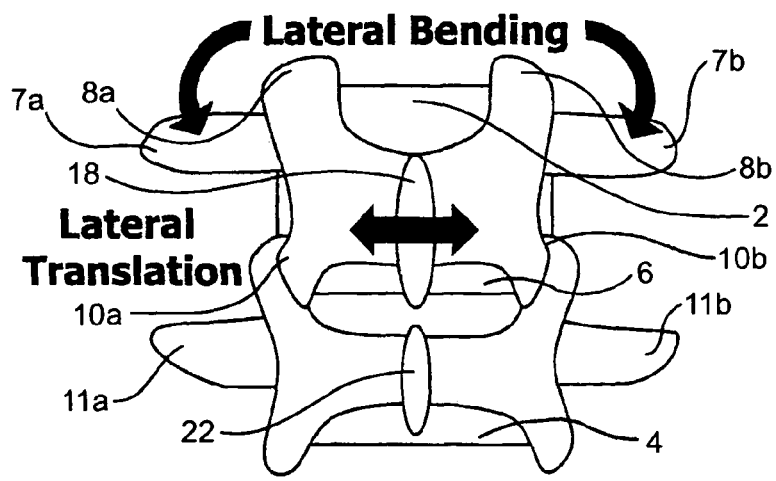
Figure 2C:
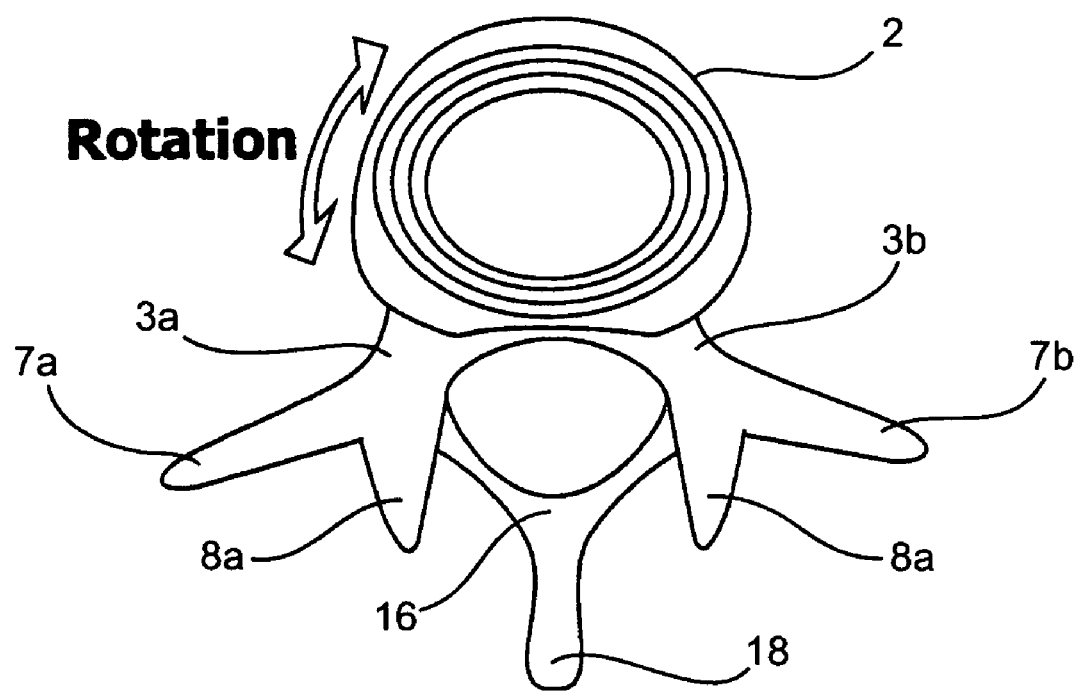

The present invention will now be described in greater detail by way of the following description of exemplary embodiments and variations of the systems and methods of the present invention. While more fully described in the context of the description of the subject methods of implanting the subject systems, it should be initially noted that in certain applications where the natural facet joints are compromised, as illustrated in FIG. 1B, inferior facets 10*a* and 10*b*, lamina 5*a* and 5*b*, posterior arch 16 and spinous process 18 of superior vertebra 2 of FIG. 1A may be resected for purposes of implantation of certain of the dynamic stabilization systems of the present invention. In other applications, where possible, the natural facet joints, lamina and/or spinous are spared and left intact for implantation of other dynamic stabilization systems of the present invention.

It should also be understood that the term "system", when referring to a system of the present invention, most typically refers to a set of components which includes a superior, cephalad or rostral (towards the head) component configured for implantation into a superior vertebra of a vertebral motion segment and an inferior or caudal (towards the feet) component configured for implantation into an inferior vertebra of a vertebral motion segment. A pair of such component sets includes one set of components configured for implantation into and stabilization of the left side of a vertebral segment and another set configured for the implantation into and stabilization of the right side of a vertebral segment. Where multiple spinal segments or units are being treated, the term "system" may refer to two or more pairs of component sets, i.e., two or more left sets and/or two or more right sets of components. Such a multilevel system involves stacking of component sets in which each set includes a superior component, an inferior component, and one or more medial components therebetween.

The superior and inferior components (and any medial components therebetween), when operatively implanted, are engaged or interface with each other in a manner that enables the treated spinal motion segment to mimic the function and movement of a healthy segment. The interconnecting or interface means include one or more structures or members which enables, limits and/or otherwise selectively controls spinal motion. The structures may perform such functions by exerting various forces on the system components, and thus on the target vertebrae. The manner of coupling, interfacing, engagement or interconnection between the subject system components may involve compression, distraction, rotation or torsion, or a combination thereof. In certain embodiments, the extent or degree of these forces or motions between the components may be intraoperatively selected and/or adjusted to address the condition being treated, to accommodate the particular spinal anatomy into which the system is implanted, and to achieve the desired therapeutic result.

In certain embodiments, the superior and inferior components are mechanically coupled to each other by one or more interconnection or interfacing means. In other embodiments, the superior and inferior components interface in an engaging manner which does not necessary mechanically coupled or fixed the components together but rather constrains their relative movement and also enables the treated spinal motion segment to mimic the function and movement of a healthy segment. Typically, the interconnecting means is a dorsally positioned component, i.e., positioned posteriorly of the superior and inferior components, or may be a laterally positioned component, i.e., positioned to the outer side of the posterior and inferior components. The structures may involve one or more struts and/or joints which provide for stabilized spinal motion. The various system embodiments may further include a band, interchangeably referred to as a ligament, which provides a tensioned relationship between the superior and inferior components and helps to maintain the proper relationship between the components.

Figure 3A:
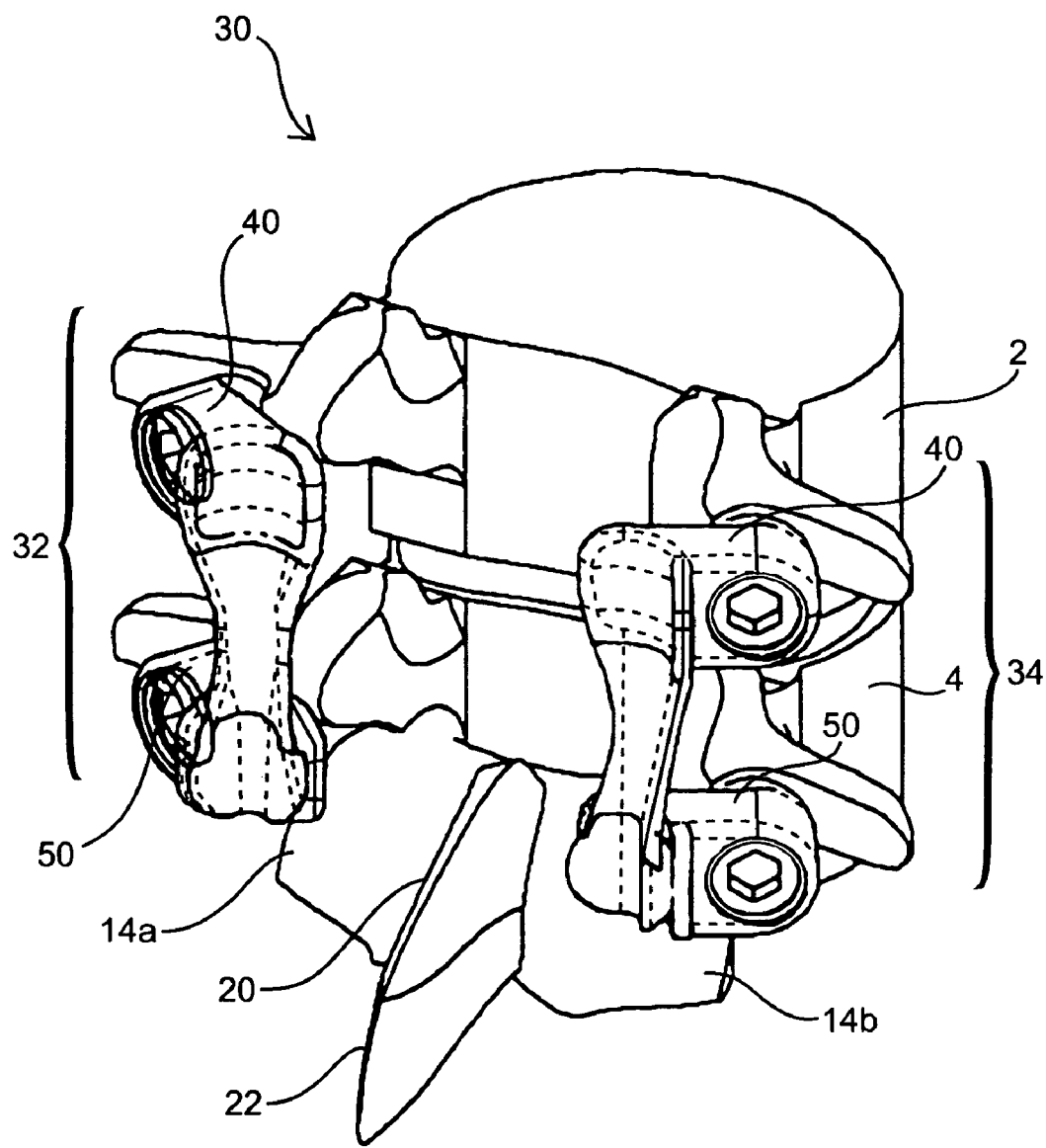
FIGS. 3A, 3B and 3C illustrate perspective, dorsal and top views, respectively, of one embodiment of a dynamic stabilization system of the present invention implanted in the vertebral segments of FIG. 1B.
Figure 3B:
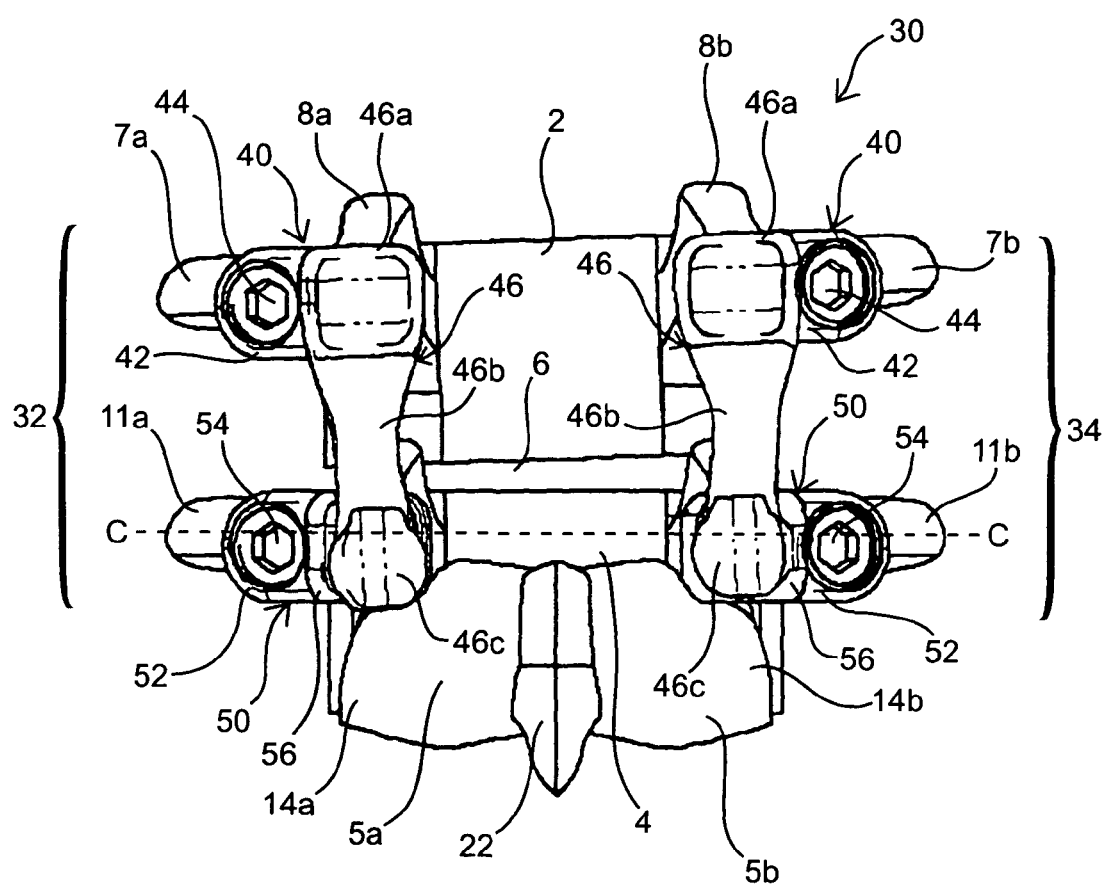
Figure 3C:
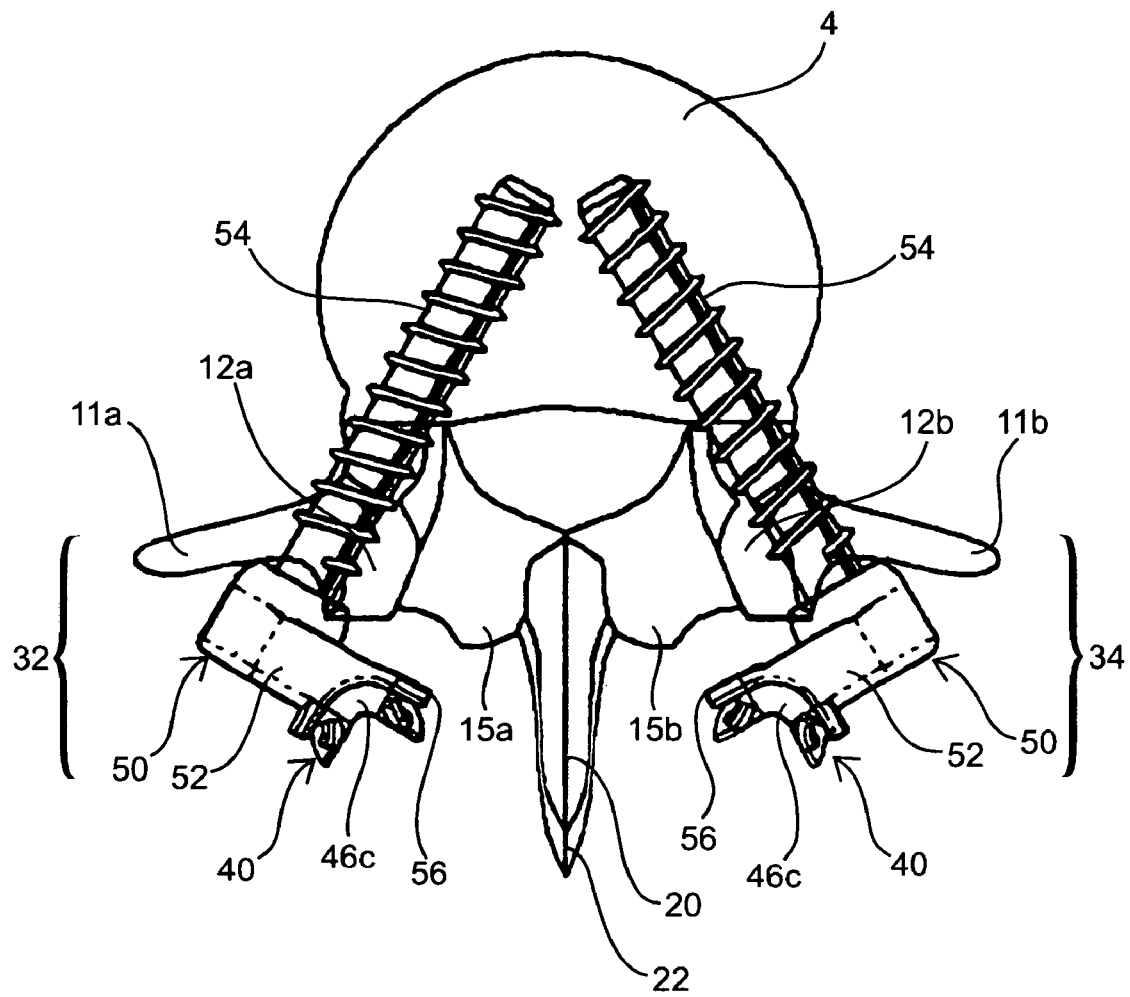
Figure 4A:
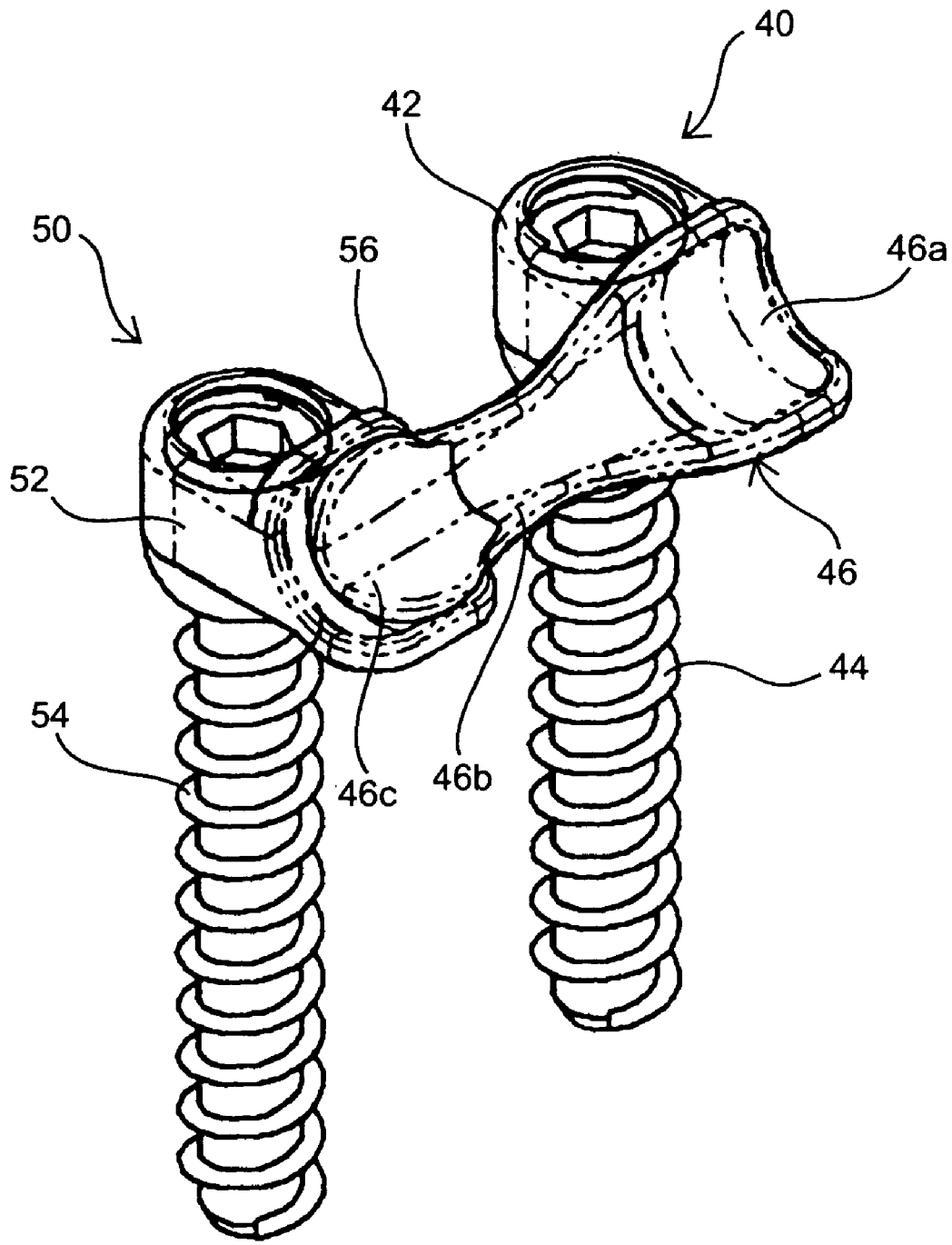
FIGS. 4A and 4B are perspective and side views, respectively, of the left side of the system of FIGS. 3A-3C.
Figure 4B:
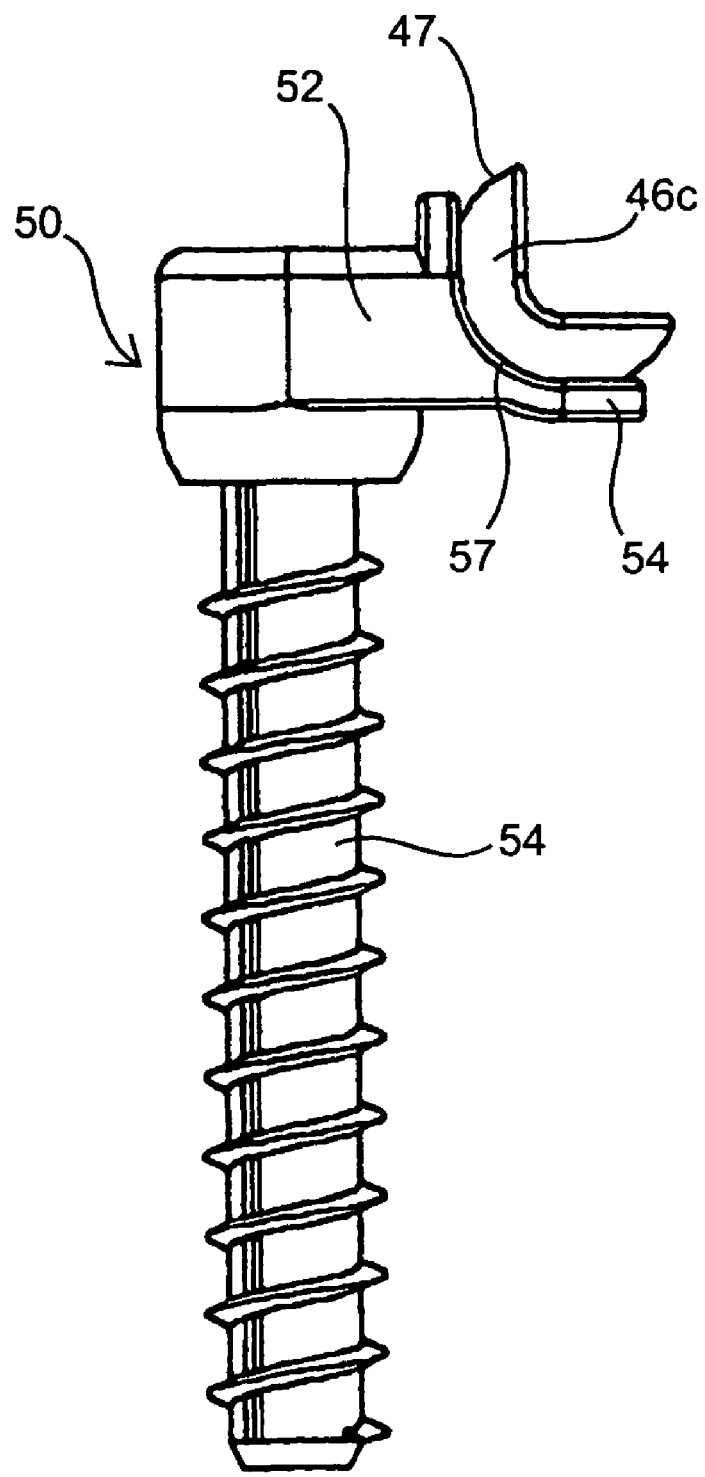

Referring now to FIGS. 3A-3C, there is illustrated a dynamic stabilization system 30 operatively implanted into the vertebral segment of FIG. 1B and having left and right sets 32, 34 of stabilization components where each set includes a superior portion or component 40 and an inferior portion or component 50. As further illustrated in FIGS. 4A and 4B, superior component 40 includes a base member 42 configured for receiving a screw 44 and having an anterior portion having a surface (that surface facing in the anterior direction of the spine) for placement against a portion of the superior pedicle of vertebra 2. Extending medially from screw 44 and downward and substantially transverse to base 42 is a post, stem or strut 46. Stem 46 includes a proximal portion 46*a*, an elongated central portion 46*b* and a distal portion 46*c*. Inferior component 50 includes a base member 52 similarly configured to base member 42 of superior portion 40 for receiving a screw 54 and having an anterior portion having a surface (that surface facing in the anterior direction of the spine) for placement against a portion of the superior pedicle of vertebra 4. Extending medially of screw 54, base 52 is configured to receive and engage with distal portion 46*c* of superior portion 40. The stem receiving portion 56 of inferior component 50 and stem distal portion 46*c* are mutually configured to engage with each other in a manner that allows flexion, extension, axial rotation and lateral bending motions which mimic that of the natural spine segment, while preventing or limiting anterior and lateral translation of vertebrae 2 and 4 relative to each other.

Certain disorders of the spine, such as isthmic spondylolisthesis, destabilize the spine to where there is undesirable anterior translation of a superior vertebra relative to an inferior vertebra. The positioning and engagement of the superior component relative to the inferior component, and particularly of the positioning of the strut relative to engaging portion of the inferior component, helps to prevent such undesirable anterior or forward translation of the superior vertebra. In particular, the abutment of the distal portion of the strut against the surface of the engagement portion of the inferior component resists, and may partially or completely prevent, the forward or anterior translational motion of the superior vertebra relative to the inferior vertebra.

Figure 7A:
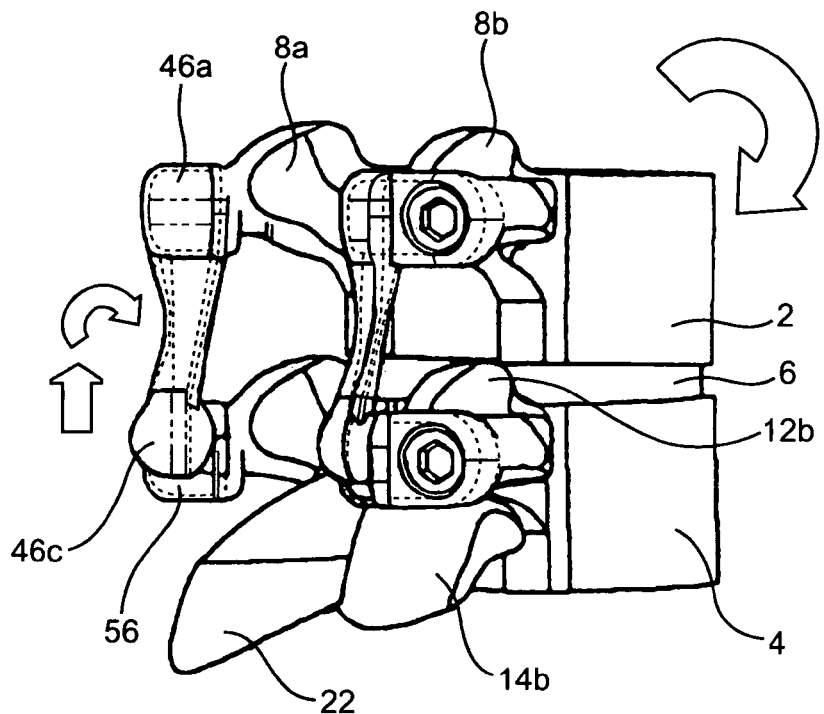
FIGS. 7A, 7B, 7C and 7D illustrate the systems of FIGS. 3-5 undergoing flexion, extension, left lateral pending and right lateral bending motions, respectively.
Figure 7B:
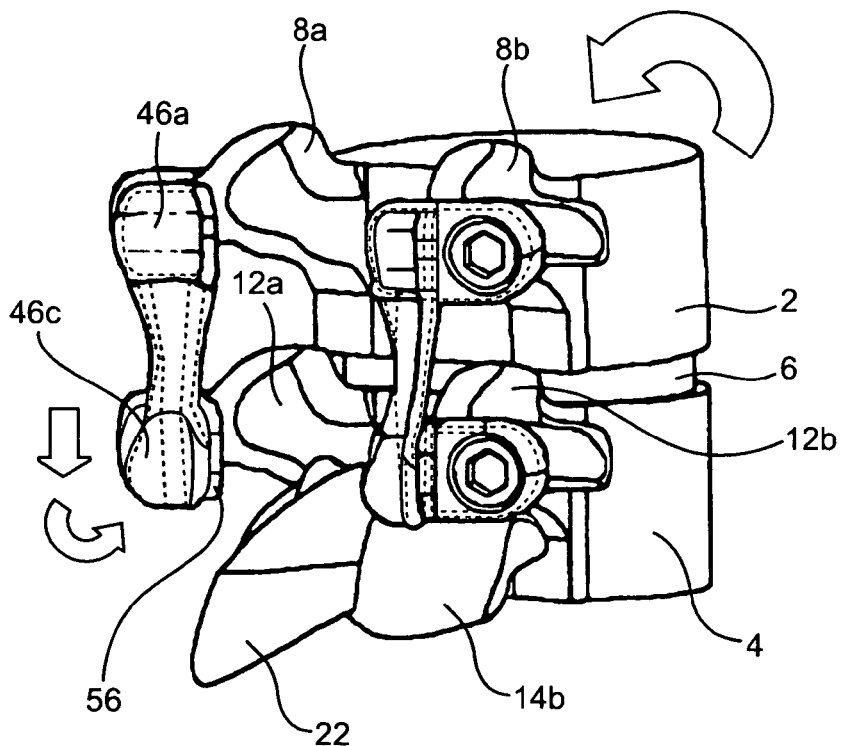
Figure 7C:
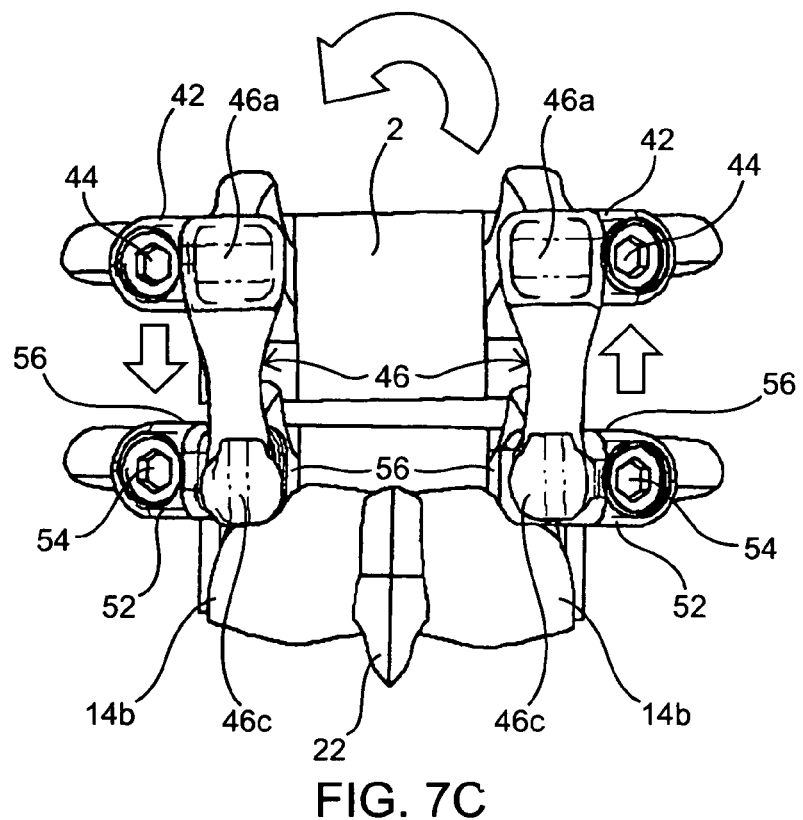
Figure 7D:
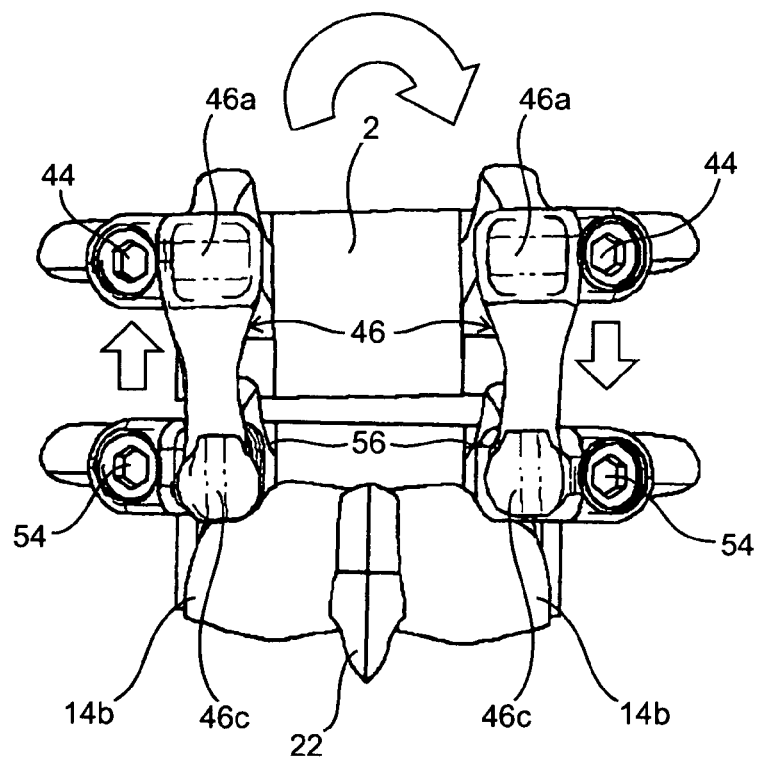

The effects of flexion, extension, and left and right lateral bending motions on the implanted system of FIGS. 3A-3C are graphically illustrated in FIGS. 7A-7C, respectively. Flexion of the spine, as illustrated in FIG. 7A, results in slightly upward and forward rotational movement of distal strut portion 46c, while the relative positioning or juxtaposition of the superior component 40 and inferior component 50 is such that the engaging or mating surfaces of distal strut portion 46c and engaging portion 56 preferably maintain contact throughout the motion. This is also the case during extension of the spine, as illustrated in FIG. 7B, which results in a slightly downward and forward rotational movement of distal port portion 46c. Still yet, contact is maintained between the components during lateral bending, as illustrated in FIGS. 7C and 7D, where there is translation movement of the respective posts along the y-axis with minimal or no rotational movement of the posts. As such, the subject systems enable or mimic the motion of the natural spine segment while preventing or limiting anterior and lateral translation of vertebrae 2 and 4 relative to each other.

Figure 6A:
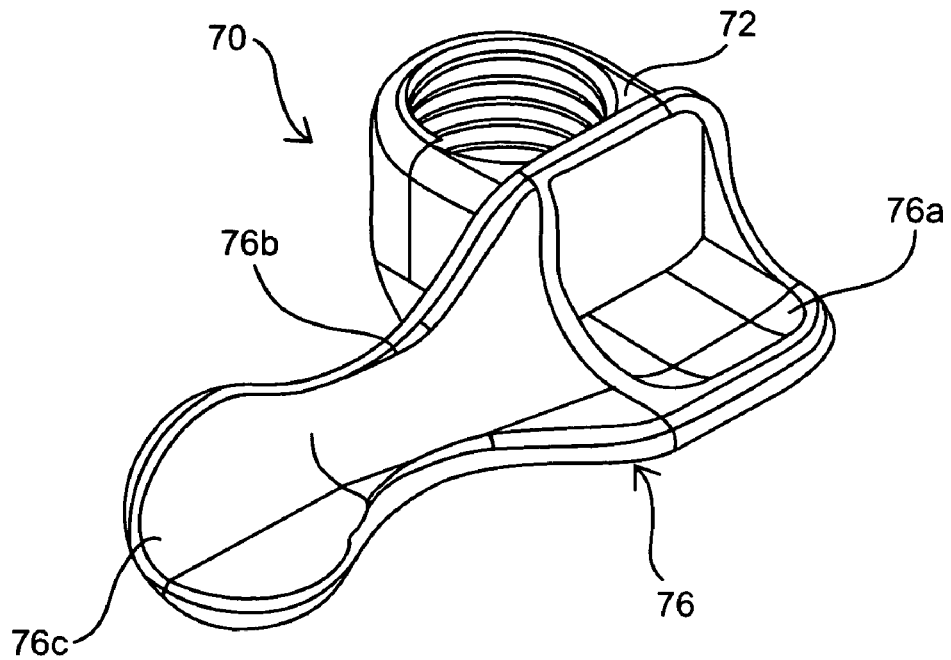
FIGS. 6A and 6B illustrate another embodiment of superior component of the systems of FIGS. 3-5.
Figure 6B:
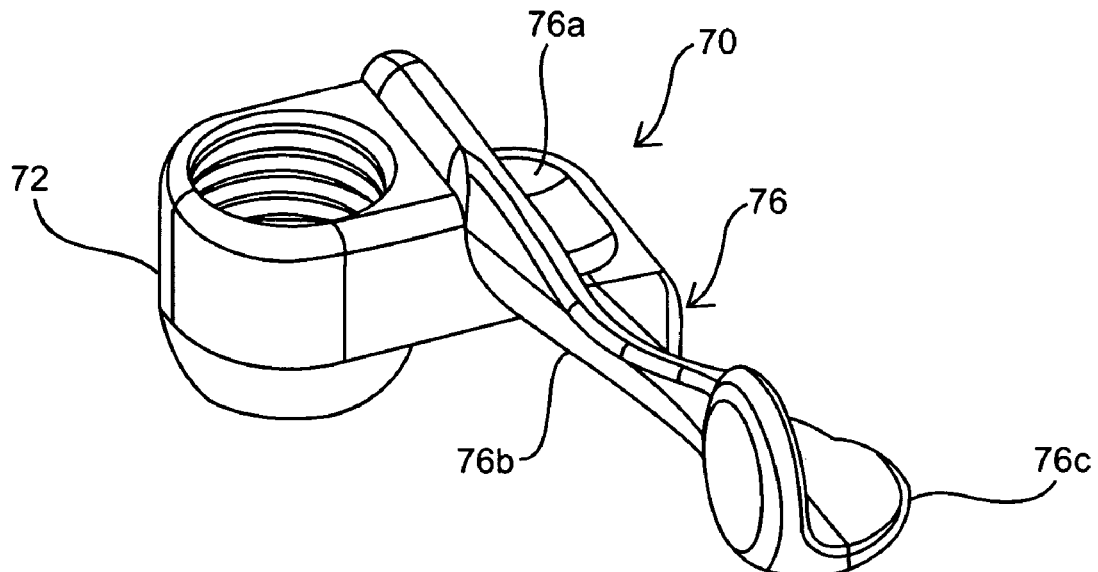

Additionally, the mating surfaces of the distal strut and the engaging portion of the inferior component may be selectively configured to control the amount of axial rotational movement. Where the engaging surfaces are more spherical or rounded, greater axial rotation is permitted between the two; however, where the engaging surfaces are more angular, axial rotation and lateral bending may be semi-constrained or completely constrained. For example, in the embodiment of FIGS. 3A-3C, stem distal portion 46c and inferior engaging portion 56 have a modified or open ball-and-socket configuration. More specifically, as best seen in the cross-sectional views of FIG. 4B and of FIG. 3C (the latter taken through line C-C of FIG. 3B), distal portion 46c has an outer convex surface 47 and engaging portion 56 has an inner concave surface 57 for mating engagement with each other. Alternatively, as illustrated in FIGS. 6A and 6B, the superior component 70 has a base portion 72 and a strut 76 extending therefrom and having proximal and distal strut end portions 76a and 76c, respectively, having convex and concave mating surfaces which are more angular or flattened.

Figure 5:
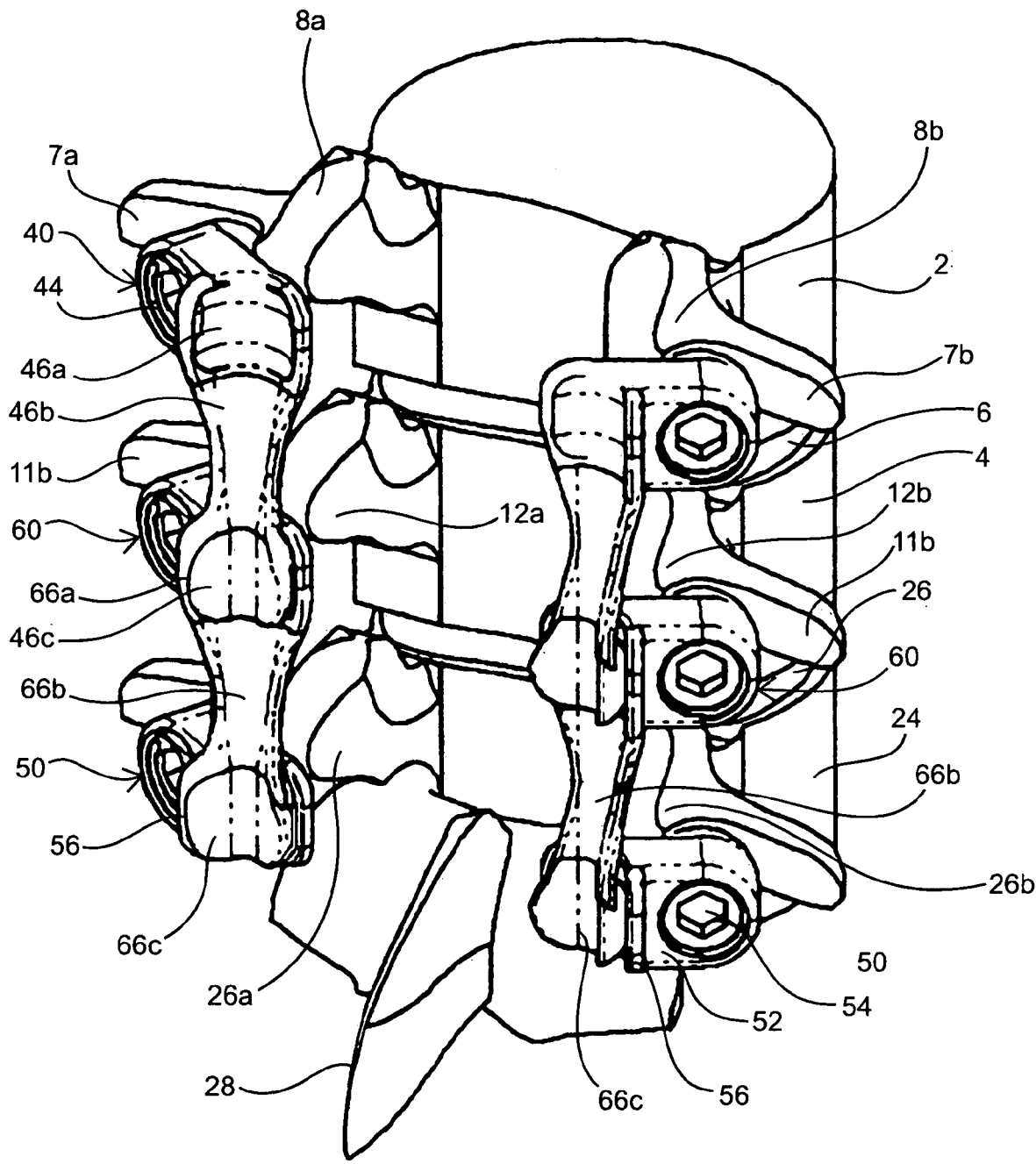
FIG. 5 illustrates the system of FIGS. 3A-3C in a multi-segment application.

As mentioned above, any number of sets of stabilization components of the present invention may be employed as necessary for treating back pain. For example, where two adjacent spine segments or units are affected, a stacked version of the above-described stabilization system may be employed. As illustrated in FIG. 5, a portion of the spine including vertebrae 2 and 4 and a third vertebra 24 situated immediately inferior to vertebra 4, in between which is intervertebral disc 26, is stabilized with such a stacked system. Here, left and right superior and inferior components, 40, 50 are identical to that of the system of FIGS. 3A-3C, however, an additional median component 60 is provided implanted on a vertebra positioned between the two. As such, superior and median components 40 and 60 each have a stem extending from the base member 42, 62 respectively. Distal stem portion 66c is similarly configured to distal portion 46c to engage with an engaging portion 56 of inferior component 50 which does not include a stem.

It should be noted that while the most inferior of the components of the subject systems are illustrated having a configuration different from that of all of the other (superior or median) components, all of the components may have identical configurations such that the proximal portion of the stem is configured to engage the distal portion of the stem of an adjacent superior component and visa versa. As such, the distal portion of the stem of the most inferiorly implanted component is not in contact with another system component (i.e., it is not operatively used). However, so as to minimize the bulk of the system and to prevent inadvertent interference of spinal motion, the most inferior of the components implanted preferably does not have a stem. Similarly, the most superiorly positioned of the implanted components, e.g., superior component 40, need not have a proximal portion 46a configured for engaging a distal stem portion.

Figure 8:
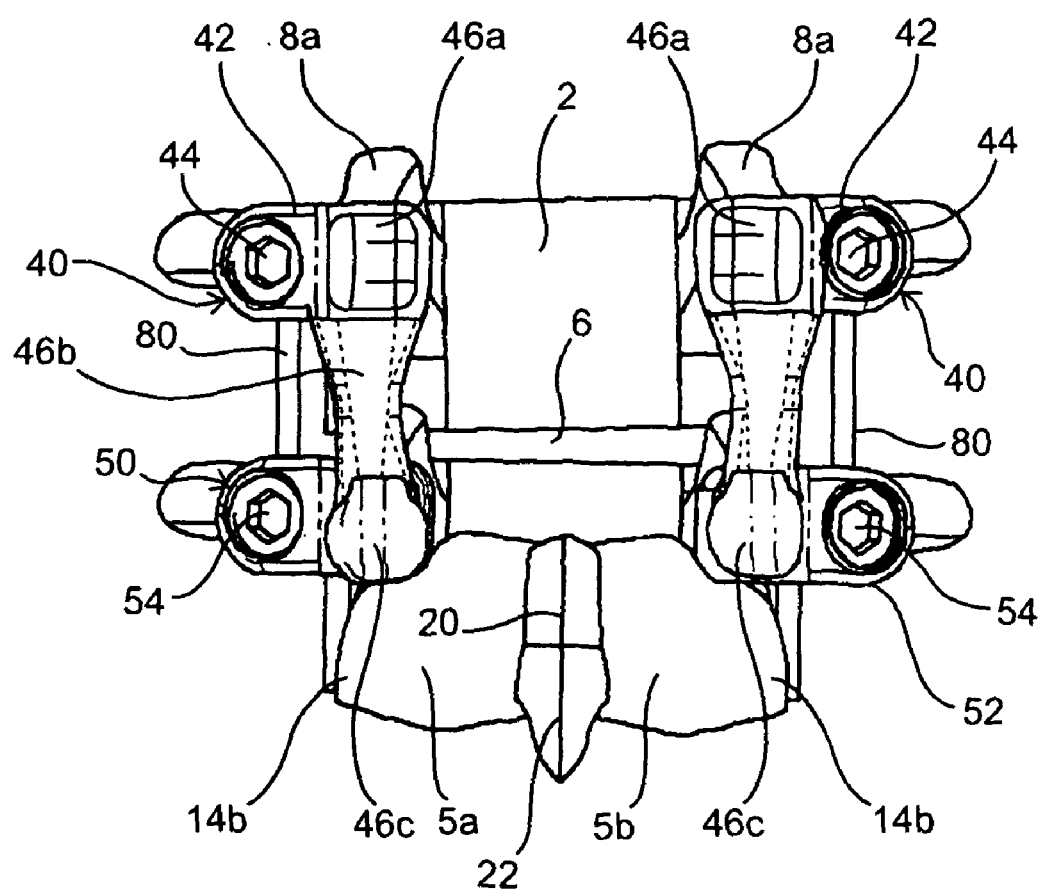
FIG. 8 illustrates a dorsal view of another embodiment of a dynamic stabilization system of the present invention implanted in the vertebral segments of FIG. 1B, where the system employs a ligament component.
Figure 9:
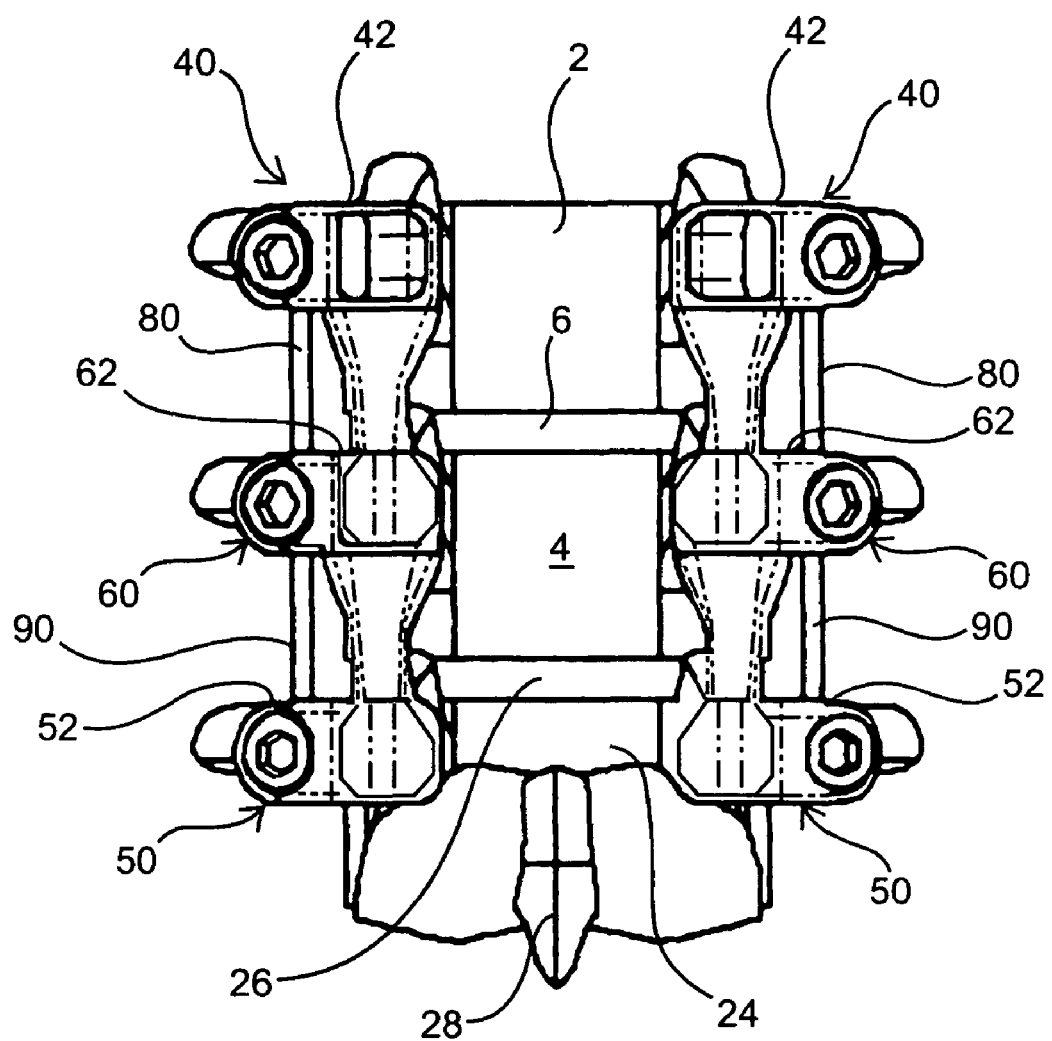
FIG. 9 illustrates the system of FIG. 8 in a multi-segment application.

Referring now to FIGS. 8 and 9, there is illustrated single-segment and multi-segment embodiments, respectively, of another system of the present invention. The system of FIG. 8 includes left and right sets of superior component 40 and inferior component 50 as described above with respect to the embodiment of FIGS. 3 and 4. However, this embodiment further includes a ligament member or tension band 80 extending substantially vertical between base portions 42 and 52, respectively, of the superior and inferior components 40 and 50, and substantially parallel to stem 46 of superior component 40. The multi-segment system of FIG. 9 includes left and right sets of superior component 40, inferior component 50 and an additional median component 60, as described above with respect to the embodiment of FIG. 5. As with the single segment configuration of FIG. 8, this system further includes ligament members 80 and 90, the former extending substantially vertically between the base portions 42 and 62 of superior and median components 40 and 60, respectively, and the latter extending substantially vertically between base portions 62 and 52 of the median and inferior components 60 and 50, respectively. Each ligament member is substantially parallel to the corresponding strut of the same component.

Figure 10A:
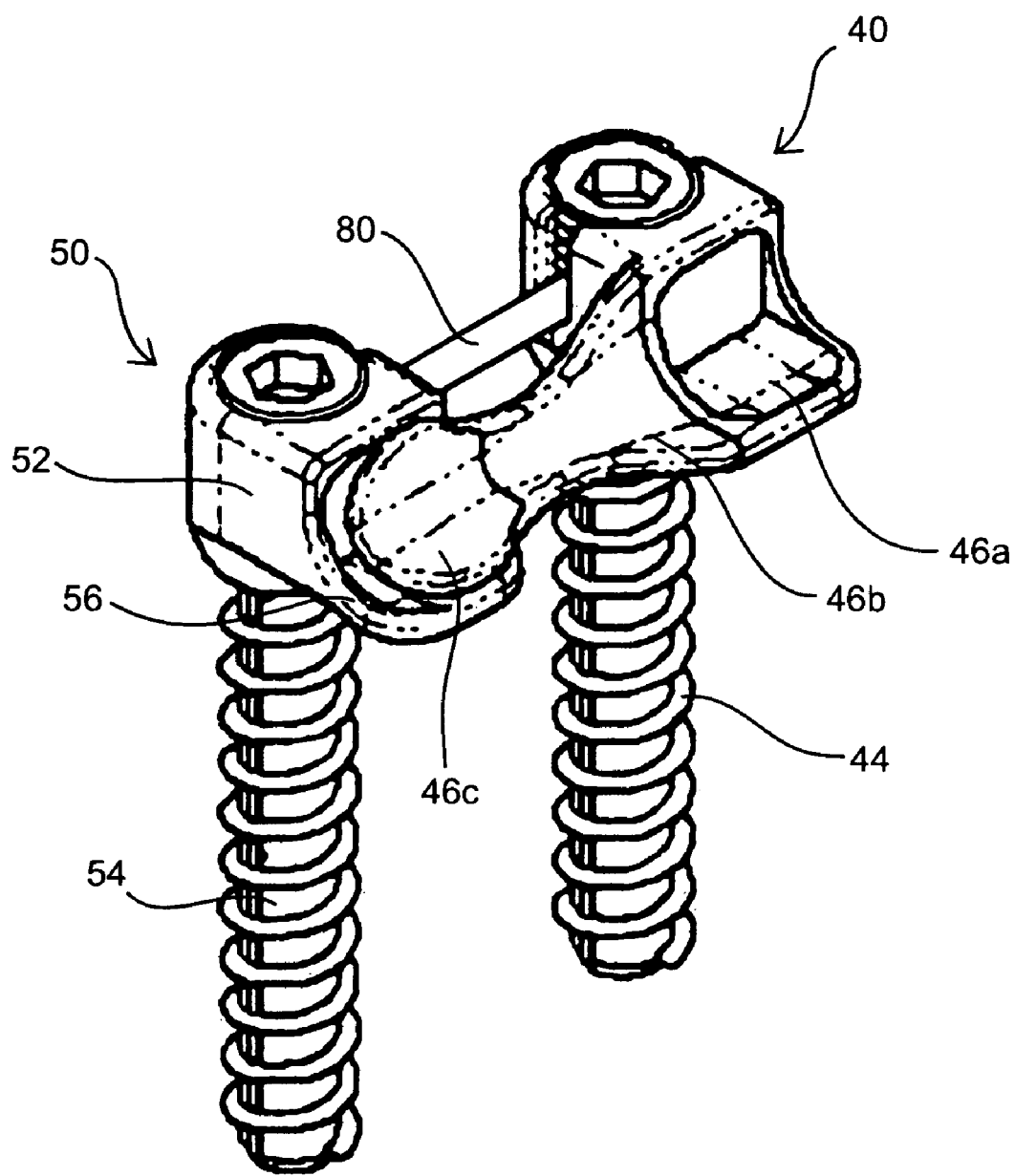
FIGS. 10A, 10B and 10C are perspective, exploded and top views, respectively, of the left side of the system of FIGS. 8 and 9.
Figure 10B:
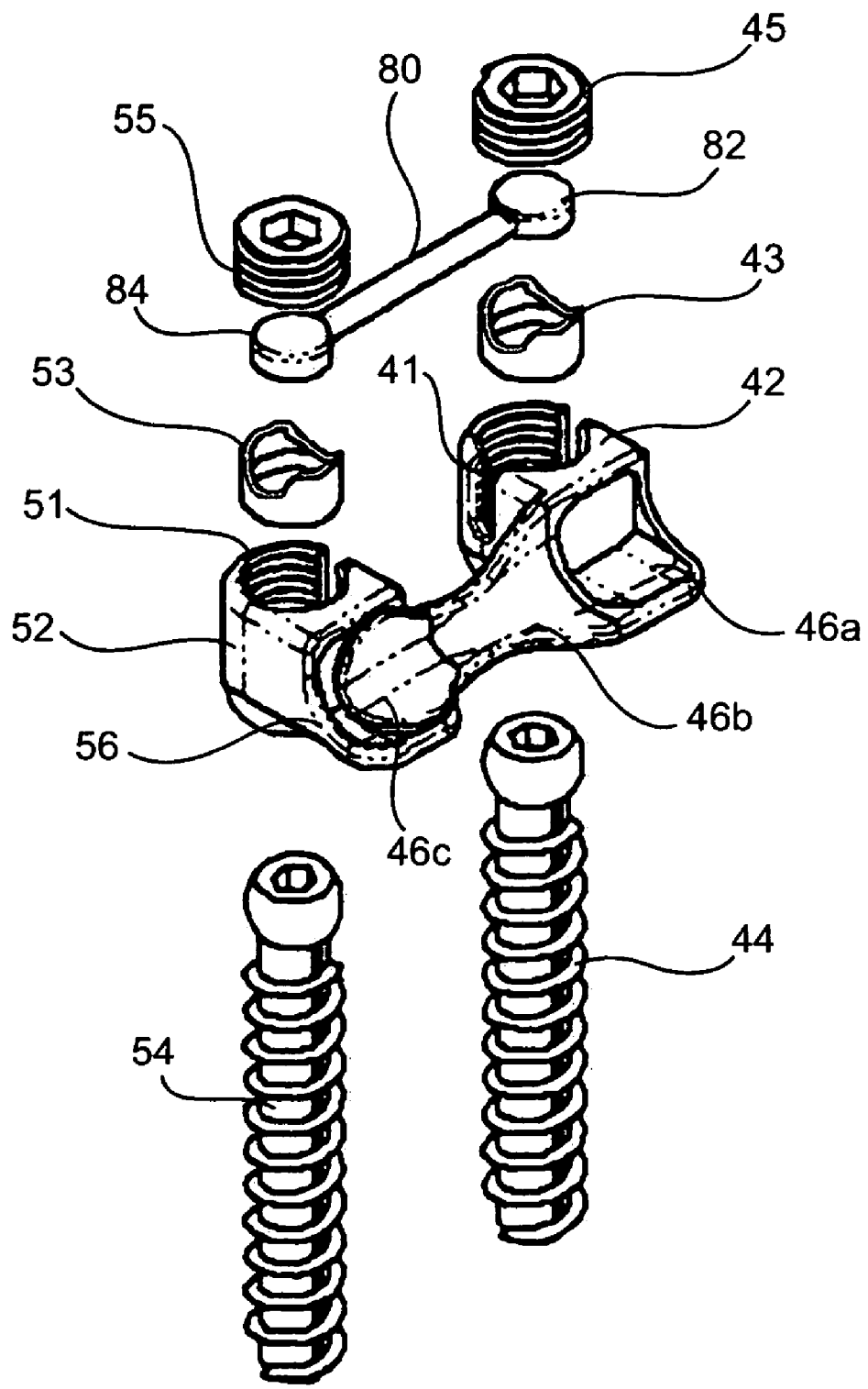
Figure 10C:
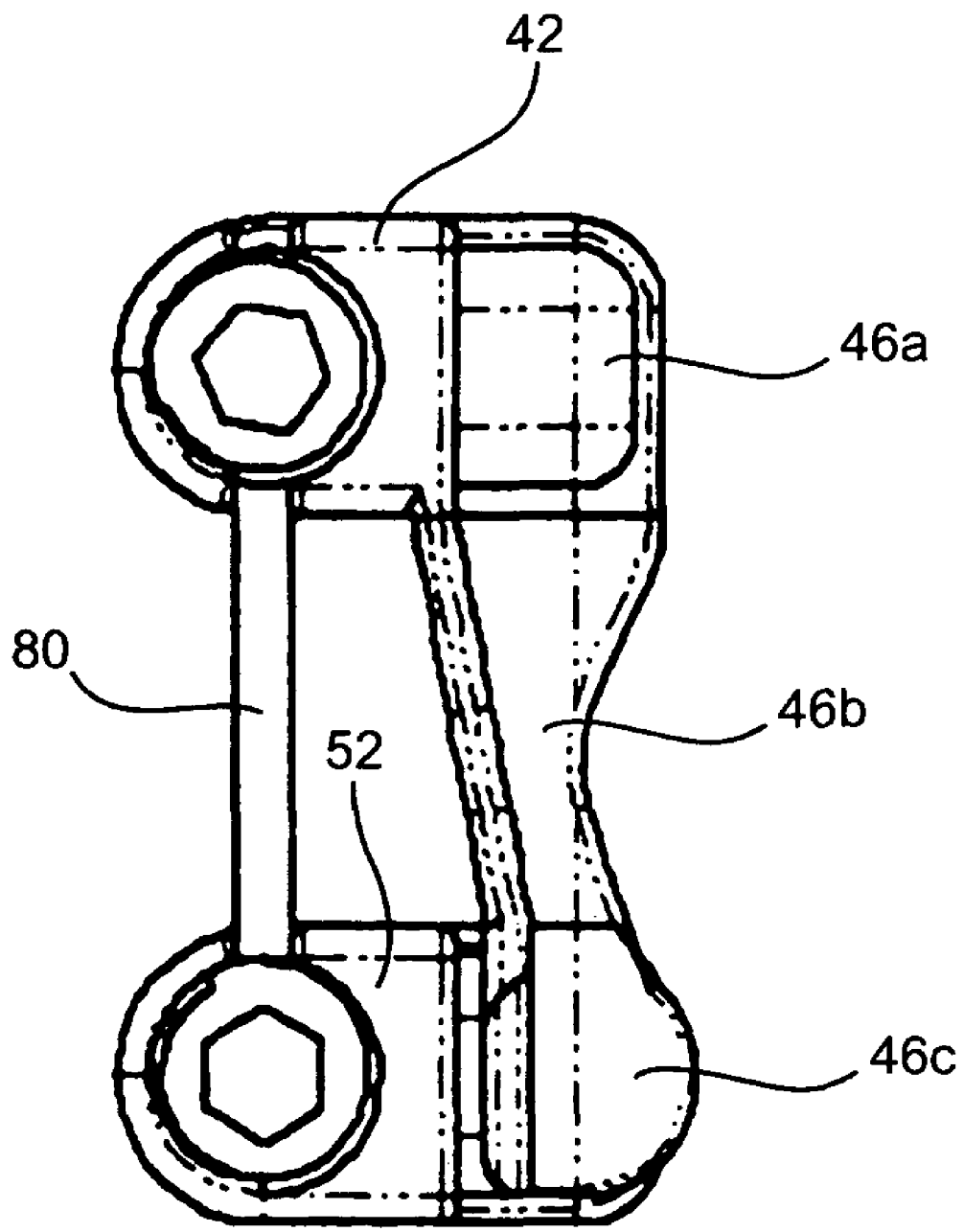
Figure 11:
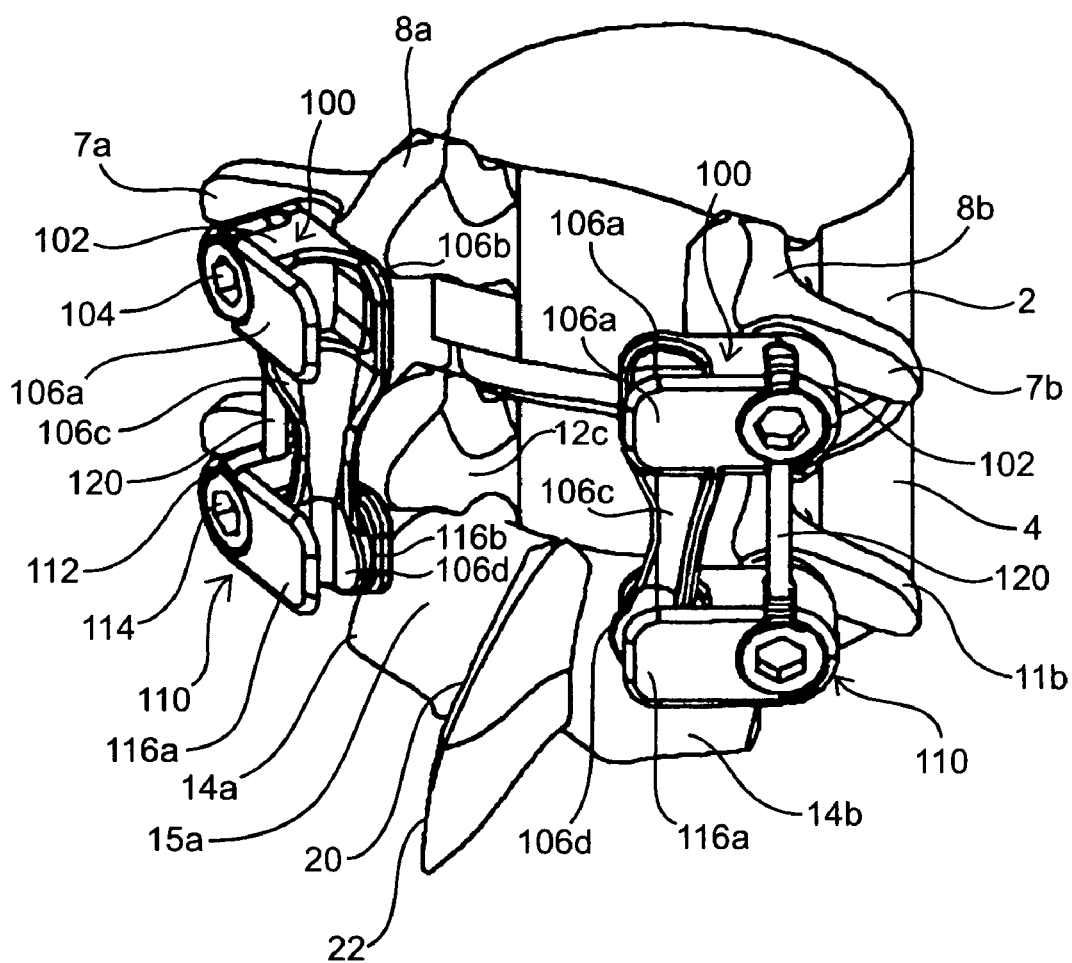
FIG. 11 illustrates another embodiment of a dynamic stabilization system of the present invention implanted within a portion of the spine.
Figure 12A:
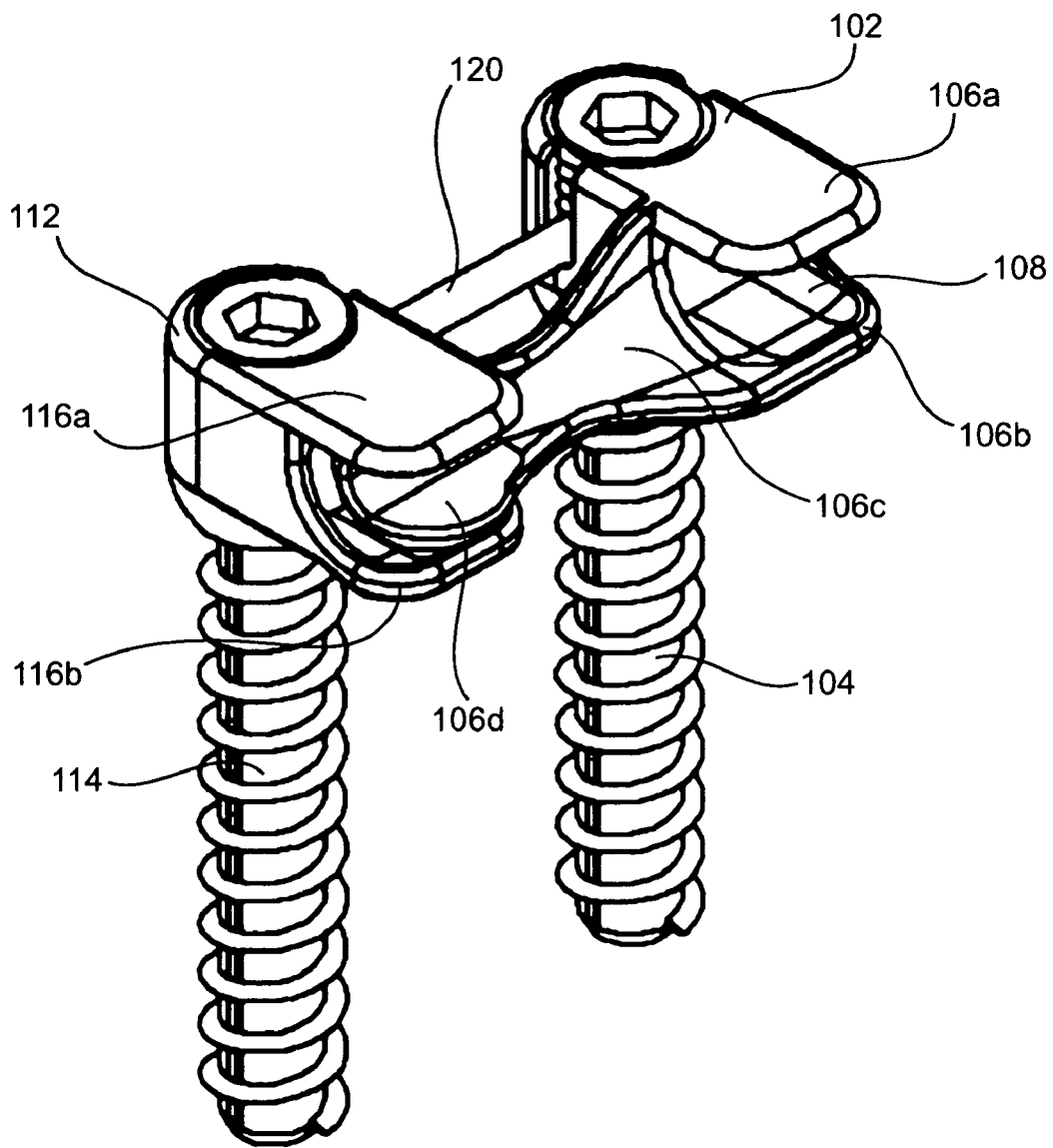
FIGS. 12A, 12B and 12C are perspective, side and top views, respectively, of the system of FIG. 11.
Figure 12B:
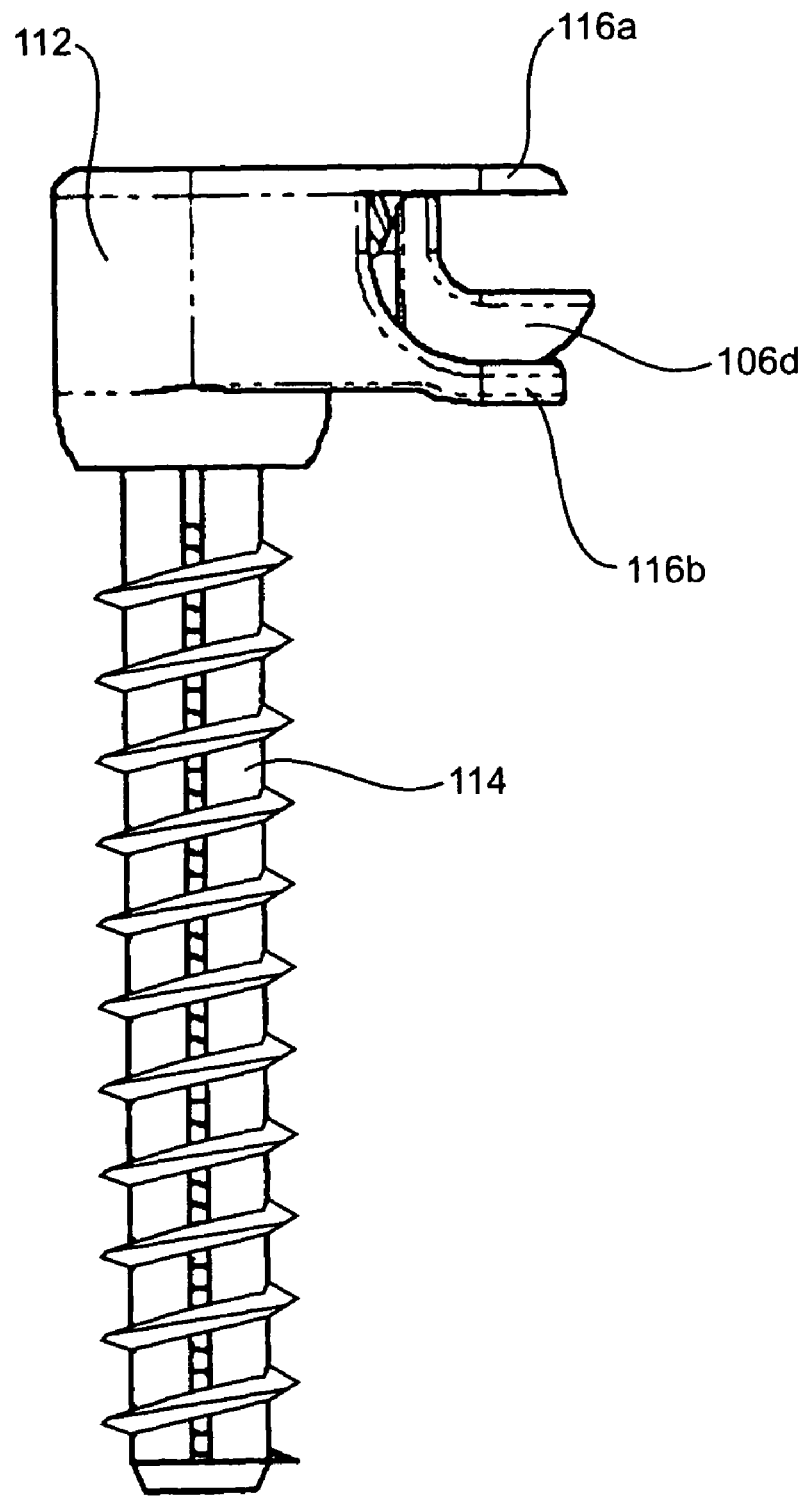
Figure 12C:
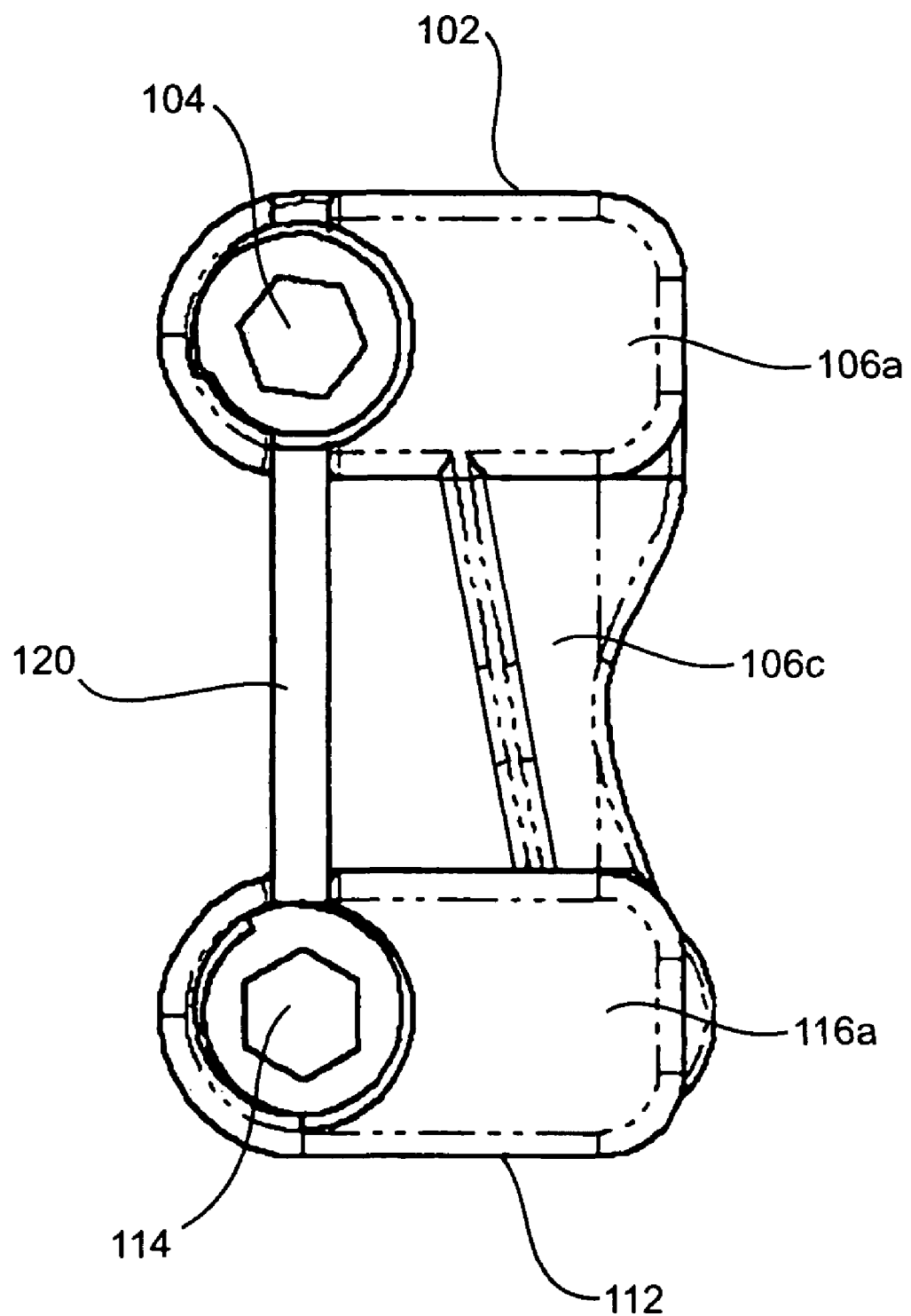

A portion of the systems of FIGS. 8 and 9 is further illustrated in FIGS. 10A-10C. Ligament 80 includes superior and inferior ends 82 and 84, respectively, which are captured within screw holes 41 and 51, respectively, of the superior and inferior base portions. Each ligament end is held between an insert 43, 53 and a threaded nut 45, 55 which are collectively positioned within screw holes 41 and 51, respectively. Inserts 43 and 53 are cupped to receive the disc-shaped ligament ends 82 and 84. The ligament ends and inserts are seated within the screw holes on top of the screw heads of screws 44 and 54, respectively. Threaded nuts 45 and 55 are then threadedly inserted on top of the ligament ends 82 and 84, respectively, to securely hold ligament 80.

Tension band 80 is made of a semi-elastic material which helps maintain the necessary distraction between the interconnected vertebrae while allowing for controlled compression, for example, during lateral bending, i.e., while the ligament of one side of a left-right system pair is experiencing distraction, the other ligament is experiencing compression. Additionally, the ligaments are marginally flexible to enable axial rotation and subluxation with limitations corresponding to that of a normally functioning spine segment. Suitable materials for the ligaments of the present invention include but are not limited to polymers and elastomers. The ligaments may also be made in the form of a nitinol cable. Additionally, the ligaments may be provided with a covering, such as a polyeurathane cover, to prevent tissue ingrowth which may interfere with the proper functioning of the ligaments.

FIGS. 11 and 12A-12C illustrate another variation of a system of the present invention. Superior and inferior components 100, 110 have generally similar constructs to corresponding components discussed above, however, the base portions 102, 112, respectively, each have posterior portions 106a, 116a, respectively, spaced from anterior portions 106b, 116b, respectively, defining a groove or slot therebetween. This slot provides a space in which the distal portion, such as distal portion 106d, of the strut 106c of a superior component is received. The interior configuration 108 of the slot spacing and the external surface of distal portion 106d may have any suitable corresponding configurations, e.g., rounded, angular, etc. The posterior portions of the slot further retain the distal strut portion during flexion motion as well as ensure against posterior translation of vertebrae 2 relative to vertebra 4. This system has pedicle screws 104, 114 which are similar to that of the other previously discussed systems and may optionally include a tension band or ligament 120.

Figure 13A:
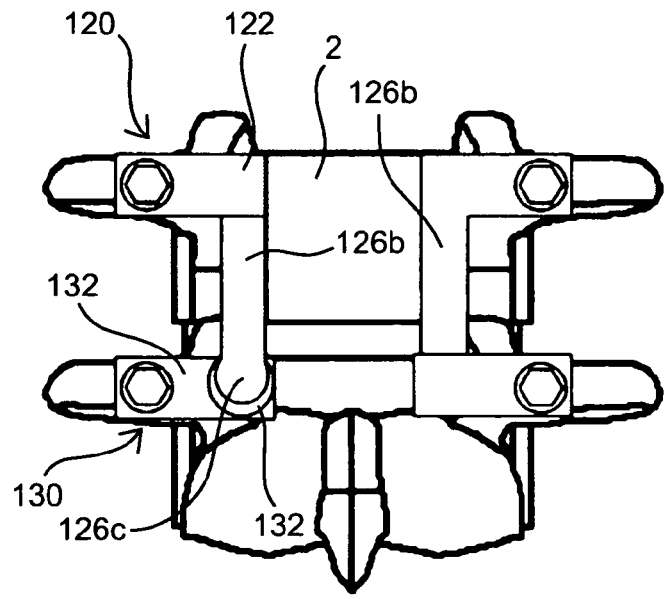
FIGS. 13A and 13B illustrate dorsal and side views, respectively, of another embodiment of dynamic stabilization system of the present invention implanted within a portion of the spine.
Figure 13B:
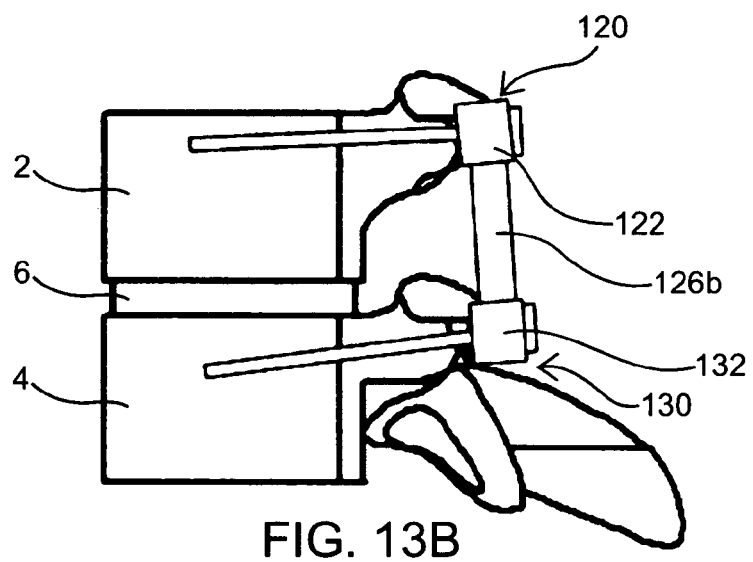
Figure 14:
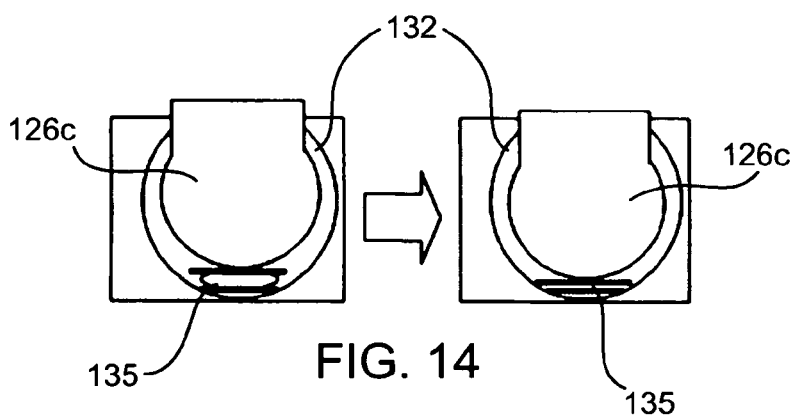
FIG. 14 illustrates uncompressed and compressed states of a ball-and-socket joint of the system of FIGS. 13A and 13B.

FIGS. 13A and 13B illustrate another variation of a system of the present invention in which the interface between superior component 120 and inferior component 130, and specifically between the distal strut portion 126c of superior component 120 and the engaging portion 132 of inferior component 130 (shown as a cut-out), is an enclosed ball-and-socket design. The proximal or superior portion (not shown) of the strut 126b and corresponding engaging portion (not shown) may also have a ball-and-socket configuration to provide additional range of motion. As is best illustrated in FIG. 14, the socket portion has a spherical configuration having a diameter that is slightly larger than that of the ball. In between the distal most portion of the ball and the opposing wall or surface of the socket is positioned a compressible member 135, such as a spring or an elastomer, polymer or metal ring or washer. Spring 135, which provides shock absorbency between the ball and socket, particularly upon compression of the spine in the axial direction, allows for a smoother interface and motion.

Figure 15B:
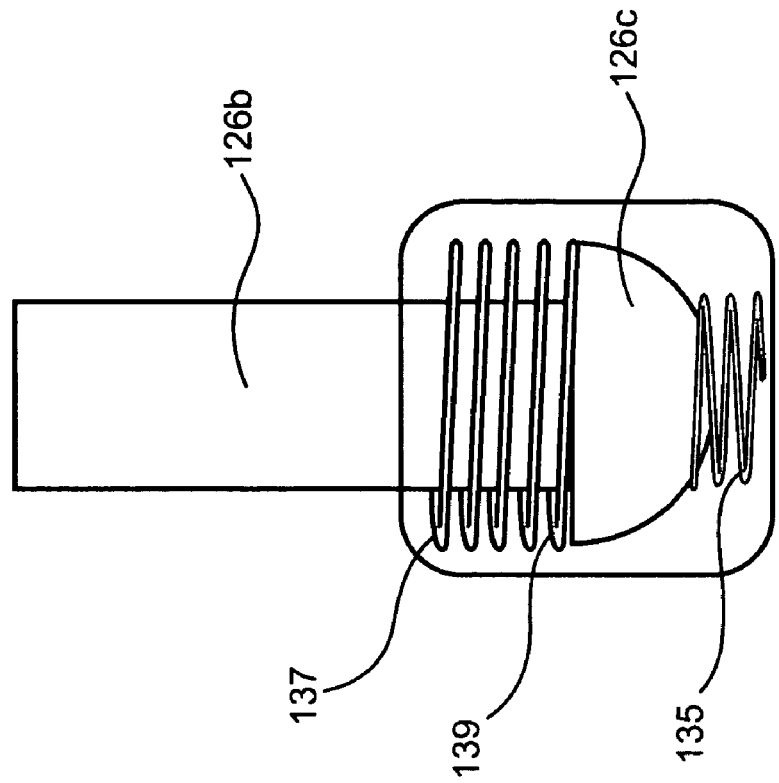
FIGS. 15A and 15B illustrate another variation of a ball-and-socket-joint of the system of FIGS. 13A and 13B FIGS. 16A and 16B illustrate dorsal and side views, respectively, of another embodiment of dynamic stabilization system of the present invention implanted within a portion of the spine.
Figure 15A:
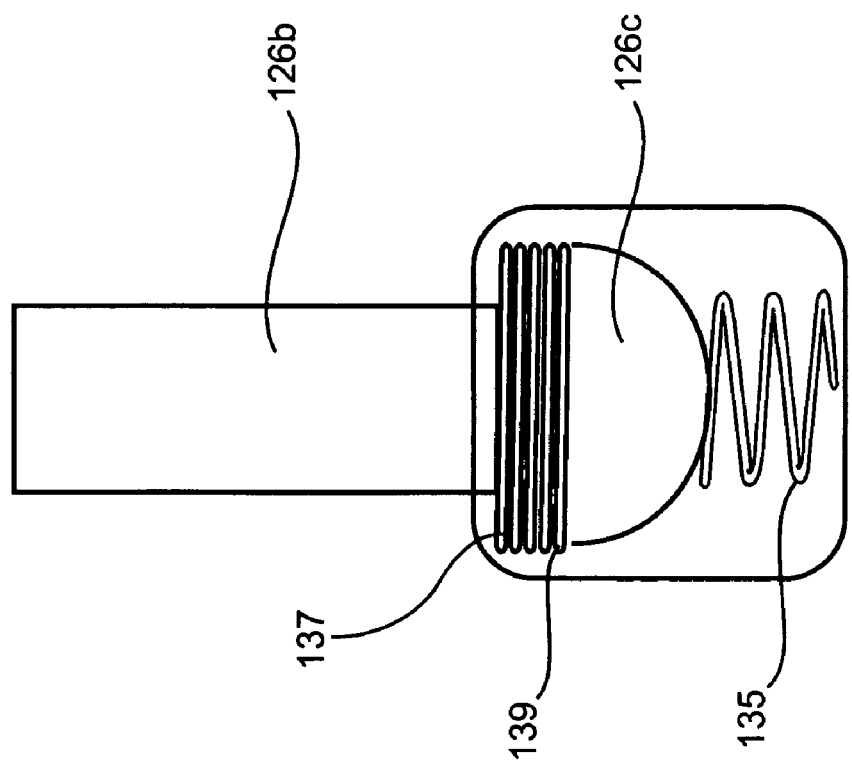

FIGS. 15A and 15B illustrate a variation of a ball-and-socket joint usable with the system of FIGS. 13A and 13B having dual opposing compressible members to provide shock absorbency during both compression and extension of the spine. Here, distal portion 126c has a semi-spherical configuration and provides a ledge 139 upon which a second compressible member 137 is provided in addition to first compressible member 135. The two members work in tandem such that when first compressible member 135 is in an expanded condition, as shown in FIG. 15A, the second compressible member 137 is in a compressed condition, and visa versa as shown in FIG. 15B.

Figure 16A:
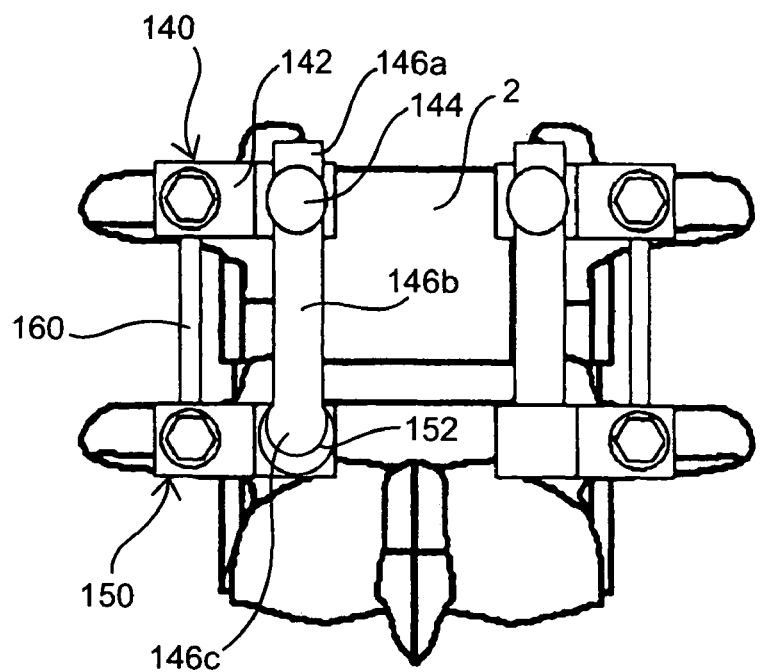
Figure 16B:
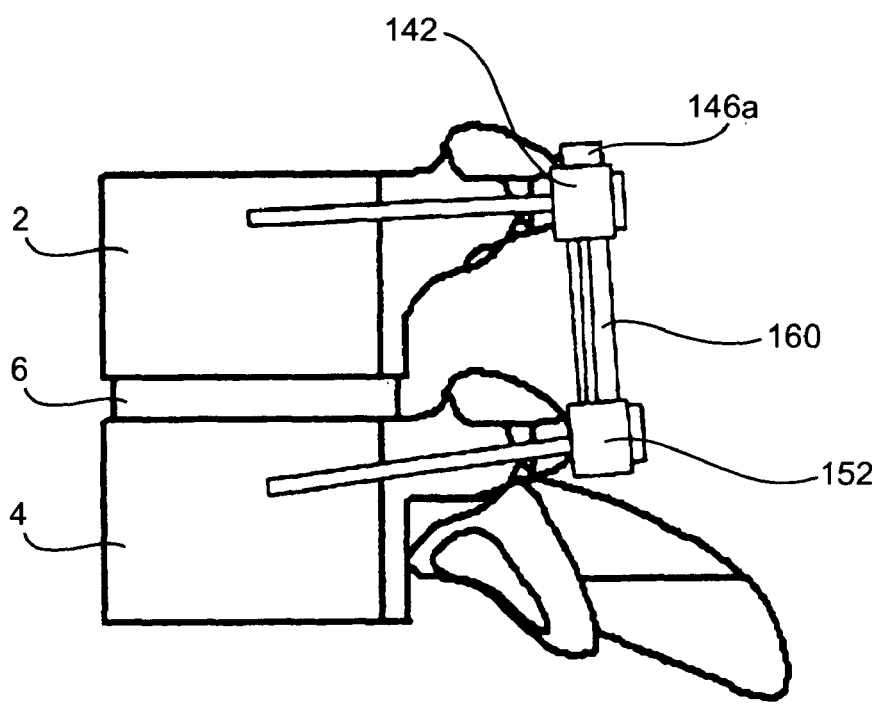

FIGS. 16A and 16B illustrate another embodiment of a system of the present invention having a ball-and-socket interface between the superior and inferior components which is similar to those previously described, however, an adjustment means 144 is provided in base portion 142 of superior component 140 to allow for the intraoperative adjustment of the length of strut 146b. Adjustment means 144 may be a pin or the like, the shaft of which has an eye or opening (not shown) through which the proximal portion 146a of the strut is position, and axially adjusted to accommodate the vertebral spacing of the patient. Upon achieving the desired strut length or vertebral separation, the pin is inserted or otherwise adjusted to cinch down on and hold the proximal portion of the post. As such, the physician to selectively adjust the length of the strut or strut intraoperatively to accommodate a range of intervertebral spacing distances. Additionally, the adjustability of the strut allows the physician to selective distract the vertebrae to restore sagital alignment of the vertebral segment and the natural lordosis, as well, if applicable, to reverse herniation suffered by the intervertebral disk. Such a configuration eliminates the need to provide or stock a multiple system components having varying strut lengths. The strut or at least the proximal end 146a thereof may be made of a material that is removable or otherwise may be removed, e.g., cut or clipped, so as to remove extraneous material. As with any of the systems of the present invention, a ligament 160 may be additionally employed to couple between the superior and inferior components 140, 150.

Figure 17B:
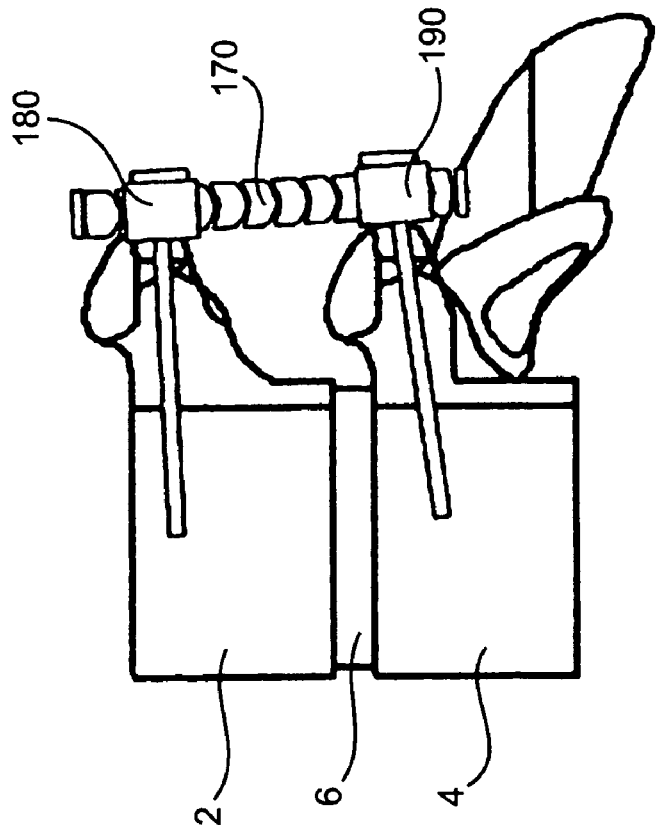
FIGS. 17A and 17B illustrate dorsal and side views, respectively, of another embodiment of dynamic stabilization system of the present invention implanted within a portion of the spine.
Figure 17A:
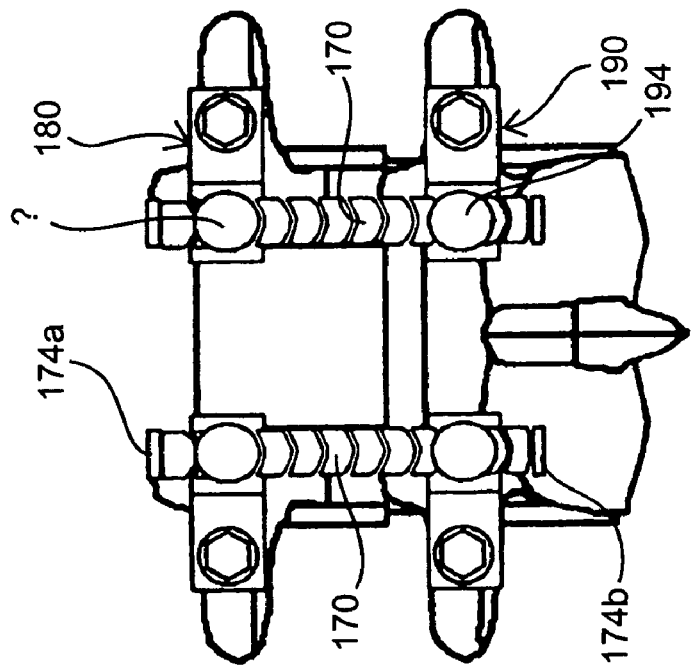

FIGS. 17A and 17B illustrate another variation of a system of the present invention in which an adjustable, flexible strut 170 is provided, the length and shape of which may be adjusted and subsequently fixed intraoperatively. Flexible strut 170 includes a plurality of joints or segments 172 strung on a wire, cable, thread or filament 176. Segments 172 may have any suitable shape and configuration but are preferably configured to resist slippage with adjacent segments upon compression. For example, as shown in FIG. 18A, segments 172 are cylindrically shaped and have a concave proximal end 172a and a convex distal end 172b so as to enable a nesting arrangement between the plurality of segments when compressed together. Moreover, the engaging surfaces between adjacent segments 172 allow off-axis positioning of the segments, as shown in FIG. 18B, to optimize or customize the axial shape of the strut 170. For example, the desired fixed shape of strut 170 may have a single bend or curve (i.e., C-shaped) or a double bend or curve (i.e., S-shaped). Upon achieving the desired shape, the segments 172 can be compressed against each other and locked into place to provide a substantially rigid rod. The segments are preferably made of a substantially hard material, such a metal or plastic, to provide the desired rigidity upon permanent fixation of the rod. Although substantially rigid, the rod may still be slightly flexible to accommodate bending motions. To facilitate manipulation and positioning of segments 172, one or more proximal and distal segments, 174a, 174b, 175a, 175b may be particularly configured. In particular, segments 174a, 174b may have a means for locking or cinching on to filament 176. As with certain of the above-described systems, flexible strut 170 may be selectively fixed to superior and inferior components 180, 190 by pins 184 and 194, respectively, or the like, such the length of the portion of the strut between the components may be adjusted thereof to accommodate the natural and/or desired vertebral spacing.

FIGS. 19A-19C illustrate a variation of a flexible strut 200 usable with the subject systems. Strut 200 includes segments 202 and spacers or washers 204 which are positioned between segments 202. Unlike segments 172, segments 202 have proximal and distal surfaces which are identically shaped to each other. Specifically, the segment ends are both concave or beveled to accommodate the spacers 204 which have a convex disk shape. The segments and the spacers may be made of the same or different material. In one embodiment, the spacers 204 are made of a compressible material to provide a spring function while the segments are made of a harder material, as described above. This configuration allows the most flexibility in strut shape and configuration while minimizing the risk of slippage between the segments once fixed in place. Various strut shapes are illustrated where FIG. 19A illustrates strut 200 in an uncompressed, straight configuration; FIG. 19B illustrates strut 200 in a compressed, straight configuration; and FIG. 19C illustrates strut 200 in a semi-compressed, curved configuration. The materials discussed above with respect to strut 170 may also be employed with strut 200.

Figure 20A:
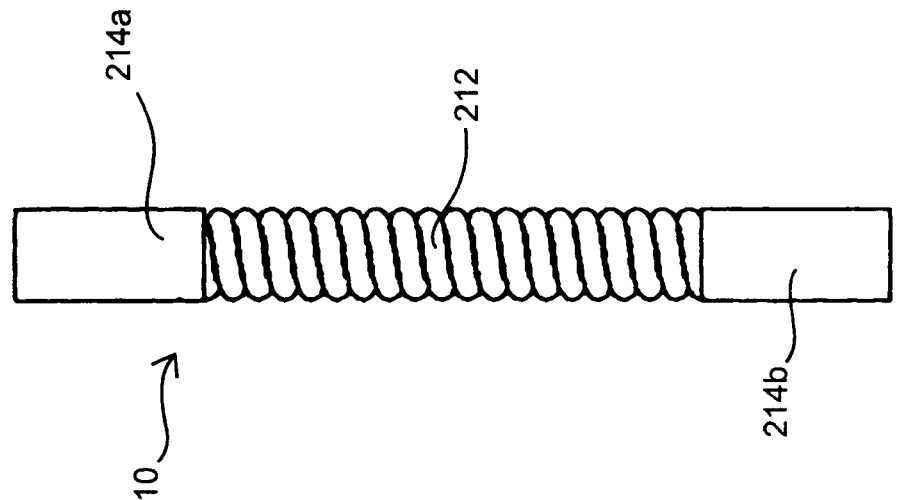
FIGS. 20A and 20B illustrate uncompressed and compressed states of another embodiment of a strut, ligament or band usable with the system of FIGS. 17A and 17B.
Figure 20B:
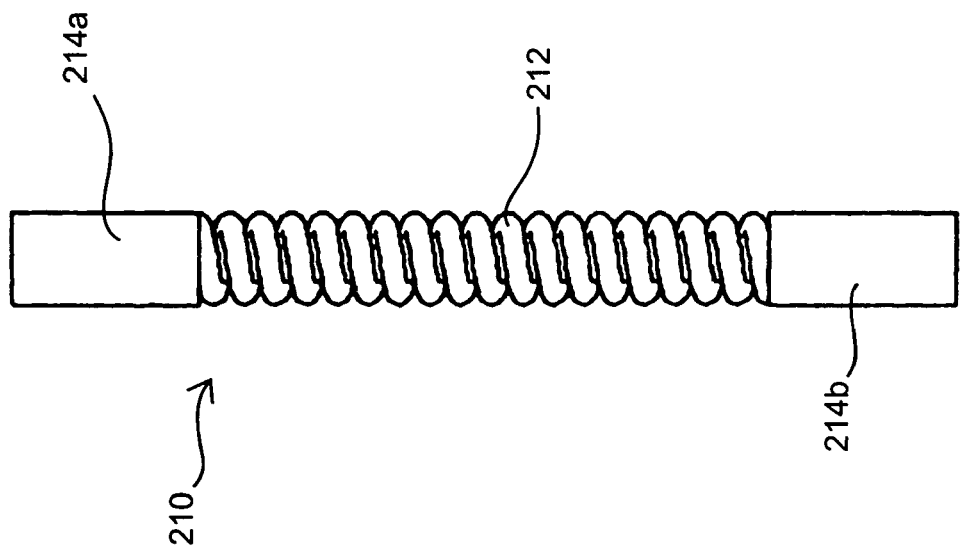

FIGS. 20A and 20B illustrate another embodiment of strut or interconnecting member or strut 210 which is usable with the system of FIGS. 16A and 16B. Interconnecting member 210 includes a spring 212 extending between and affixed to cylindrically shaped superior and inferior ends 214a and 214b. As with the struts discussed above, ends 214a and 214b are fixed to superior and inferior components by pins 184 and 194, respectively. Upon implant, strut 210 can be selectively distracted or compressed to achieve the desired intervertebral spacing or distraction. The desired length, once achieved, is locked into place by locking the strut ends to the superior and inferior components such as by a pin mechanism as described above. As such, the length of the portion of the strut between the components may be adjusted to accommodate the natural and/or desired vertebral spacing, and provides sufficient flexibility, compression and distraction to accommodate and facilitate spinal motion.

Figure 21A:
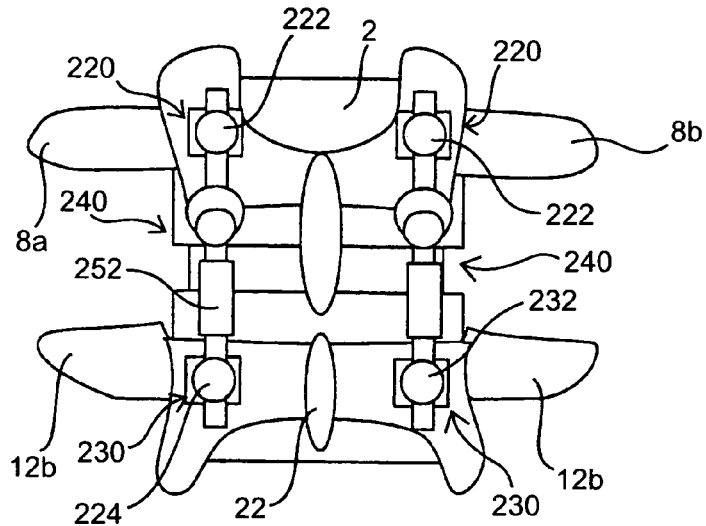
FIGS. 21A and 21B illustrate dorsal and side views of another variation of a system of the present invention.
Figure 21B:
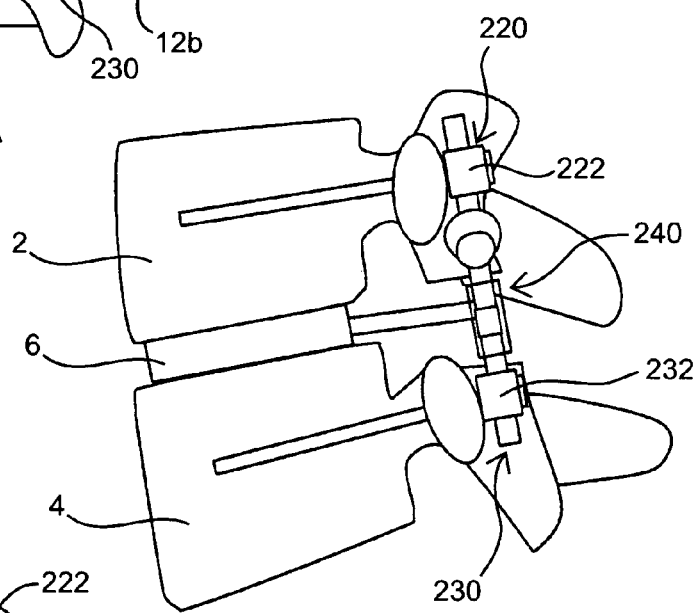
Figure 22:
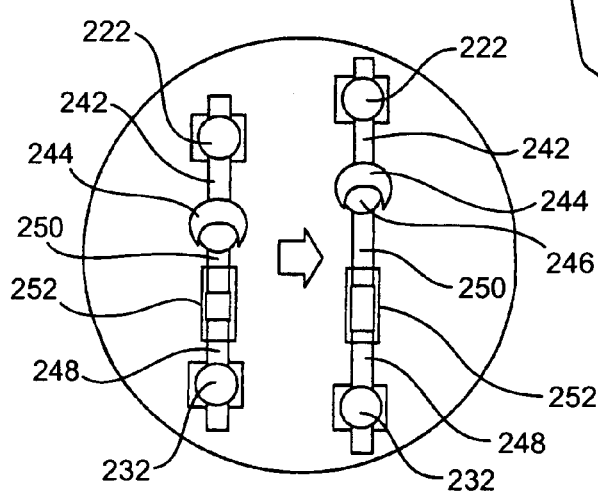
FIG. 22 illustrates the member interconnecting the superior and inferior components of the system of FIGS. 21A and 21B.

Another variation of a system of the present invention is illustrated in FIGS. 21A and 21B having superior components 220 and inferior components 230. Instead of employing ball-and-socket joints at the superior and/or distal end joints of strut 240, a ball-and-socket joint 244 and a compressible joint 252 are employed medially or centrally of strut 240. As shown in FIG. 22, strut 240 includes proximal, medial and distal segments 242, 250 and 248, respectively, where ball-and-socket joint 244 interconnects the proximal and medial segments and compressible joint 252 interconnects the medial and distal segments. The ball-and-socket joint 244 includes a proximal socket and a distal ball which may allow for rotational movement alone (to facilitate flexion, extension and lateral bending motions) or may additionally provide for some limited compression and/or distraction between superior and inferior components 220, 230 by the inclusion of one or more spring members to address axial loading experienced by the spine. Compression joint 252 includes a spring member (not shown) such that joint 252 provides for shock absorbency, both during compression and during distraction, of the spine.

Figure 23A:
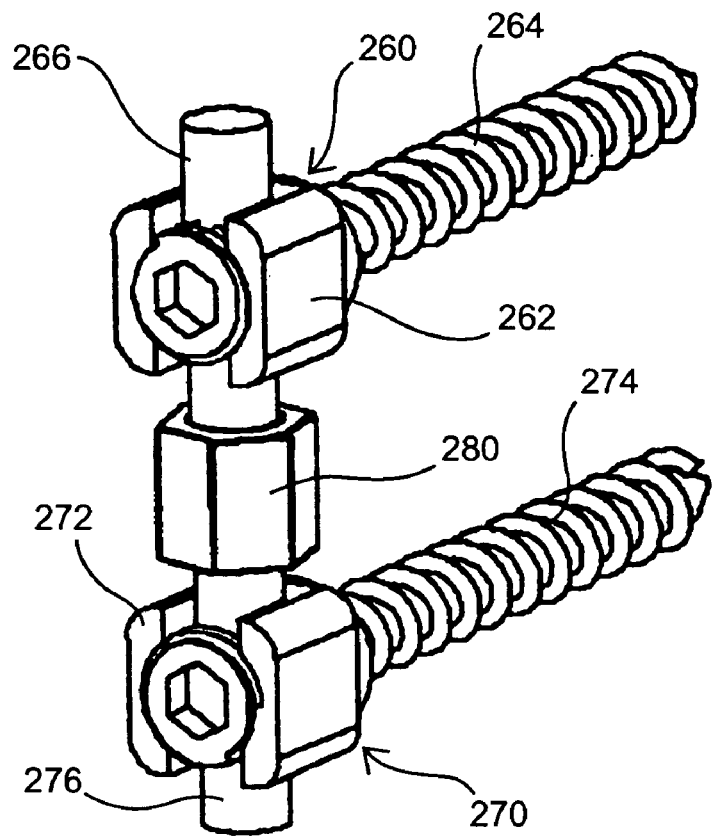
FIG. 23A illustrates a perspective view of another variation of a system of the present invention.

FIG. 23A illustrates another embodiment of a system of the present invention having superior component 260 and inferior component 270. Superior component 260 includes a base 262 configured to received pedicle screw 264. Inferior component 270 includes a base 272 configured to receive pedicle screw 274. Extending from each of the base portions is a strut segment or portion 266 and 276, respectively. The proximal ends of screws 264 and 274 have a cross-bore (not shown) to receive the proximal ends of corresponding strut segments 266 and 276 in a transverse fashion. The distal end of superior strut segment 266 terminates in a compression member 268 and the distal end 278 of inferior strut segment 276 has a configuration for engaging with compression member 268. Here, inferior distal end 278 has a ball configuration and is received at the distal end of spring 268 to provide a central ball-and-socket joint. As illustrated in FIGS. 24A and 24B, the central joint provides shock absorbency during axial loading of the spine (FIG. 24A) and facilitates semi-constrained flexion, extension and lateral bending motions (FIG. 24B). A covering 280, which is fixed to either superior strut segment 266 or inferior strut segment 268, axially surrounds the central joint to prevent tissue in growth.

Figure 25A:
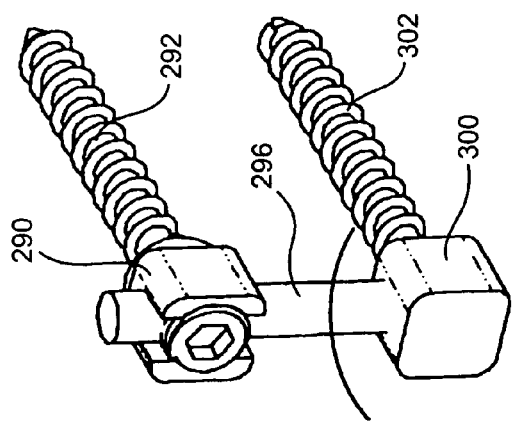
FIGS. 25A and 25B illustrate perspective views of other variations of systems of the present invention.
Figure 25B:
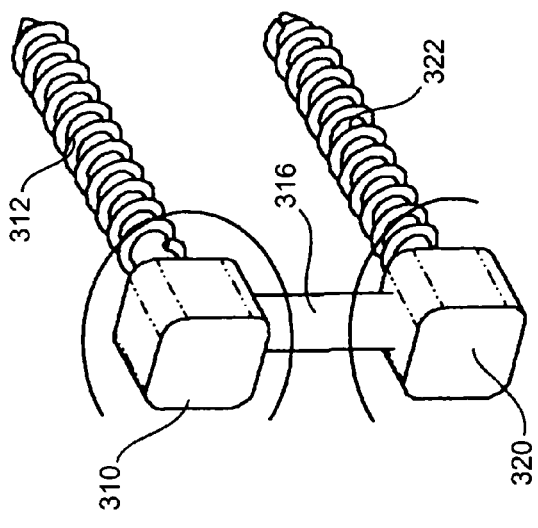
Figure 25C:
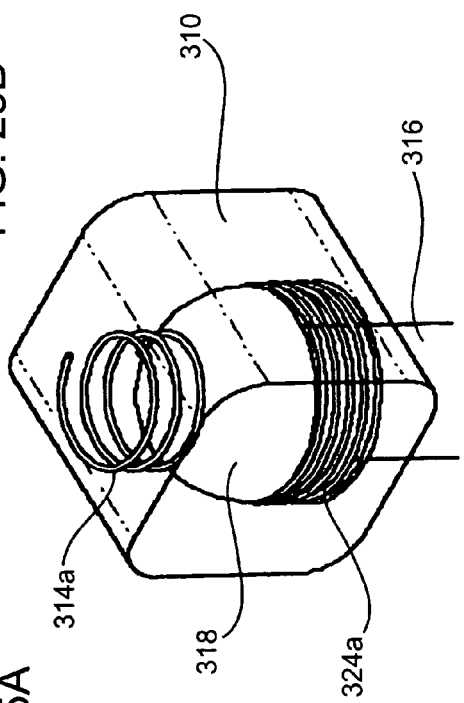
FIG. 25C illustrates a joint of the systems of FIGS. 25A and 25B.

FIGS. 25A and 25B illustrate variations of the immediately above-described system in that these systems provide for similarly functioning joints except for the joints are employed as end joints. Specifically, the system of FIG. 25A incorporates such a joint in the inferior component 300 from which the free end, here the distal end of interface member or strut 296, is received and retained. The proximal end strut 296 is adjustably retained within a transverse bore within superior pedicle screw 292 as described above. The system of FIG. 25B incorporates such joint in both the superior component 310 and the inferior component 320 with both the proximal and distal ends of interface strut 316 being received in the respective base portions of the components. As illustrated in FIG. 26, which features the joint of superior component 310 of FIG. 25B, the joints have ball-and-socket configuration similar to the joint of FIGS. 15A and 15B. Strut end 318 has a semi-spherical configuration and is received between distal spring 314a and proximal spring 324a which provide a semi-constrained relationship between the superior and inferior components. A similar configuration is provided within inferior base portion 320 as illustrated in FIGS. 27A and 27B.

Figure 26A:
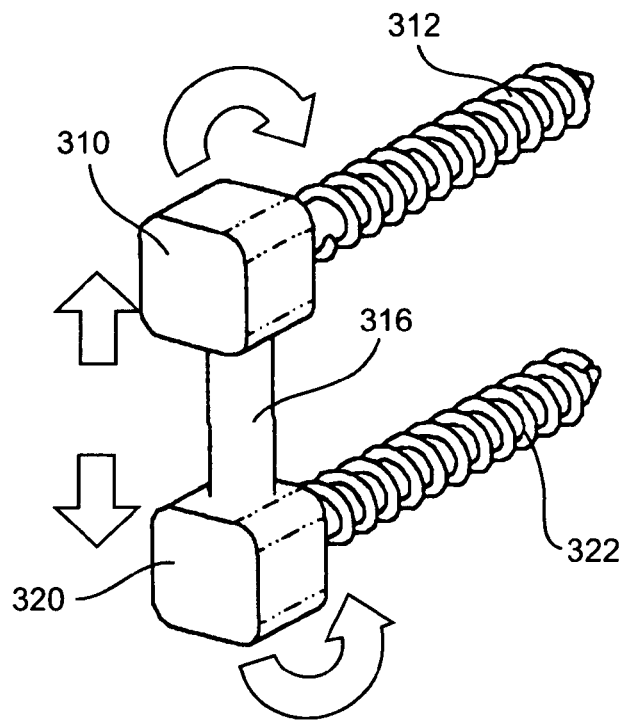
FIGS. 26A and 26B illustrate the system of FIG. 25B in flexion and extension motions, respectively.
Figure 26B:
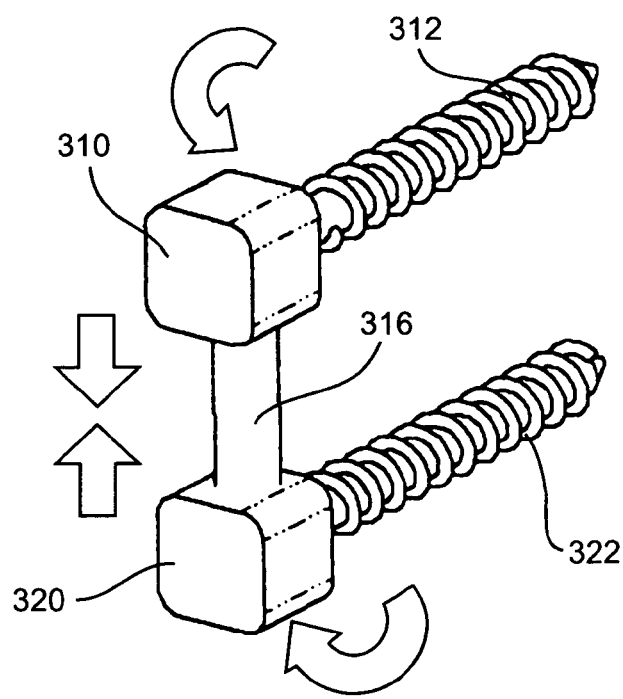
Figure 28A:
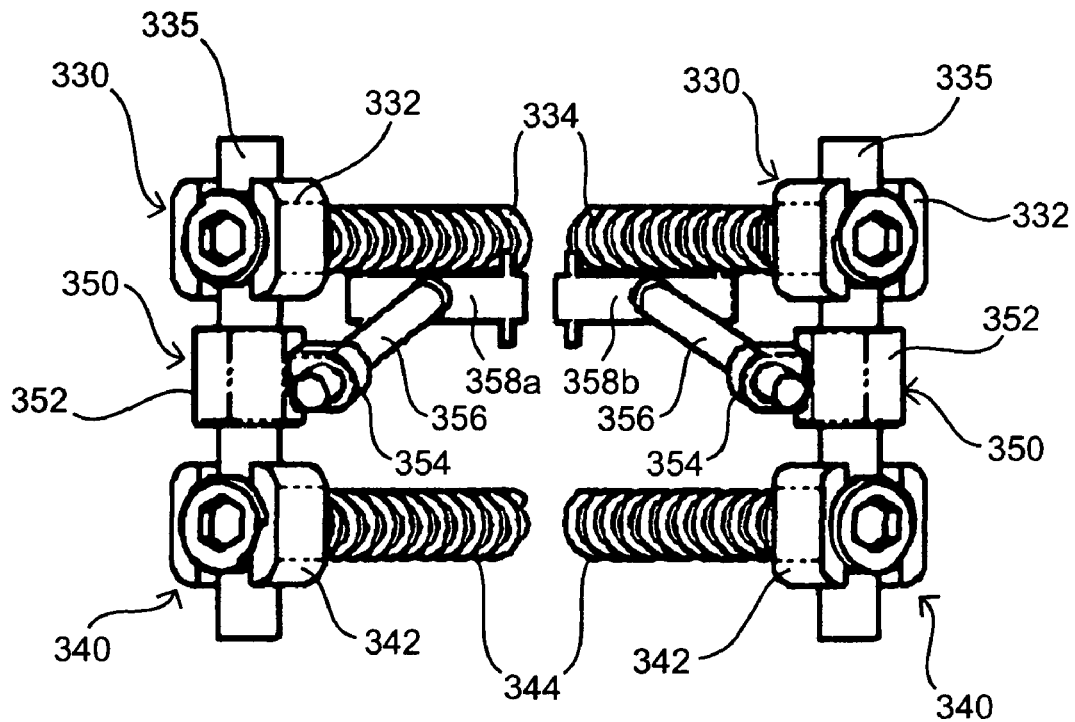
FIGS. 28A, 28B and 28C illustrate a dorsal, top and side views of another system of the present invention incorporating a prosthetic replacement intervertebral disk.
Figure 28B:
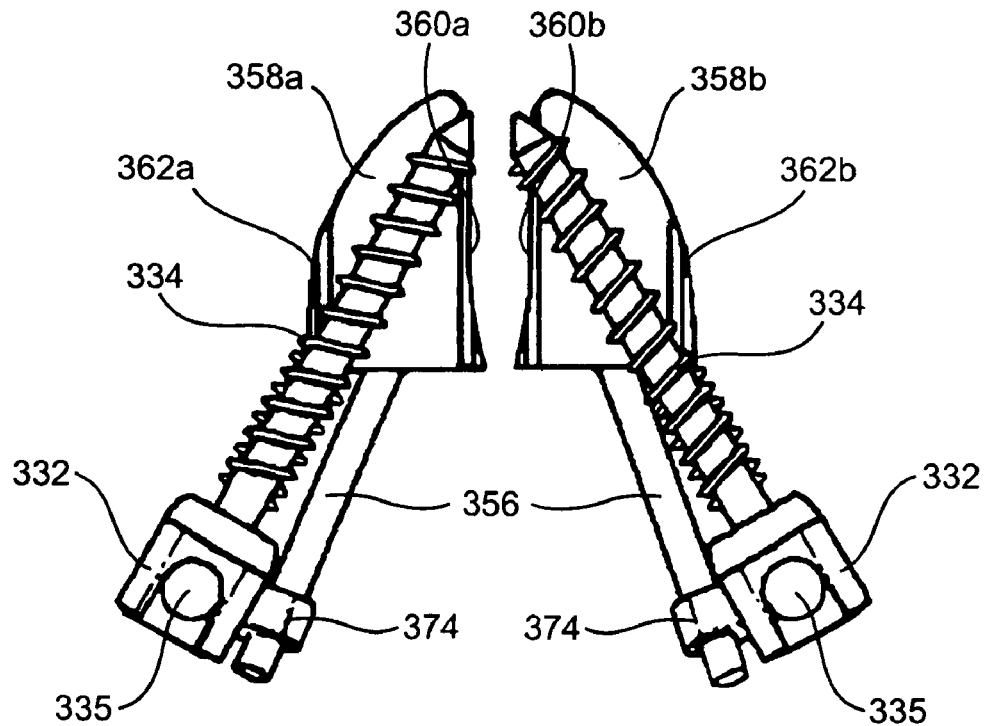
Figure 28C:
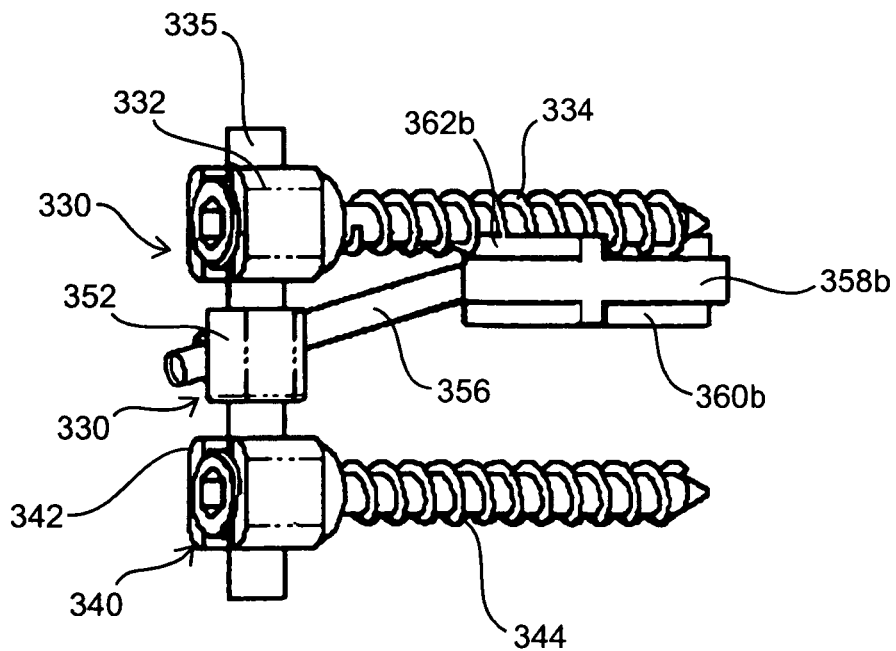

FIGS. 26A, 26B, 27A, 27B, 27C and 27D illustrate the semi-constrained motions facilitated by the joints of system of FIG. 25B. FIG. 26A illustrates the system in flexion motion and FIG. 27A illustrates the corresponding motion of the inferior joint housed within base portion 320 in which spring 314b is in an expanded or uncompressed state and spring 324b is in a compressed state. FIG. 26B illustrates the system in extension motion and FIG. 27B illustrates the corresponding motion of the inferior joint in which spring 314b is in a compressed state and spring 324b is in an uncompressed state. FIGS. 27C and 27D illustrate to motion of the superior joint of the system of FIG. 25B undergoing left and right lateral bending motions, respectively. The extent of compression/extension of springs 314a and 324a are comparable to each other while strut 316 undergoes a slight radial rotation (to the right upon left lateral bending (FIG. 27C) and to the left upon right lateral bending (FIG. 27D)).

Figure 23B:
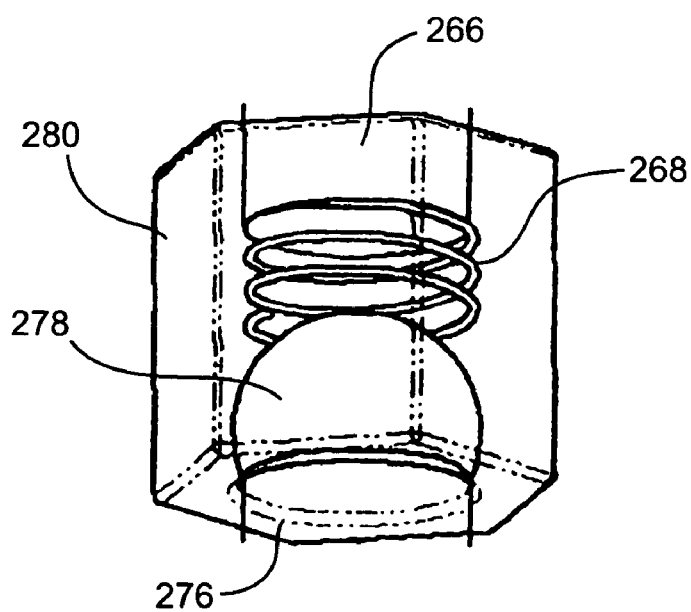
FIG. 23B illustrates a central joint of the system of FIG. 23A.

FIGS. 28A, 28B, 28C and 29 illustrate another system of the present invention. The system includes superior and inferior components 330 and 340, respectively, each having a base portion 332 and 342, respectively, and pedicle screw 334 and 344, respectively, as with many of the systems thus far described. The ends of interface member or strut 335 are adjustably received within the superior and inferior components as described above. Medially positioned between superior and inferior components 330 and 340 is a central joint 350 having a base portion 352 similar to that described above with respect to FIGS. 23A and 23B. Base member 352 has a medially extending portion 354 having a bore therein for receiving a rod 356 having a portion of a prosthetic intervertebral disk 358a, 358b pivotally coupled to a distal end thereof. Rod 356 may be provided fixed to base portion 352 or may be provided as a separate member which inserted, adjusted and locked into place intraoperatively, similar to the manner in which interface strut 335 interconnects with the superior and inferior components 330 and 340, respectively.

Figure 29:
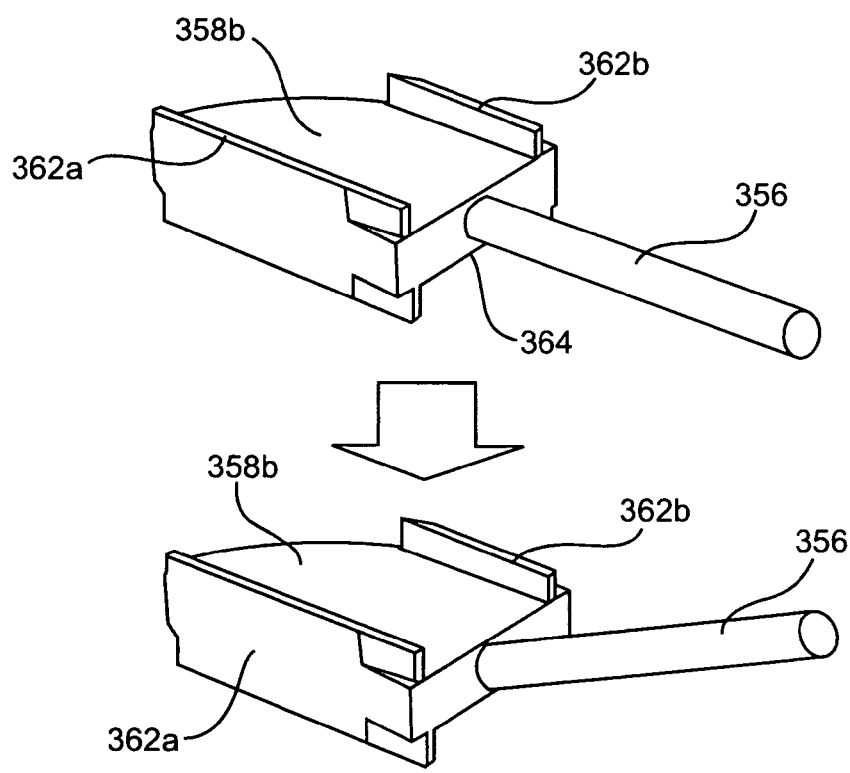
FIG. 29 illustrates a perspective view of the prosthetic intervertebral disk of the system of FIGS. 28A-28C.

Left replacement disk portion 358a and right replacement disk portion 358b each have a shape, size and thickness which is suitable for implantation between the respective left and right sides of the intervertebral disk spacing. Preferably, they are mirror images of each other such that, when both are operatively implanted within the invertebral spacing, a substantial portion of the spacing is occupied with the prostheses to provide a complete disk replacement in the intervertebral spacing of the targeted spinal motion unit. Each disk portion 358a, 358b includes medial keels or fins 360a, 360b and lateral keels 362a, 362b, respectively, for anchoring into the superior and inferior surfaces defining the intervertebral spacing. As illustrated in FIG. 29, each disk portion 358a, 358b (only 358b is shown), is pivotally connect to the distal end of rod 356 to accommodate varying axial loads experienced by the spinal motion unit into which the disk portions are implanted.

Figure 30A:
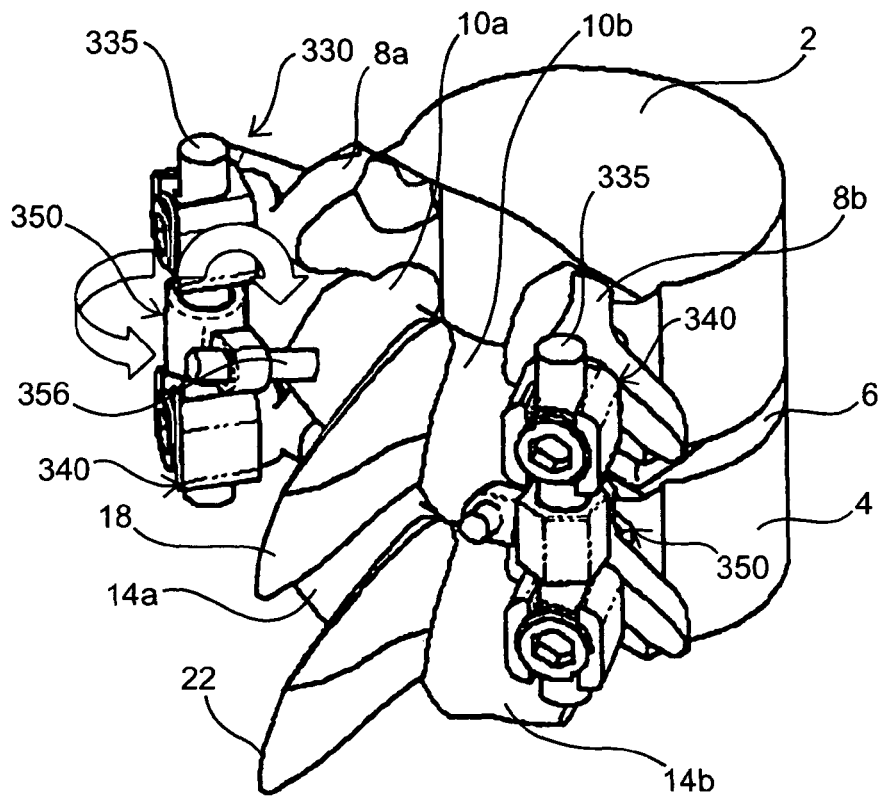
FIGS. 30A and 30B illustrate perspective and dorsal views of the system of FIGS. 28 and 29 implanted within a spinal motion segment.
Figure 30B:
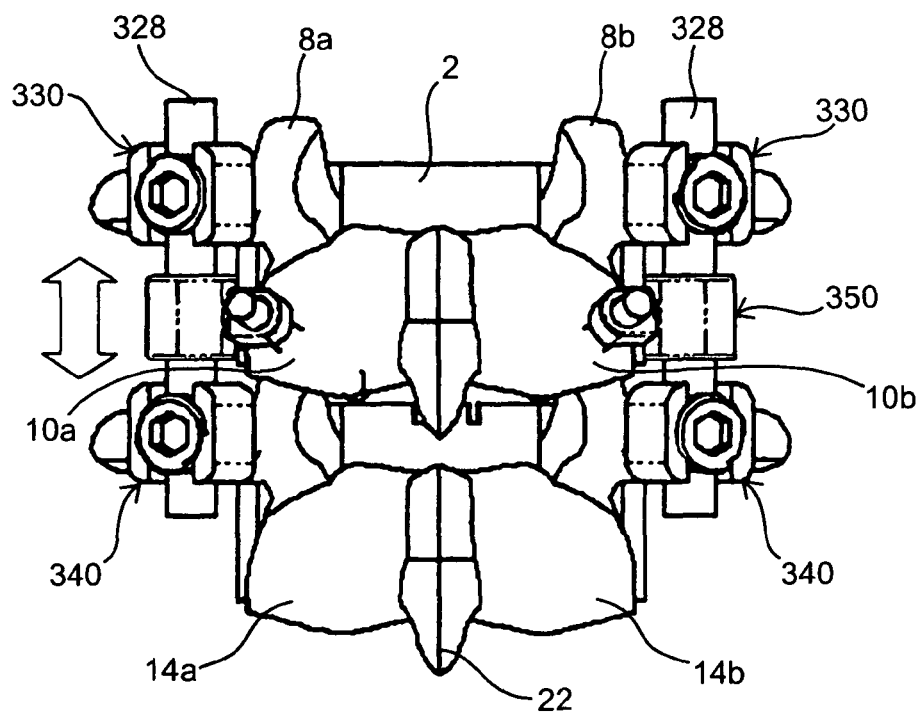

FIGS. 30A and 30B illustrate the system of FIGS. 28 and 29 implanted within a spinal motion segment. The procedure for implanting this system first involves performing a laminotomy or laminectomy from a posterior approach. After the posterior elements are removed and ample space is made posteriorly, identification of the thecal sac and exiting nerve roots is made. These structures are then retracted medially. With minimal retraction, the natural disc annulus is dissected out and entered using a scalpel. The annulus and nucleus of the disc is removed, i.e., a disectomy, using multiple pituitary rongeurs, curettes, and Kerrison punches. After the discectomy, the endplates of the superior and inferior vertebrae are removed using a high-speed drill, curettes or chisels. The prosthetic disc member or body graft 358a, 358b. Once the disc members are properly implanted, the superior and inferior components may be implanted. While disc members 358a, 358b are shown connected or secured to the dynamic stabilization system by way of rod 356, such is not required.

Figure 32A:
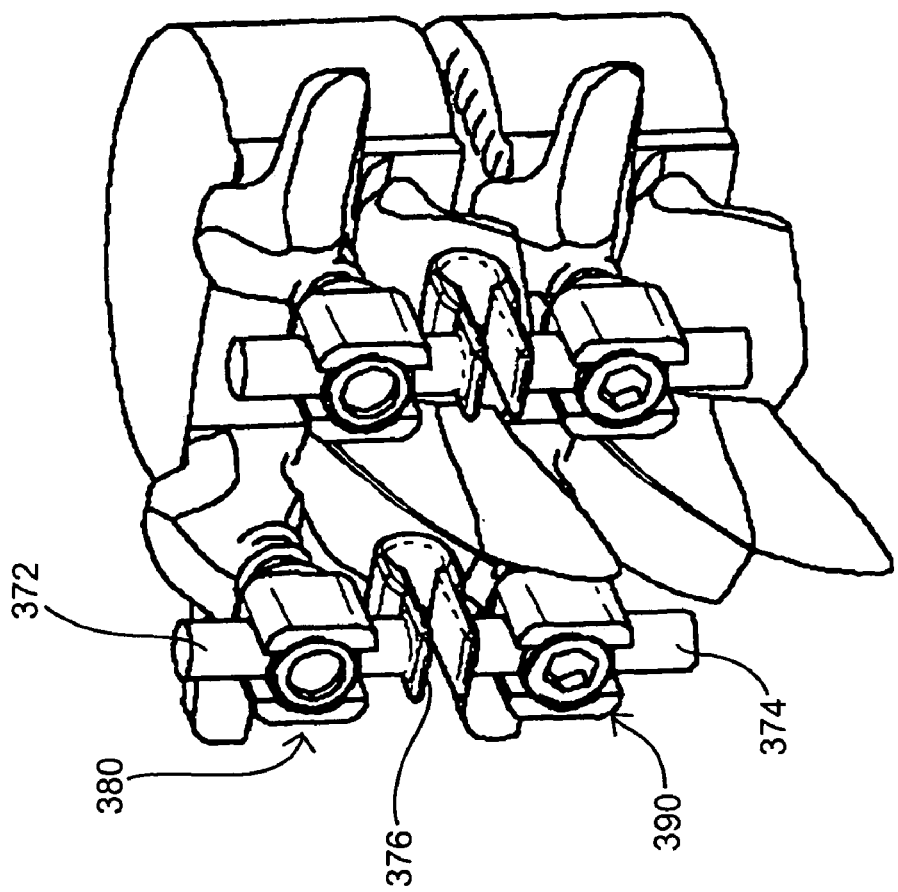
FIGS. 32A, 32B and 32C are perspective and side views of an implanted system of the present invention employing the interfacing strut of FIG. 31.
Figure 31:
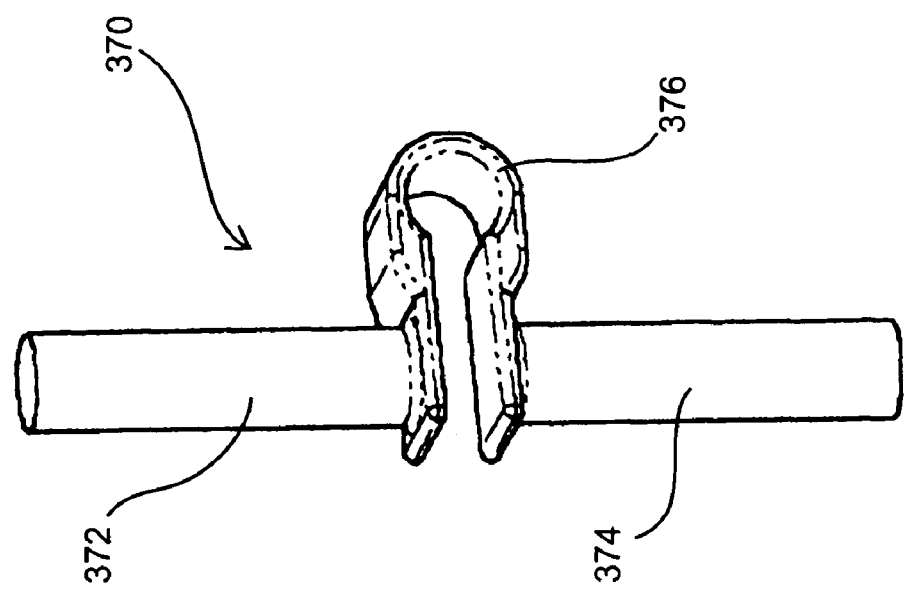
FIG. 31 illustrates an interfacing strut for use with various of the systems of the present invention.
Figure 32C:
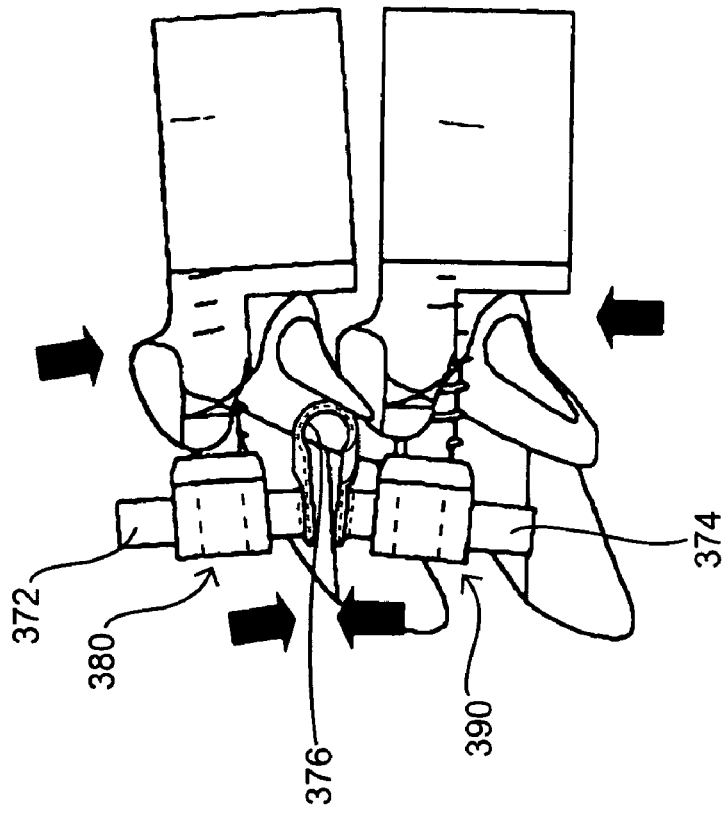
Figure 32B:
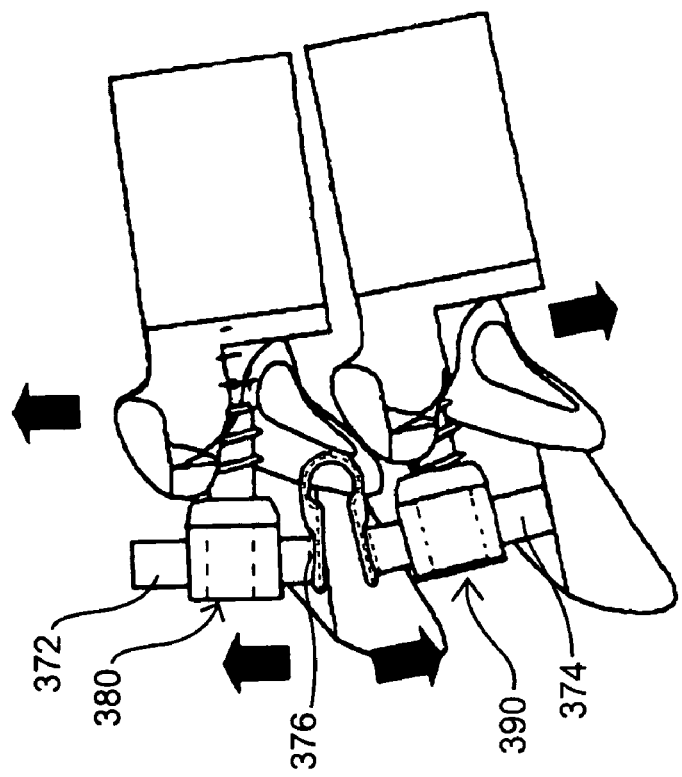
Figure 33A:
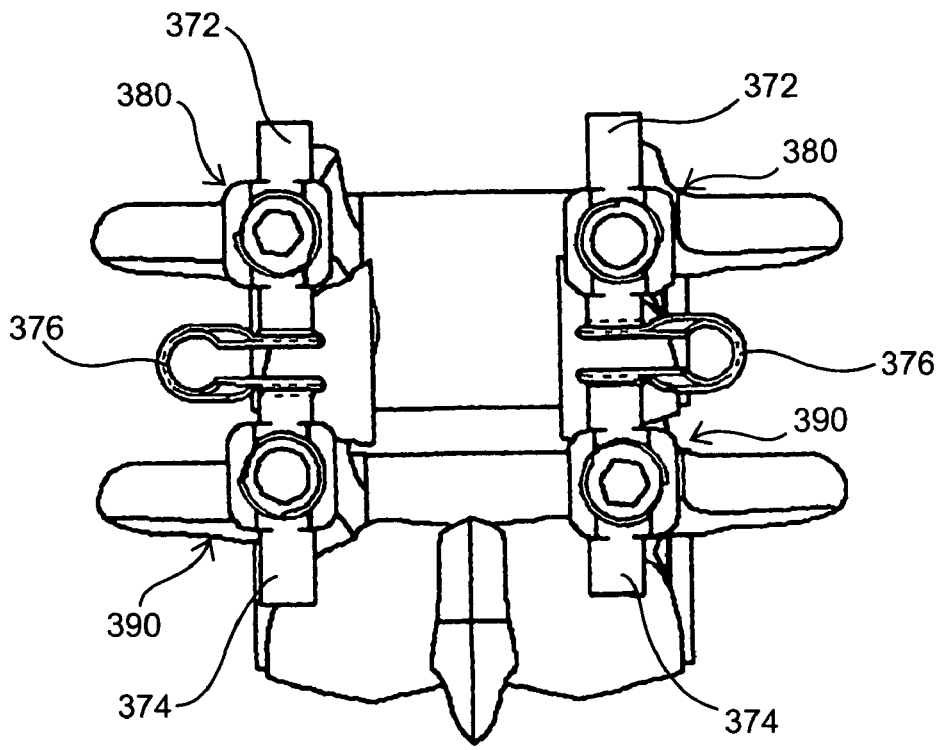
FIGS. 33A and 33B are dorsal views of other implanted systems employing the interfacing strut of FIG. 32 in a lateral configuration and a medial configuration, respectively.
Figure 33B:
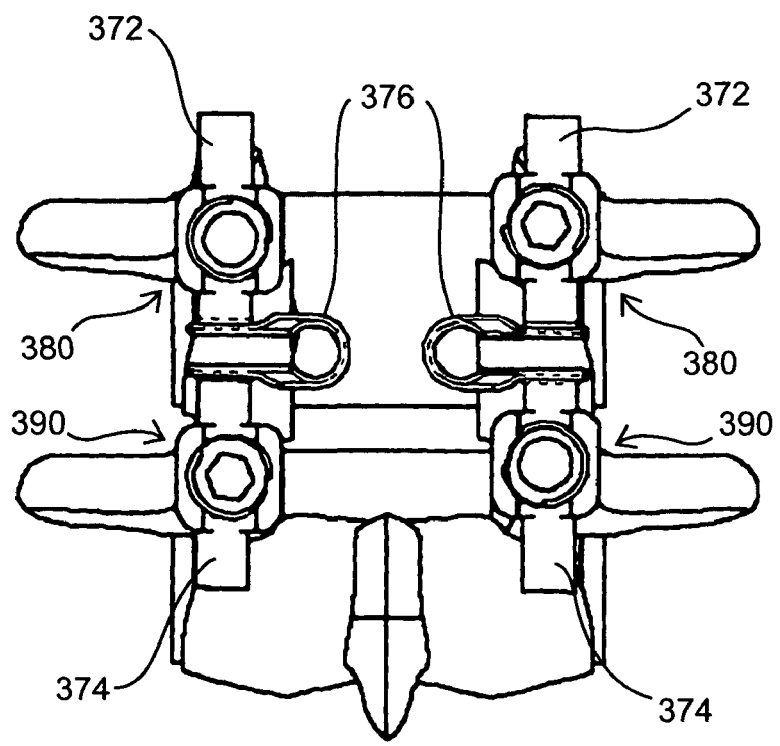

FIG. 31 illustrates an interface member or strut 370 for interconnecting the superior and inferior components of certain systems of the present invention. Interface member 370 includes superior and inferior strut portions 372, 374 for coupling to superior and inferior components 380, 390 respectively. Interface member further includes compression or spring member 376 having a U-shaped configuration having end portions sandwiched between interface strut portions 372, 374. The end portions of compression member 376 define a gap therebetween in the range from about 2 mm to about 3 mm but could be narrower or wider depending on the particular application, and the curved body portion of compression member 376 extends anteroposteriorly, or transversely to strut portions 372, 374. The direction in which the body of the compression member extends may be varied according to the particular application at hand. For example, FIGS. 32A-32C illustrate interface member 370 utilized in a system implanted within a spinal motion segment where strut portions 372, 374 are interconnected to superior and inferior components 380, 390, respectively, where the U-shaped compression member 376 is positioned so as to extend towards the posterior side of the motion segment. FIGS. 33A and 33B illustrate similar systems in which compression member 376 is positioned laterally and medially, respectively. Typically, an anteroposteriorly positioned compression member allows for a greater degree of flexion and extension while the laterally and medially positioned compression members allow for a greater degree of lateral bending. All three positions, however, will allow for a slight amount of axial rotation. FIGS. 32B and 32C illustrate side views of the implanted system of FIG. 32A undergoing flexion and extension motions, respectively.

FIGS. 34A-34E illustrate another embodiment of an interface member 400 that is usable with various systems of the present invention. Interface member 400 employs two stacked U-shaped compression members, superior compression member 406 and inferior compression member 408. While only two stacked compression segments are shown, any suitable number may be used to optimize the ability of the subject spinal motion segment to mimic the motion of the a healthy natural spine segment.

Figure 34A:
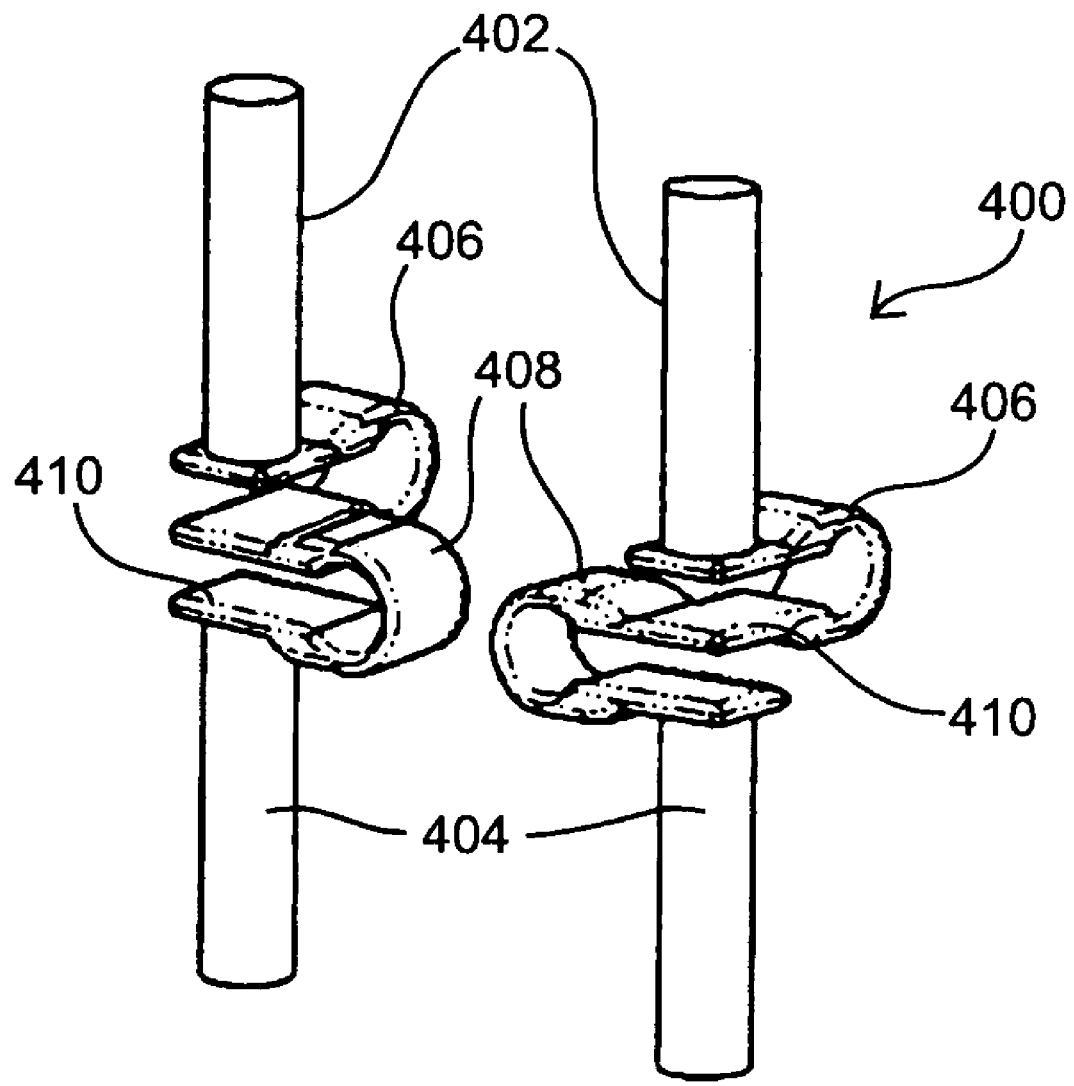
FIGS. 34A-34E illustrate a pair or set of another embodiment of interfacing struts usable with various systems of the present invention.
Figure 34C:
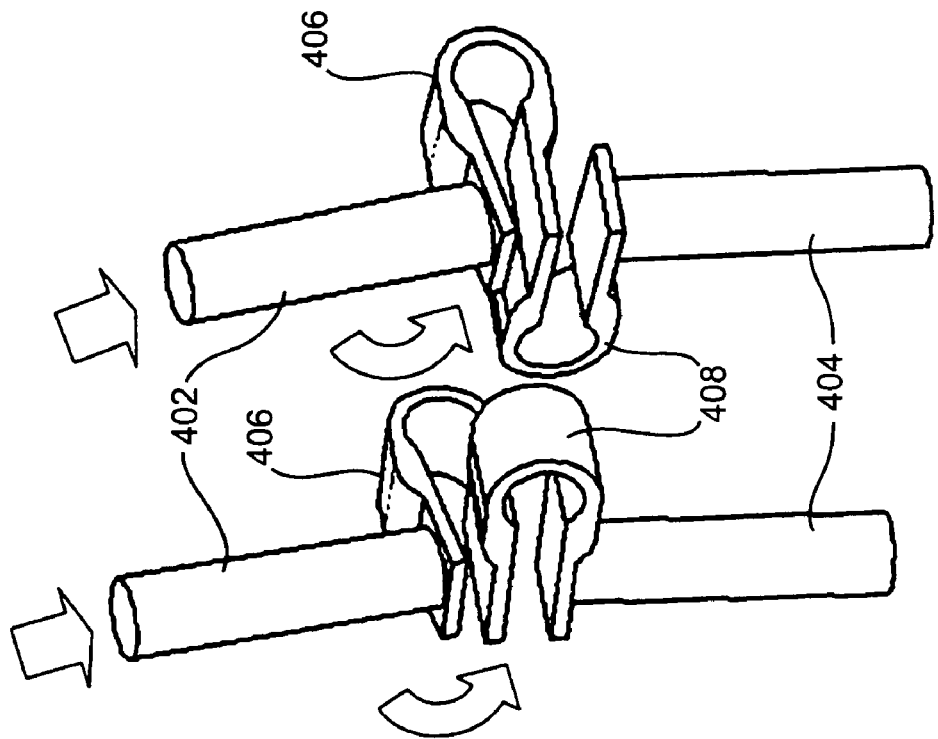
Figure 34B:
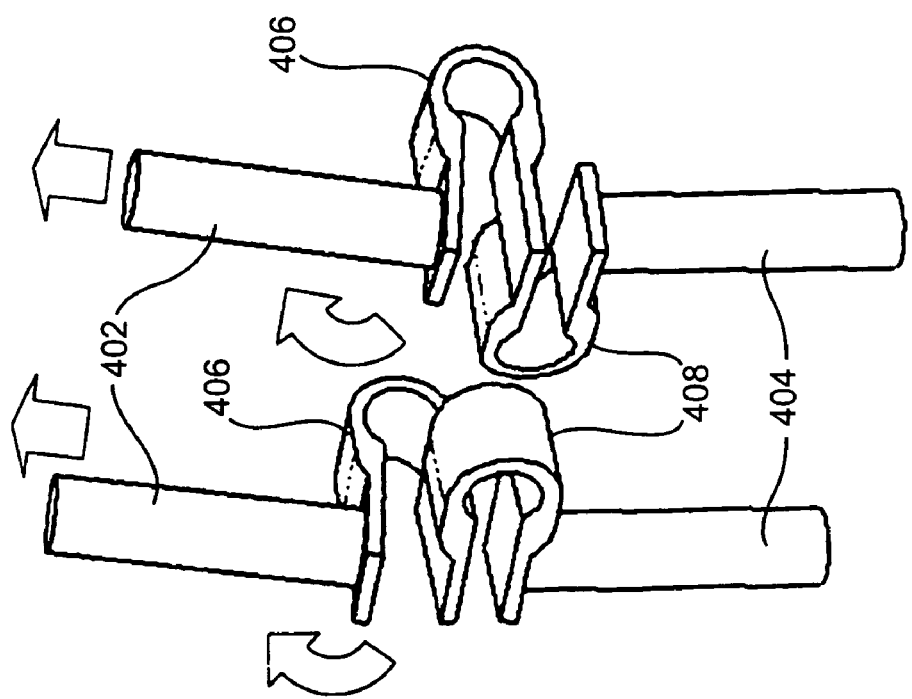
Figure 34E:
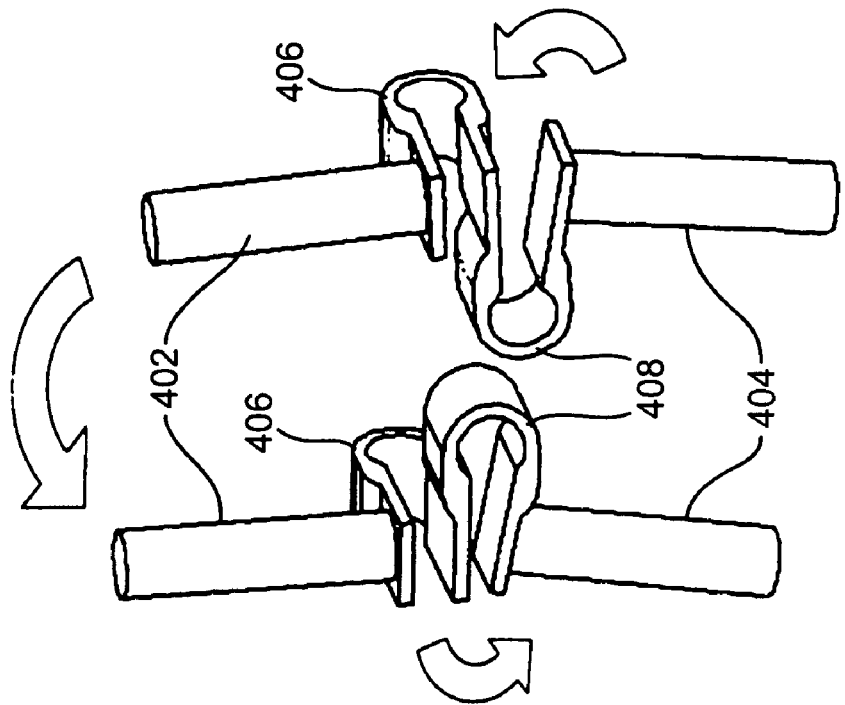
Figure 34D:
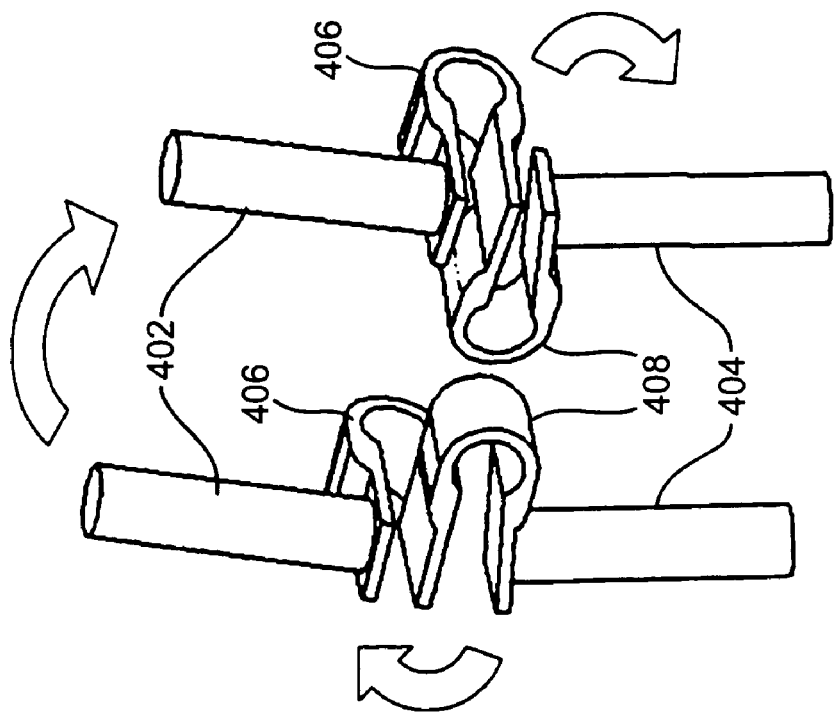

The bottom end of superior compression member 406 and the top end of inferior compression member 408 are joined together, where the gap between each pair of ends is about 2 mm to about 4 mm. Further, the stacked compression members are positioned relative to each other such that there extending bodies define an angle of at least about 4° therebetween but may be as great as about 10°, depending on the application at hand, where the greater the angle, greater degree the degree of flexibility. Preferably, however, one compression member lies within the plane defined by flexion and extension motion of the spine and the other lies within the plane defined by lateral bending motion of the spine. The role of the compression members is illustrated in FIGS. 34B-34E in which a pair of interface member is illustrated undergoing various spinal motions. For example, during flexion (FIG. 34B), the ends of both upper compression members 406 spread apart, while during extension (FIG. 34C), the ends close together. During both clockwise (right) and counter-clockwise (left) lateral bending, the lower compression members 408 are subject to compressive and extension forces, however, when the right lower compression member is under compression (FIG. 34D), the left lower compression member undergoes extension, and visa-versa (FIG. 34E).

FIGS. 36A-36C and FIGS. 37A-37C illustrate single-segment and multi-segment embodiments, respectively, of another system of the present invention. This system includes superior component 440, inferior component 450 and ligament band 460. Superior component 440 includes a base member 442 configured for receiving a screw 444 and having an anterior portion having a surface (that surface facing in the anterior direction of the spine) for placement against a portion of the superior pedicle of a vertebra. Extending downward from base 442 (rather than medially) is a post, stem or strut 446 having an elongated central portion 446a and a distal portion 446b. Inferior component 450 includes a base member 452 similarly configured to base member 442 of superior portion 440 for receiving a screw 454 and having an anterior portion having a surface (that surface facing in the anterior direction of the spine) for placement against a portion of the superior pedicle of a vertebra. Extending upward from base 452 (rather than medially) is a stem portion 456a having a distal end 456b configured to receive and engage with distal portion 446b of superior component 440. In this embodiment, engagement between the superior and inferior components is at a location centrally positioned between the two rather than at a location more distal to the superior component and more proximal to the inferior component. This arrangement provides additional balance to the system and stabilization to the treated spinal motion segment that allows flexion, extension, axial rotation and lateral bending motions which mimic that of the natural spine segment, while preventing or limiting anterior and lateral translation of the vertebrae relative to each other.

Ligament band 460 extends between the base portions of the superior and inferior components and is posteriorly positioned relative to stems 446a and 456a. However, it should be noted that the ligament band, as with any of the embodiments of the present invention, may alternatively be positioned either medially (inward) or laterally (outward) of the primary axis of the superior and inferior components.

Figure 36A:
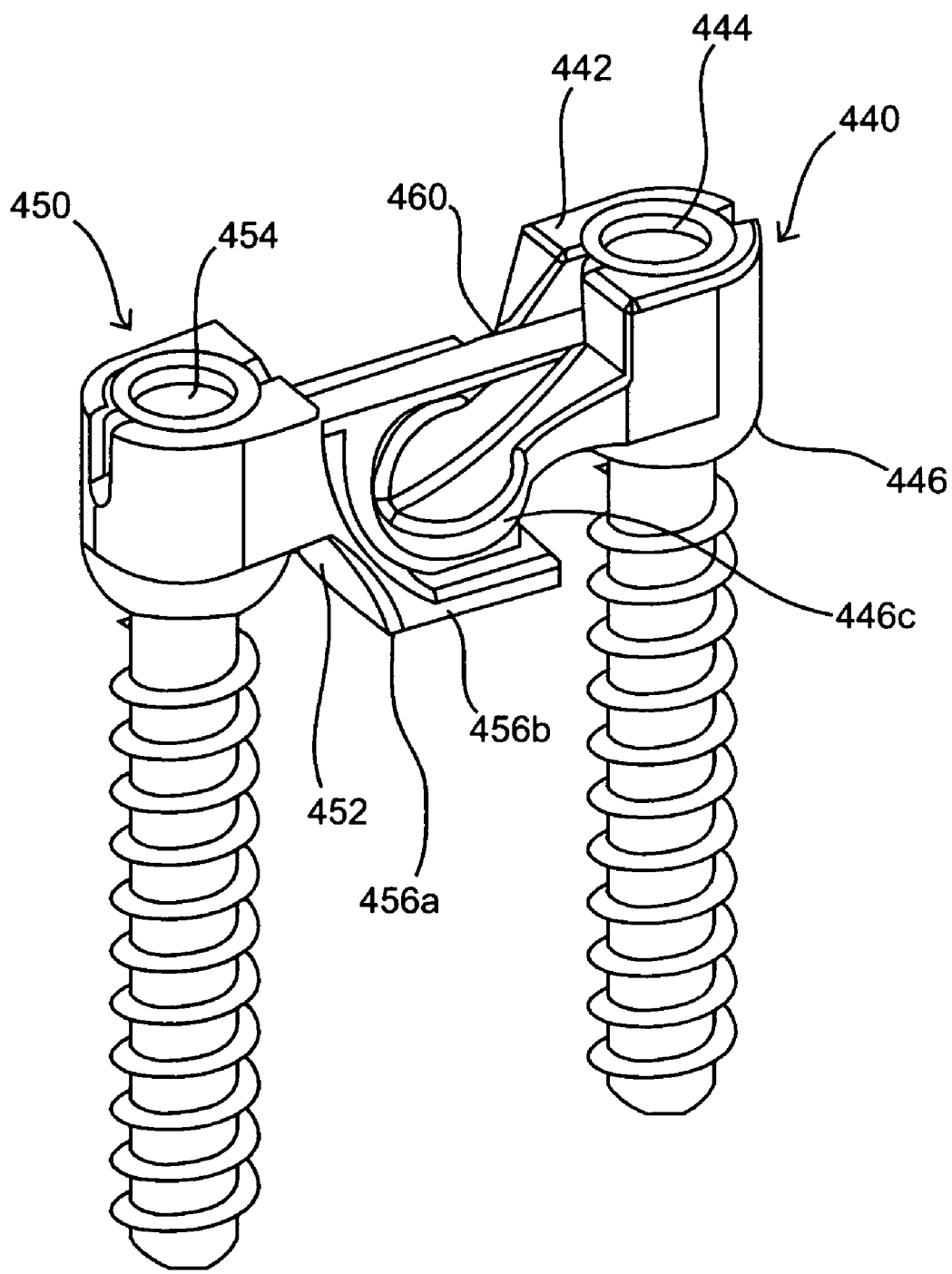
FIGS. 36A-36C illustrate perspective, side and top views, respectively, of another embodiment of a dynamic stabilization system of the present invention.
Figure 36B:
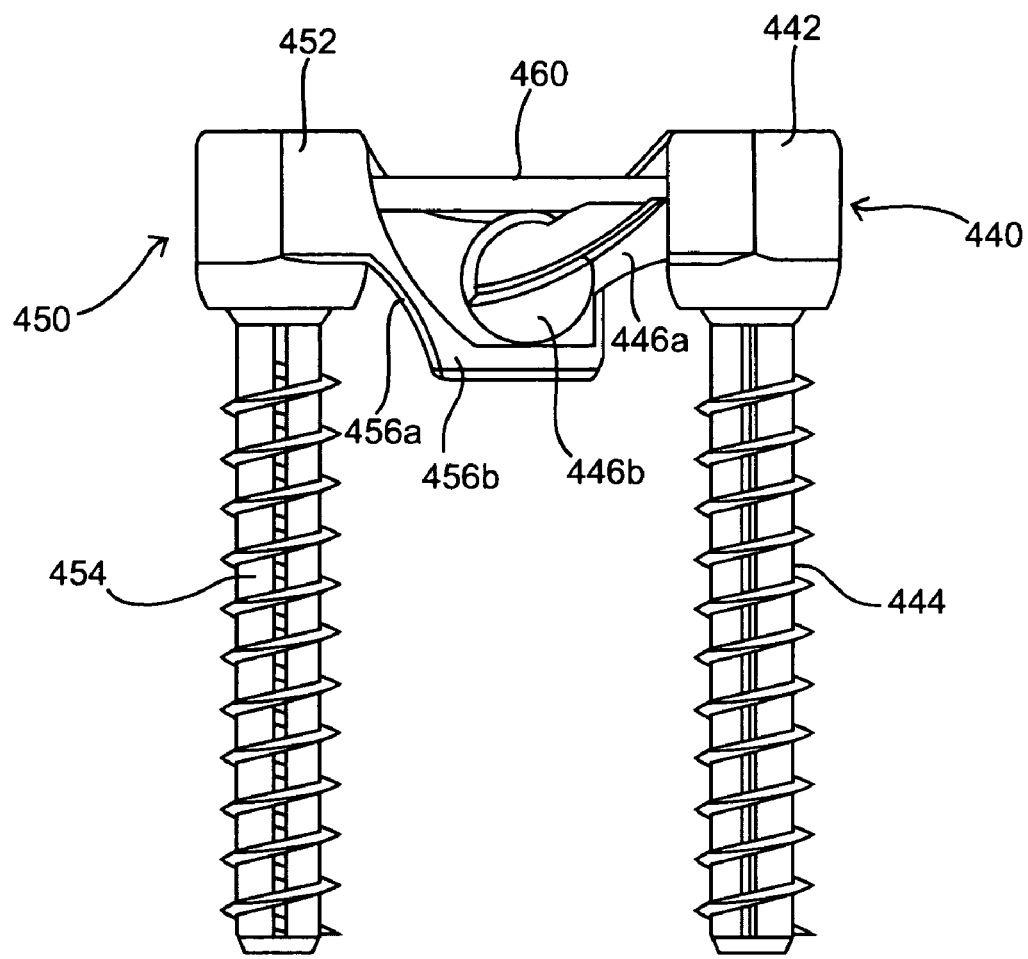
Figure 36C:
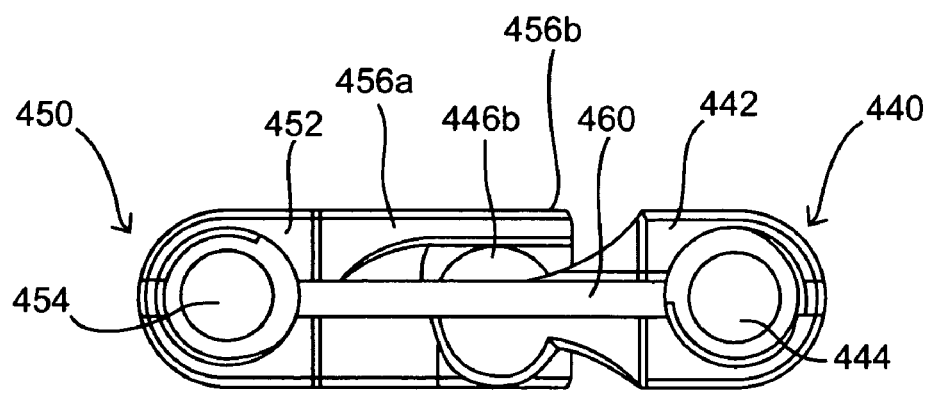
Figure 37A:
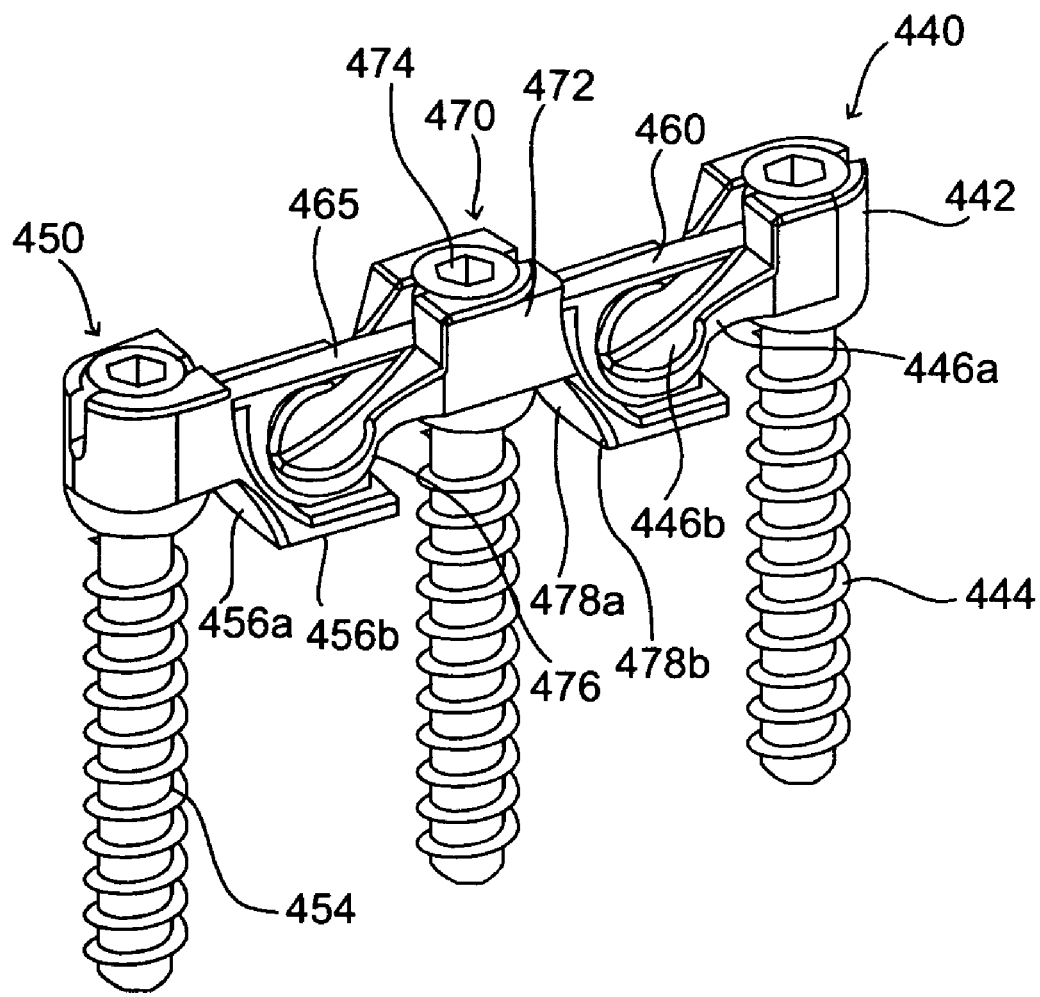
FIGS. 37A-37C illustrate perspective, side and top views, respectively, of the system of FIGS. 36A-36C in a multi-level application.
Figure 37B:
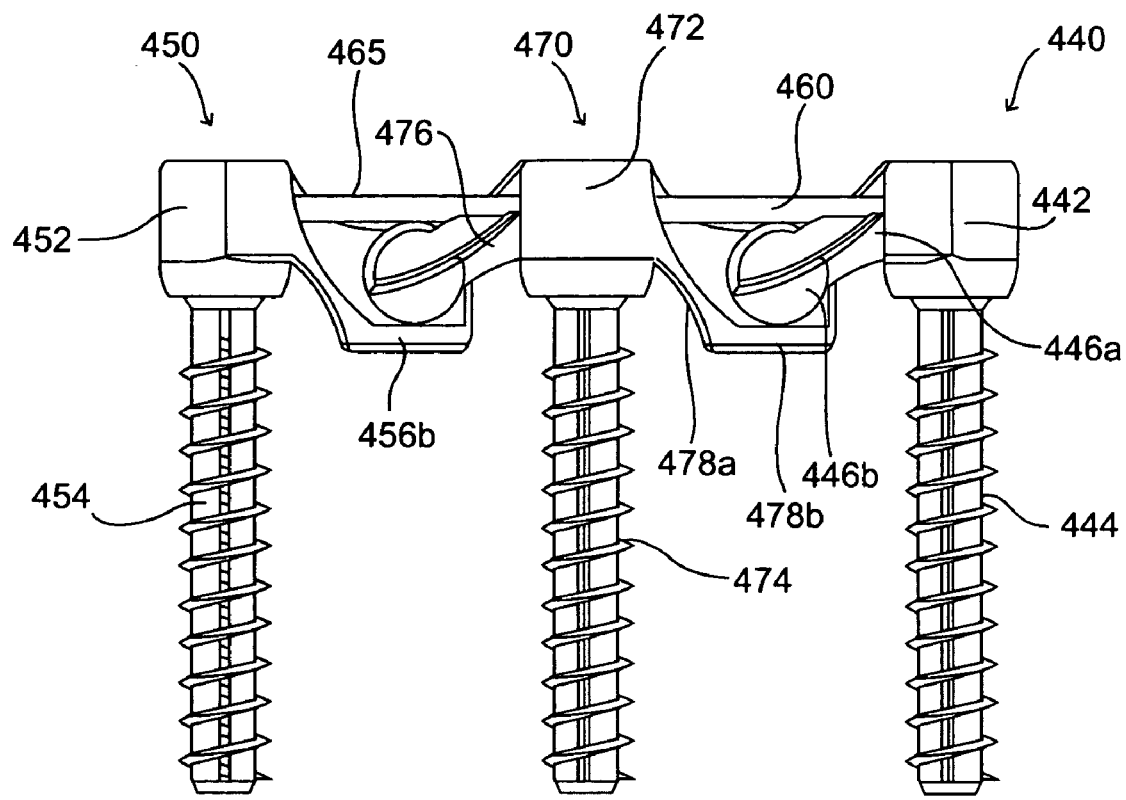
Figure 37C:
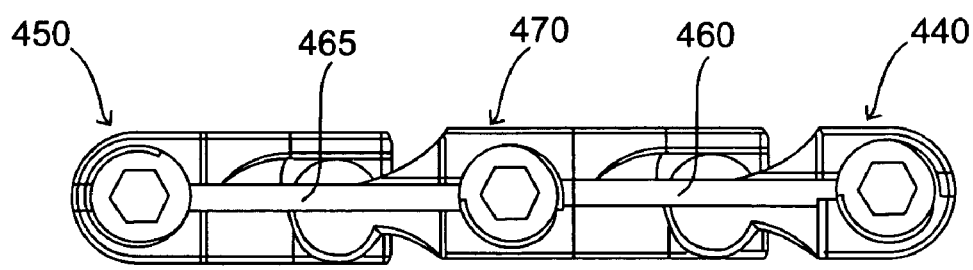

FIGS. 37A-37C illustrate the multilevel employment of the system of FIGS. 36A36C wherein a medial component 470 is employed between superior component 440 and inferior component 450. Medial component 470 includes a base 472 having a superiorly extending stem 478a having a distal end 478b configured for receiving and engaging the distal end 446b of stem 446a of superior component 440. Medial component 470 also has an inferiorly extending stem 476a having a distal end 476b which is engaged with receiving portion 456b of 456a of inferior component 450. An additional ligament band 465 is then positioned between medial component 470 and inferior component 450.

FIGS. 38A-38C and FIGS. 39A-39C illustrate single-segment and multi-segment embodiments, respectively, of another system of the present invention. This single-segment system includes superior component 480, inferior component 490 and ligament band 500. Superior component 480 includes a base member 482 configured for receiving a screw 484 and having an anterior portion having a surface (that surface facing in the anterior direction of the spine) for placement against a portion of the superior pedicle of a vertebra. Extending medially or laterally inward from base 482 (rather than downward) is a post, stem or strut 486 having an elongated central portion 486a and a distal portion 486b. Inferior component 490 includes a base member 492 configured for receiving a screw 494 and having an anterior portion having a surface (that surface facing in the anterior direction of the spine) for placement against a portion of the superior pedicle of a vertebra. Extending medially or laterally inward from base 492 (rather than upward) is a stem portion 496a having a distal end 496b configured to receive and engage with distal portion 486b of superior component 480. Ligament band 500 extends between the base portions of the superior and inferior components and is laterally (rather than posteriorly) positioned relative to stems 486a and 496a. As with the above-described embodiment, engagement between the superior and inferior components is at a location centrally positioned between the two rather than at a location more distal to the superior component and more proximal to the inferior component.

Figure 38A:
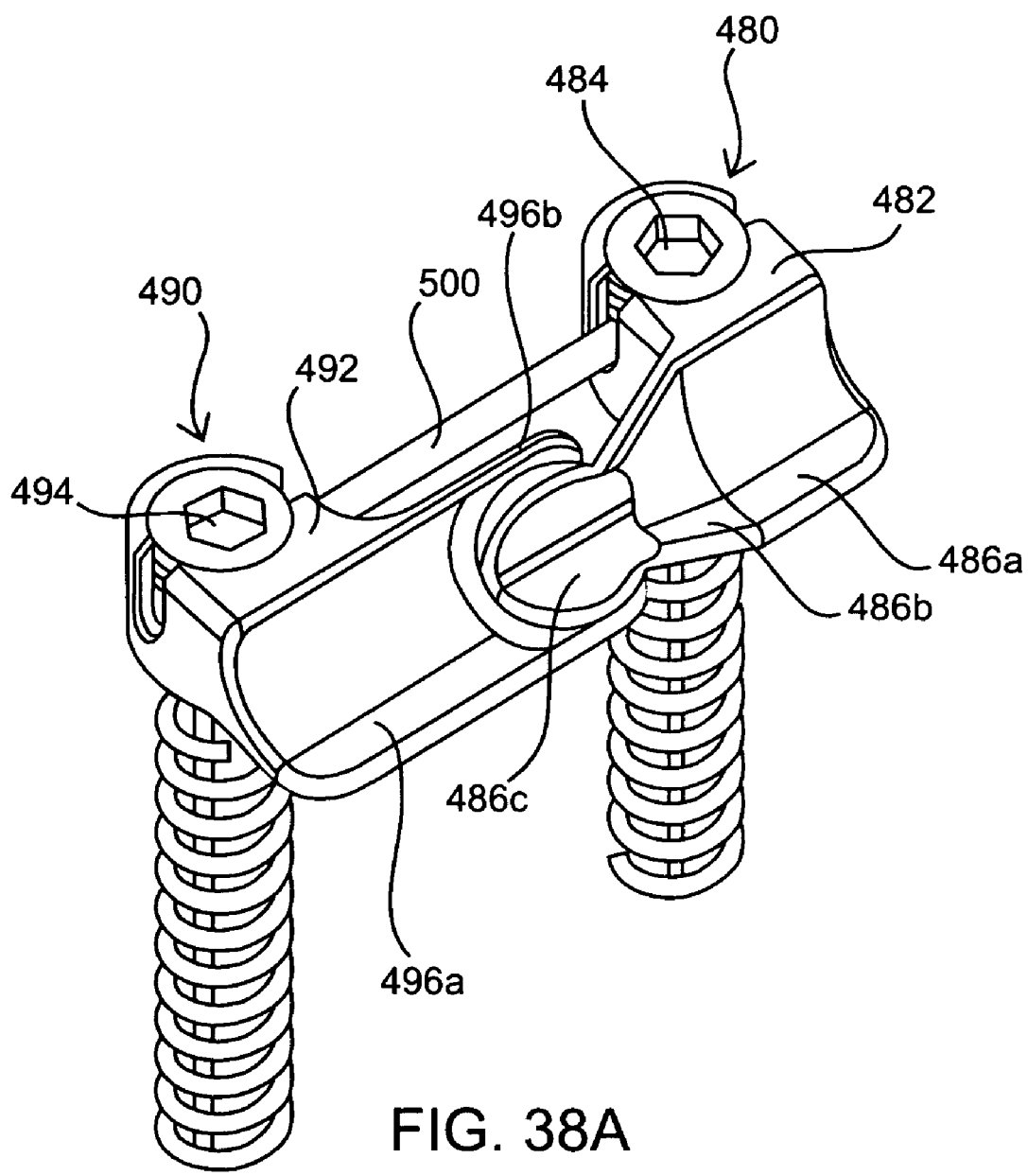
FIGS. 38A-38C illustrate perspective, side and top views, respectively, of another embodiment of a dynamic stabilization system of the present invention.
Figure 38B:
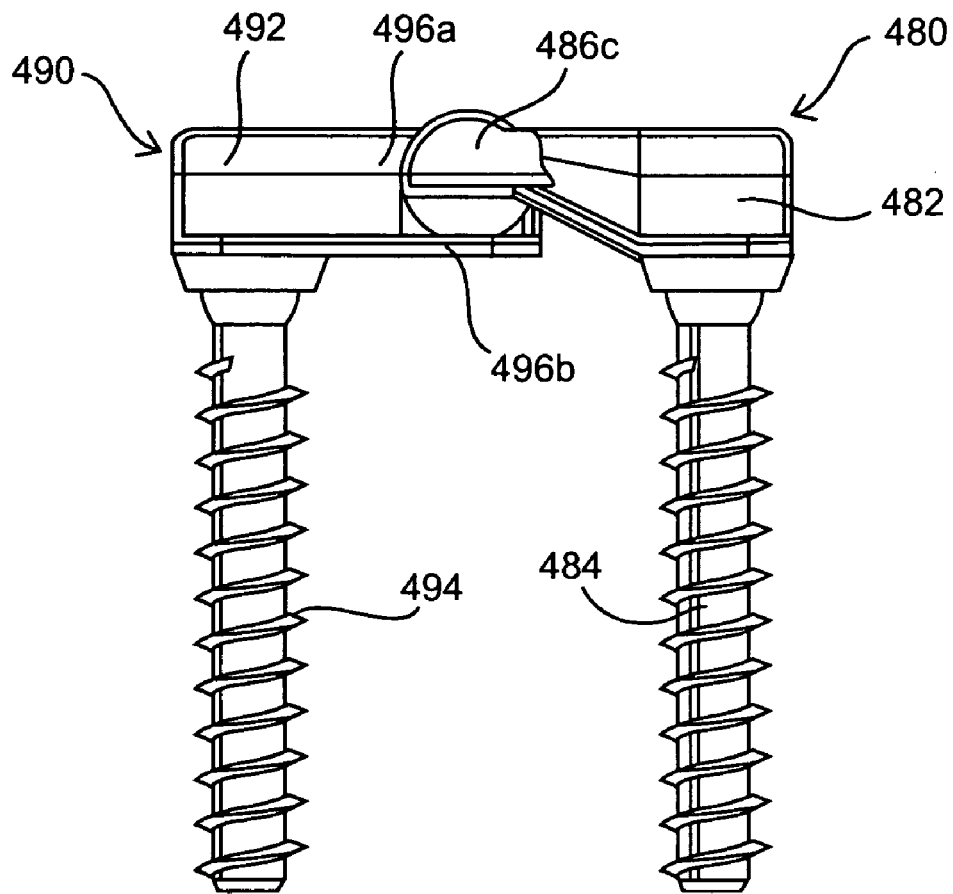
Figure 38C:
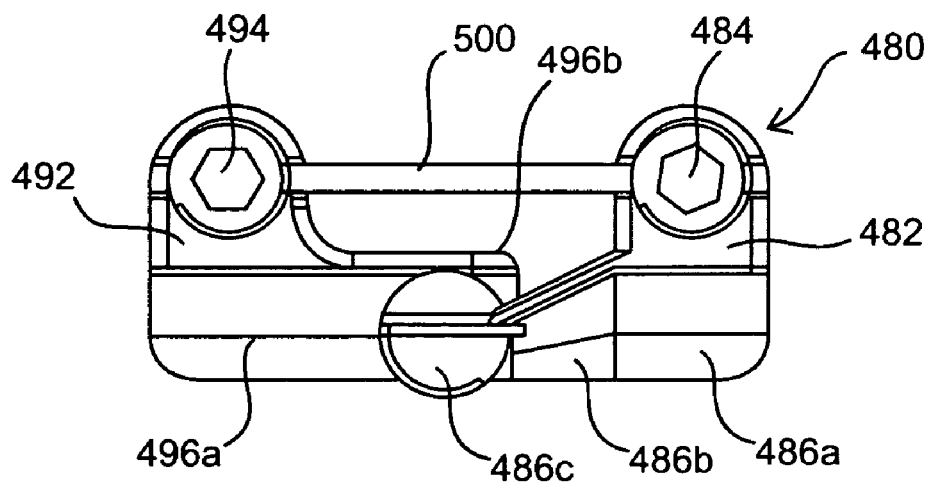
Figure 39A:
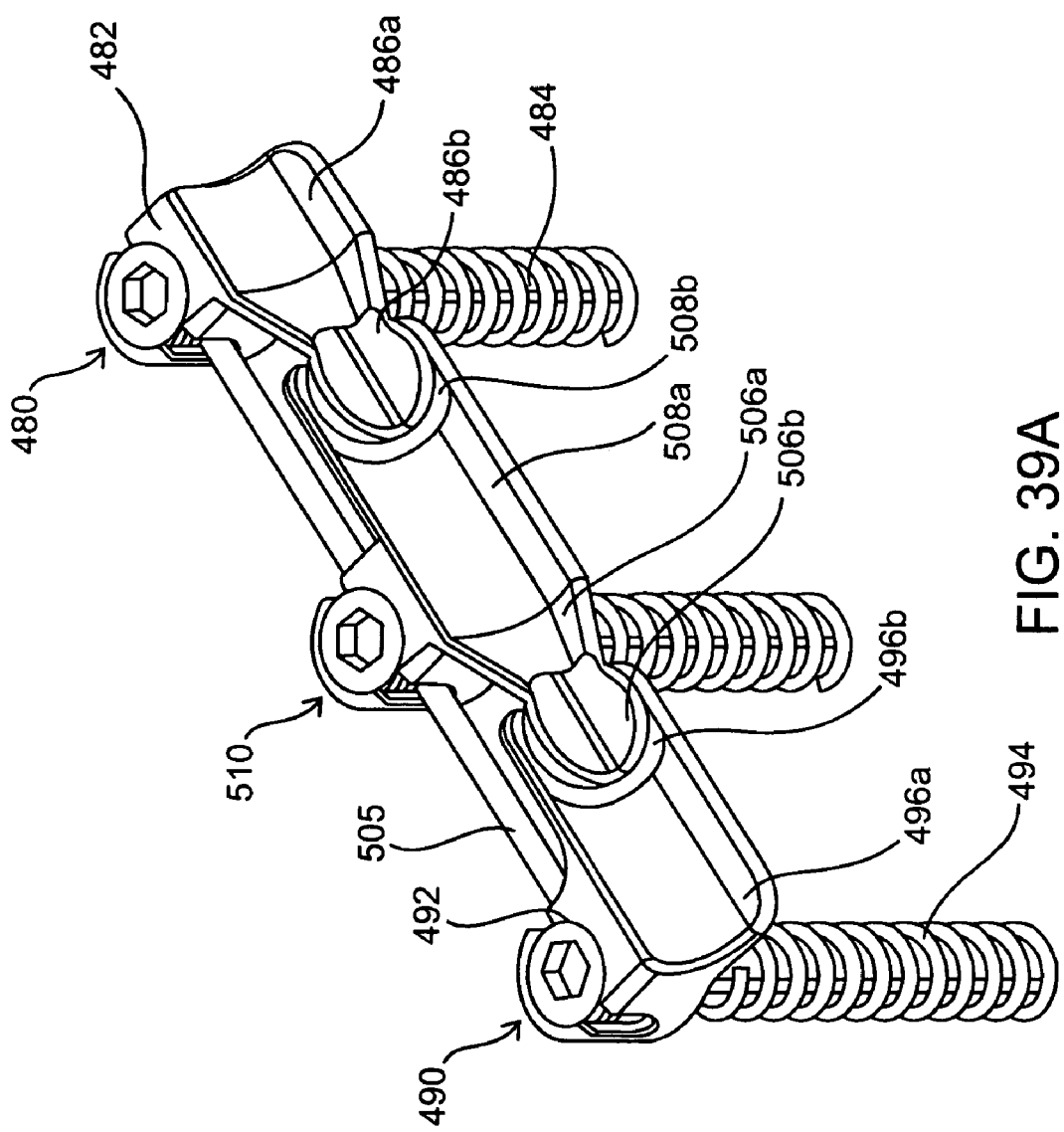
FIGS. 39A-39C illustrate perspective, side and top views, respectively, of the system of FIGS. 38A-38C in a multi-level application.
Figure 39B:
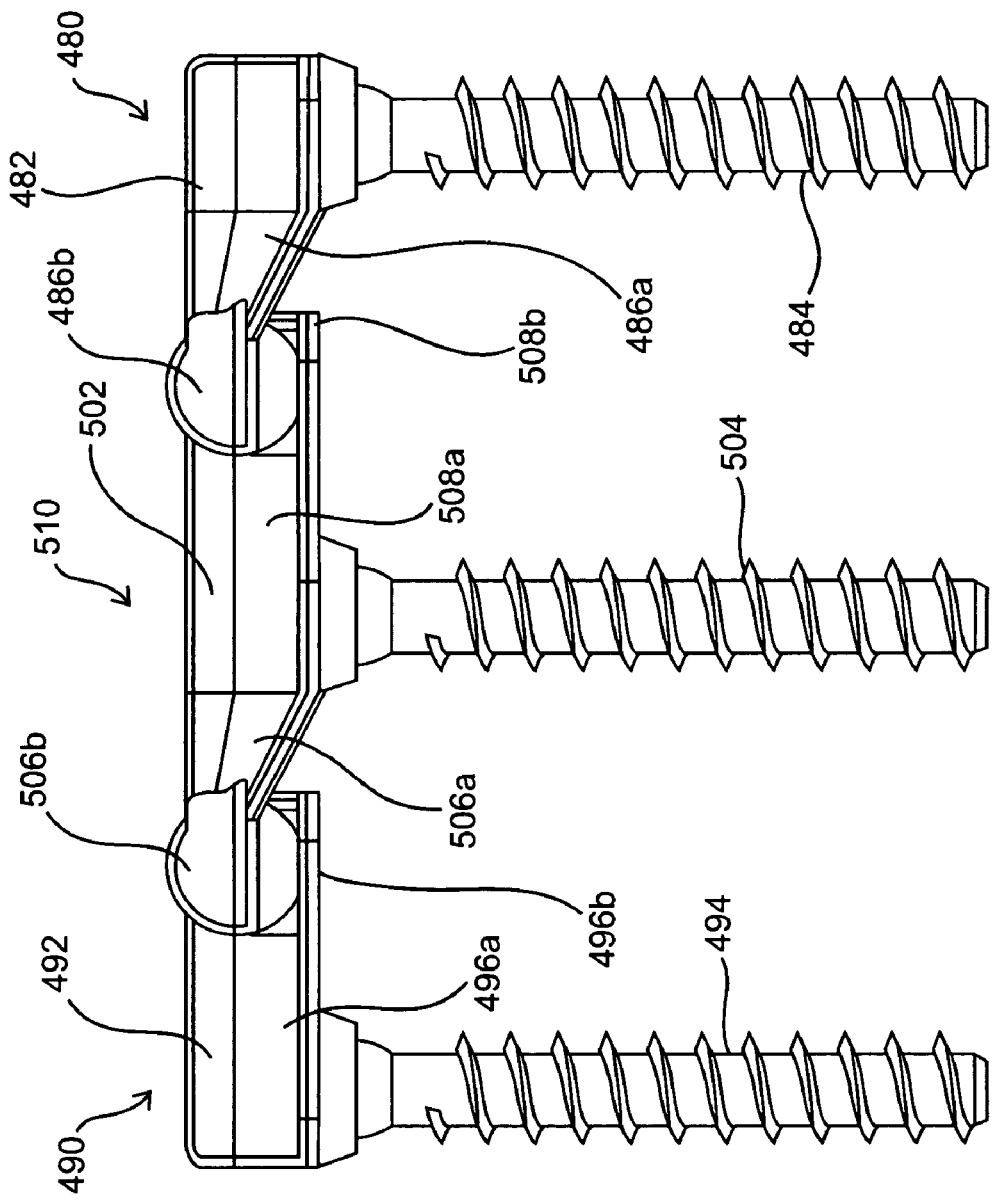
Figure 39C:
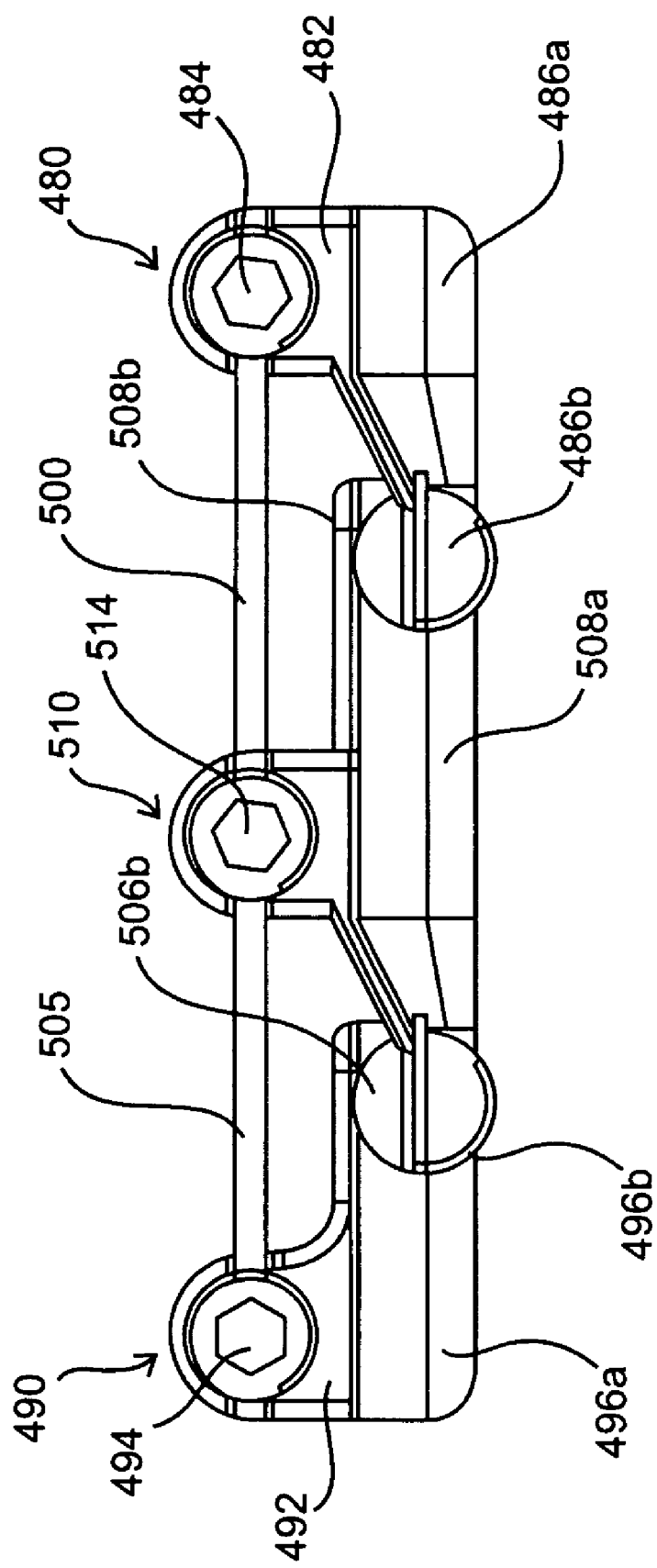

FIGS. 39A-39C illustrate the multilevel employment of the system of FIGS. 38A-38C wherein a medial component 510 is employed between superior component 480 and inferior component 490. Medial component 510 includes a base 512 having a superiorly extending stem 508a having a distal end 508b configured for receiving and engaging the distal end 486b of stem 486a of superior component 480. Medial component 510 also has an inferiorly extending stem 506a having a distal end 506b which is engaged with receiving portion 496b of stem 496a inferior component 490. An additional ligament band 505 is then positioned between medial component 510 and inferior component 490.

Figure 40B:
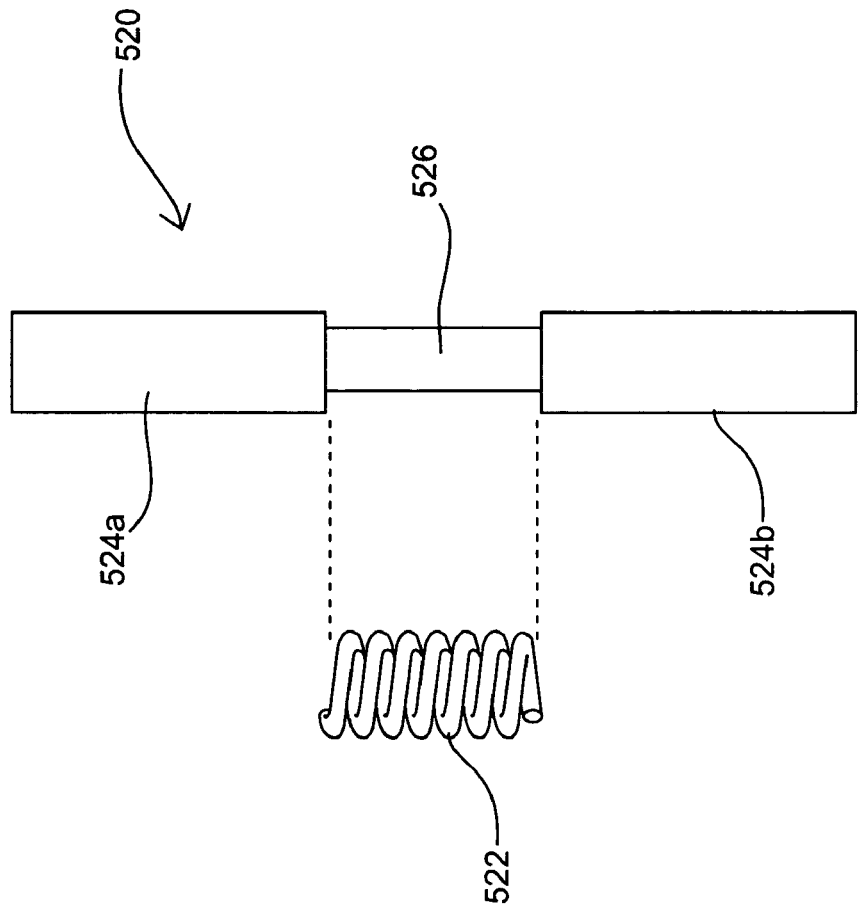
FIGS. 40A and 40B illustrate another embodiment of a strut, ligament or band usable with the systems of the present invention.
Figure 40A:
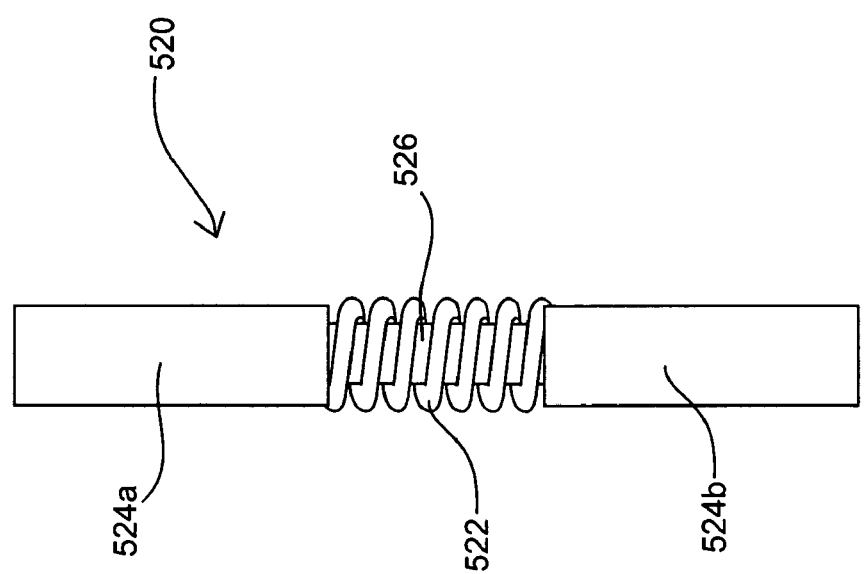

FIGS. 40A and 40B illustrate another embodiment of an interconnecting member or strut 520 similar to that of FIGS. 20A and 20B. Interconnecting member 520 includes a compression member or spring 522 extending between and affixed to cylindrically shaped superior and inferior ends 524a and 524b. As with the struts discussed above, ends 524a and 524b are fixed to superior and inferior components, respectively, by way of pins or screws. Extending within the lumen defined by spring 522 is a shock absorber 526 made of suitable material such as a polymer. Upon implant, the length of the portion of the strut between the superior and inferior components may be adjusted to accommodate the natural and/or desired vertebral spacing, and provides sufficient flexibility, compression and distraction to accommodate and facilitate spinal motion.

Figures 41A, 41B:
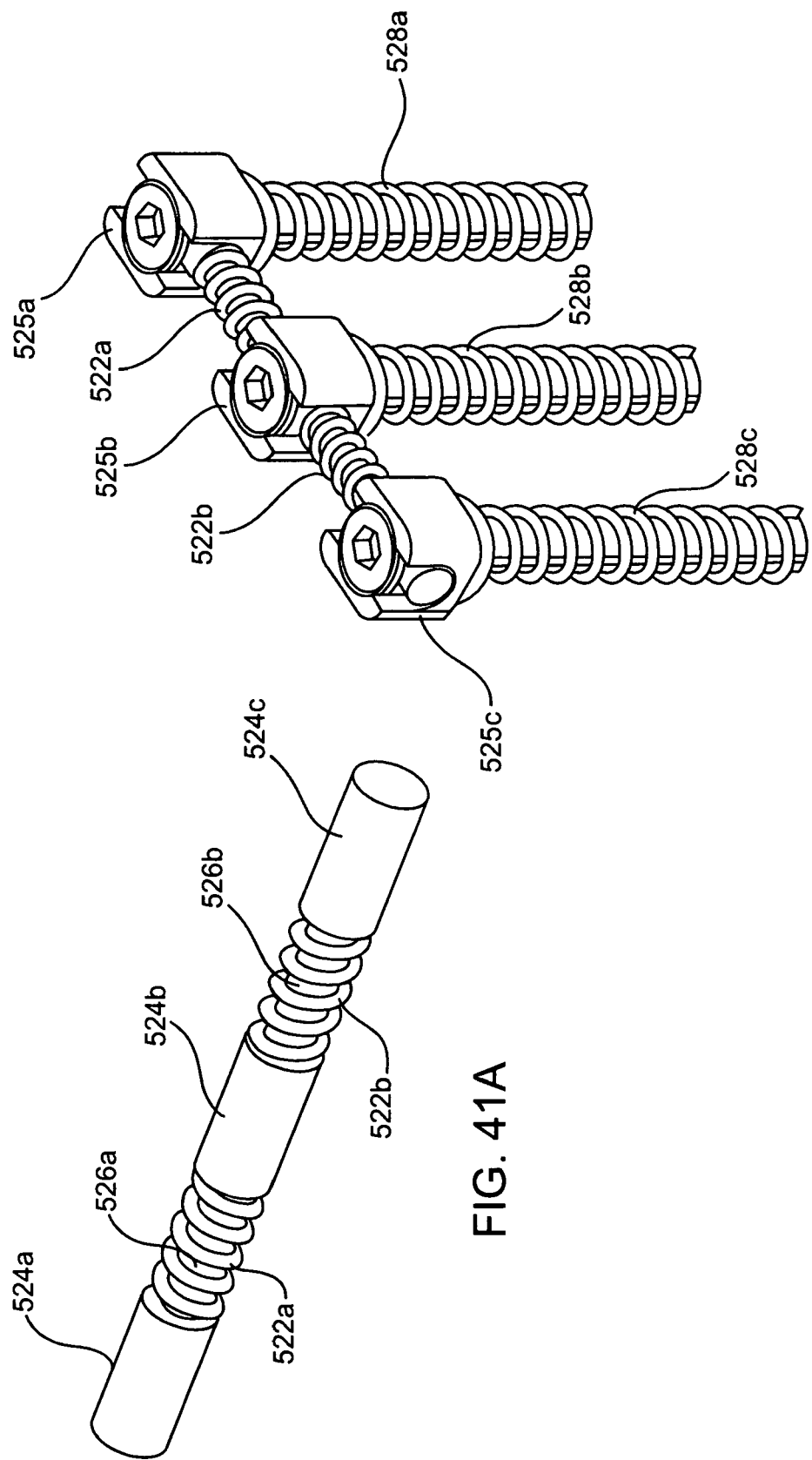
FIG. 41A illustrates a multilevel embodiment of the strut of FIGS. 40A and 40B.
FIG. 41B illustrates the multilevel strut of FIG. 41A employed within a system of the present invention.

FIG. 41A illustrates the interconnecting member of FIGS. 40A and 40B in a multilevel arrangement having superior end 524a, superior compression member 522a, central portion 524b, inferior compression member 522b and inferior end 524c. Within the cores of the compression members are shock absorbers 526a and 526b, respectively. FIG. 41B illustrates the interconnecting member employed within a multilevel stabilization system having superior component 525a having pedicle screw 528a, medial component 525b having pedicle screw 528b, and inferior component 525c having pedicle screw 528c.

Figure 42:
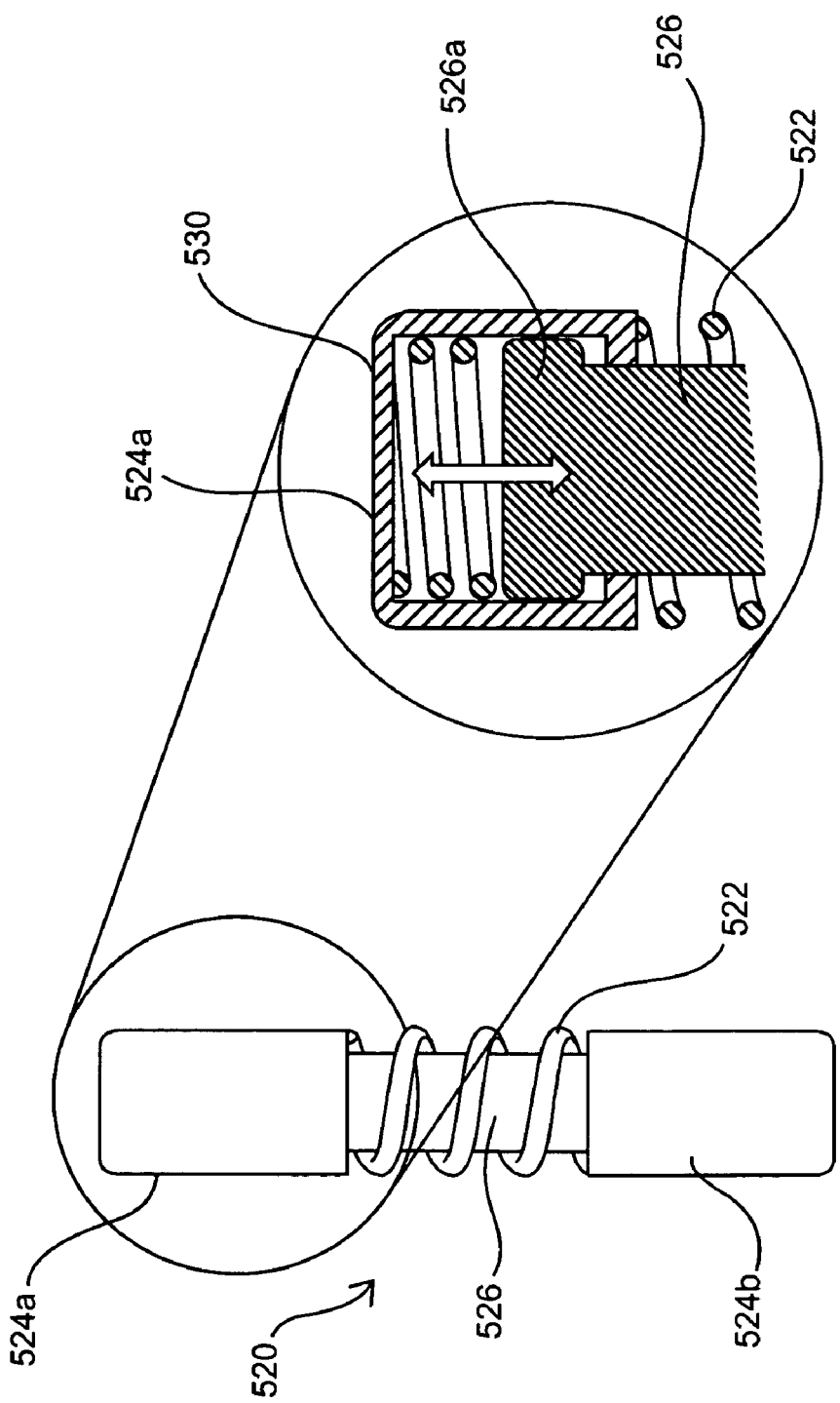
FIG. 42 illustrates an embodiment of a joint construction of the strut members of FIGS. 40A and 40B and FIGS. 41A and 41B.

FIG. 42 illustrates a possible end joint construction of the interconnecting member 520 of FIGS. 40A and 40B. Superior end 524a defines a cylindrical chamber within its walls having a distal positioned compression spring 530 sandwiched between its end wall and end 526a of polymer core 526. During extension and flexion motions, spring 522 and 530 provide the necessary compression and while polymer core 526 has very little effect on the motion. However, as polymer core 526 is stiffer than springs 522, 530, polymer core 526 dictates the extent of lateral bending and rotational movements of the spine.

Figure 43A:
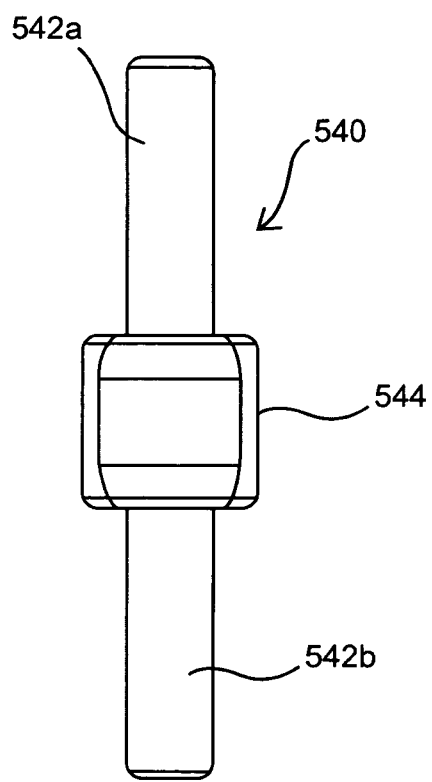
FIGS. 43A and 43B illustrate another embodiment of a strut, ligament or band usable with the systems of the present invention.
Figure 43B:
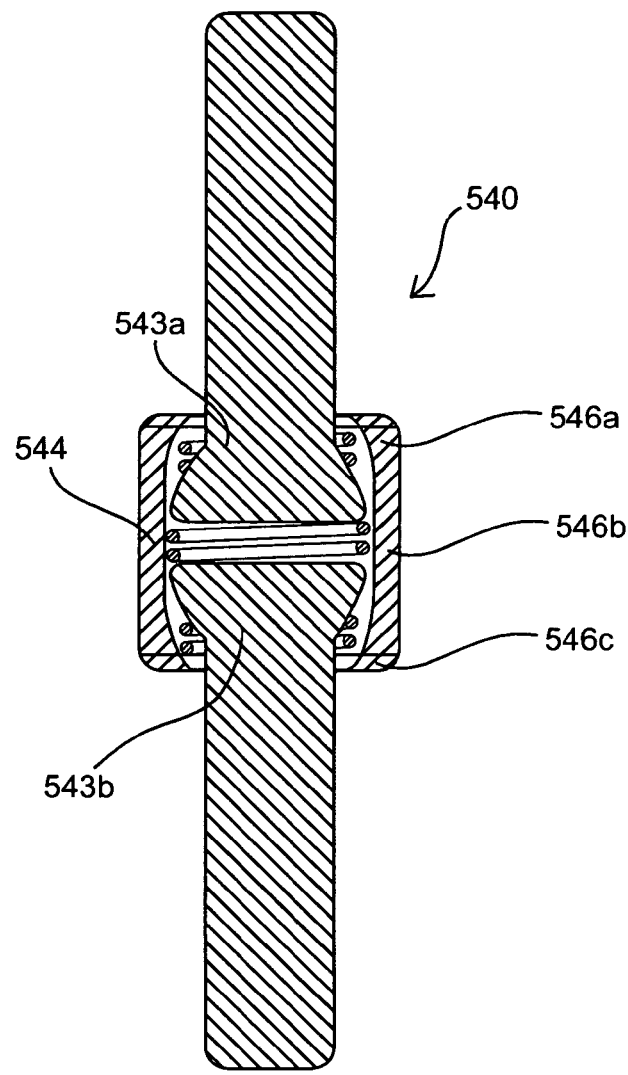
Figure 44A:
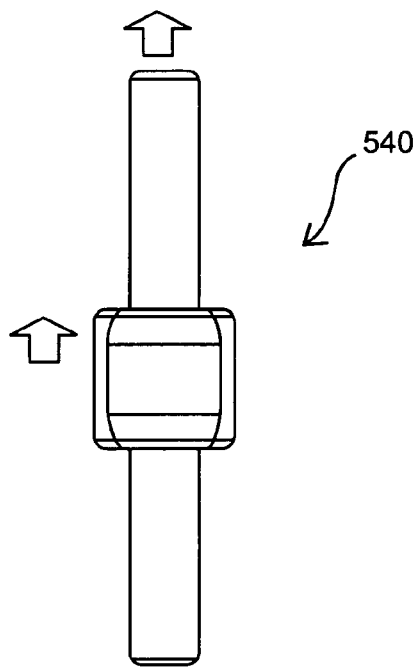
FIGS. 44A-44D illustrate the strut of FIGS. 43A and 43B undergoing flexion, extension, right lateral bending and rotational motions, respectively.
Figure 44B:
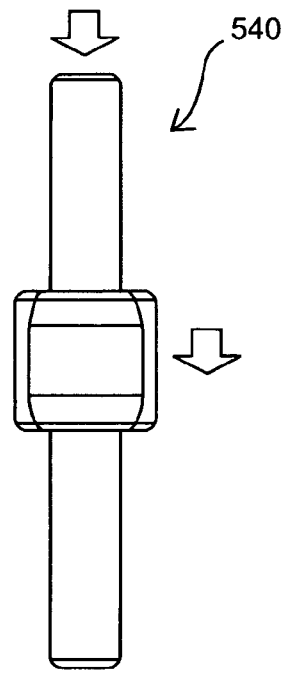
Figure 44C:
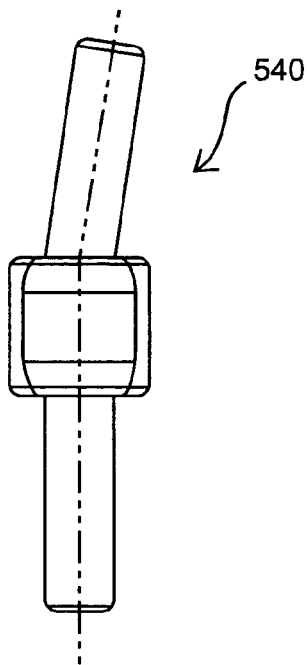
Figure 44D:
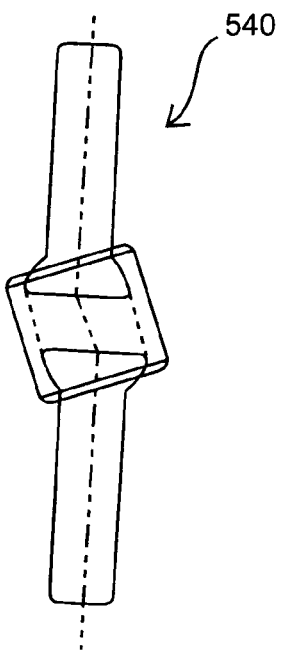

FIGS. 43A and 43B illustrate another interconnecting member 540 having central joint 544 interconnecting superior and inferior ends 542a and 542b, respectively. Ends 542a and 542b each terminate distally at bulbous end portion 543a and 543b, respectively, which are retained within joint 544. Joint 544 includes a superior compression member 546a between end portion 543a and the superior inside end of joint 544, a central compression member 546b positioned between end portions 543a and 543b, and an inferior compression member 546c positioned between end portion 543b and the inferior inside end of joint 544. An advantage of this dual ball joint configuration is that it allows rotational movement of the spine that mimics natural rotational movement of the spine, as shown in FIG. 44D, in addition to flexion, extension and lateral bending movements, as illustrated in FIGS. 44A, 44B and 44C, respectively.

FIG. 45A illustrates a multilevel application of the interconnecting member of FIGS. 43A and 43B. Interconnecting member 550 has superior end 552a, superior joint 554a, central portion 552b, inferior compression member 554b and inferior end 552c. FIG. 45B illustrates interconnecting member 550 employed within a multilevel stabilization system having superior component 560a having pedicle screw 528a, medial component 560b having pedicle screw 562b, and inferior component 560c having pedicle screw 562c.

FIGS. 46A and 46B illustrate the joint of FIGS. 43A and 43B employed as end joints 572a, 572b of interconnecting member 570 which includes a strut 576 terminating in superior and inferior ends 574a, 574b, respectively, having ball configurations. Each ball end is positioned between an outer spring 578a, 578b and an inner spring 580a, 580b, respectively, which are retained within the walls of joint 572a, 572b, respectively. As illustrated in FIG. 46A, interconnecting member 570 is employed in a dynamic stabilization system having superior component 582a having pedicle screw 584a and having inferior component 582b having pedicle screw 584b.

Figure 47A:
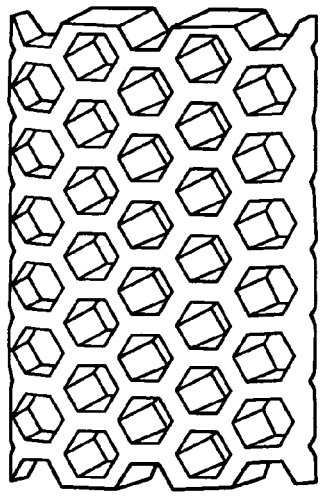
FIG. 47A illustrates a materials having honeycomb configurations suitable for use with an interconnecting member of the present invention.
Figure 47B:
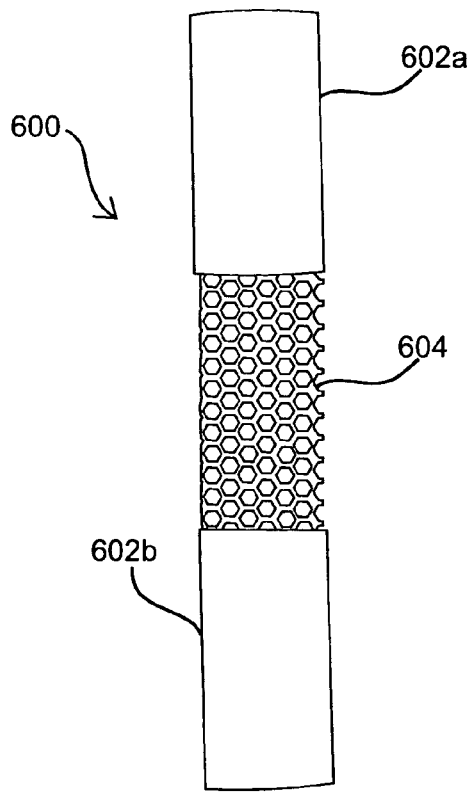
FIGS. 47B and 47C illustrate interconnecting members employing the material of FIG. 47A.
Figure 47C:
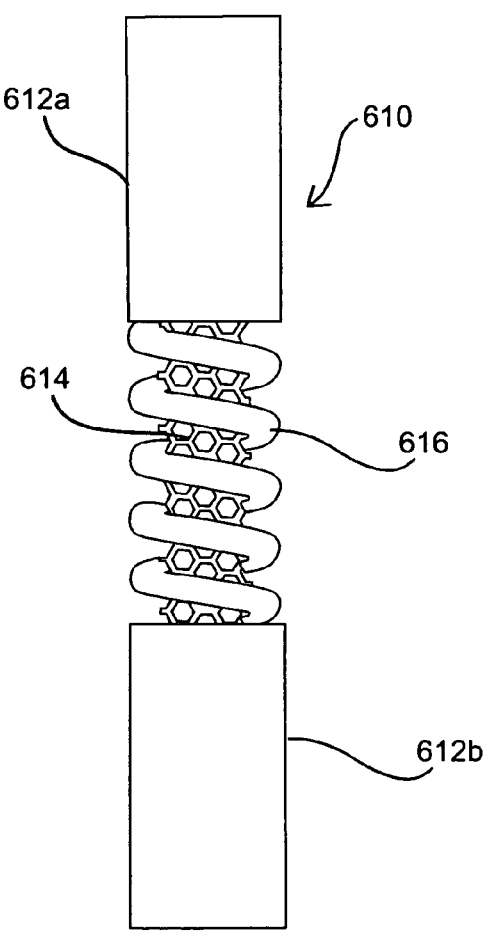
Figure 51A:
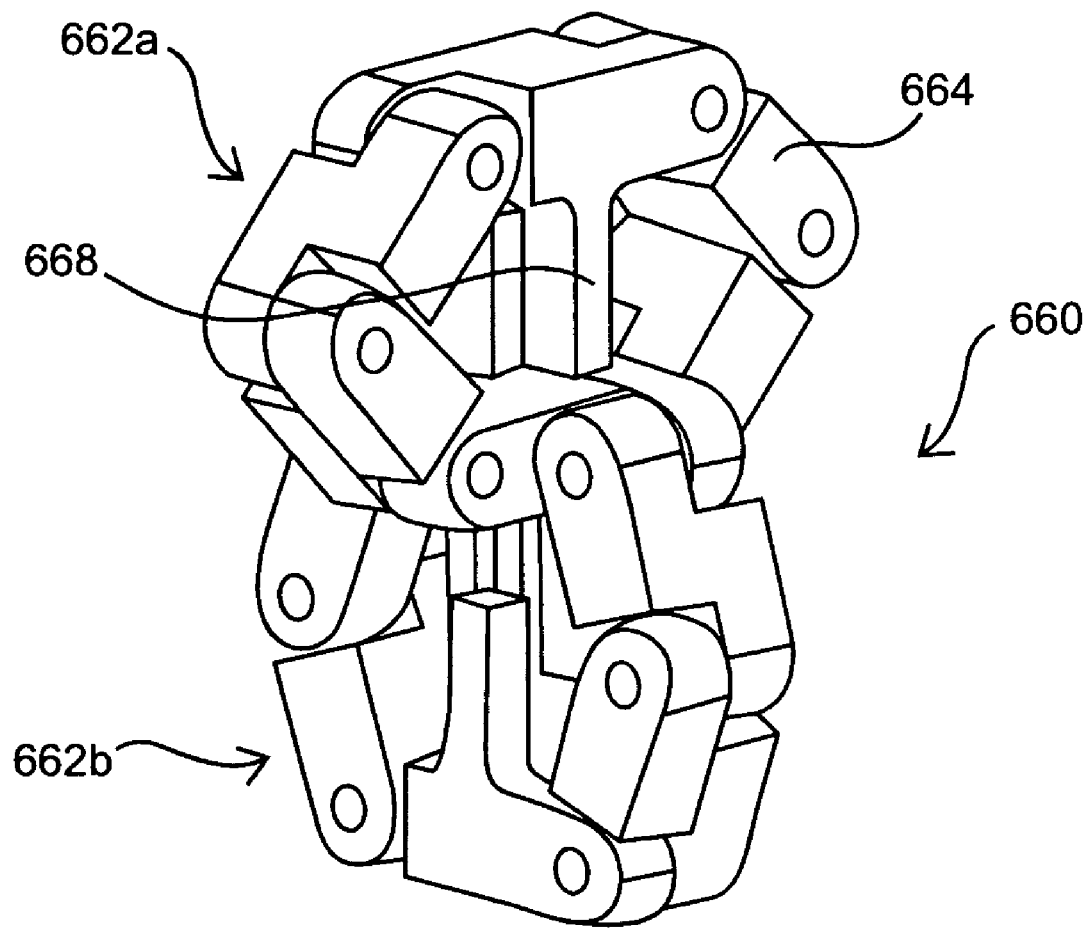
FIG. 51A illustrates another embodiment of compression structure which may be employed with the interconnecting members of the present invention.
Figure 51D:
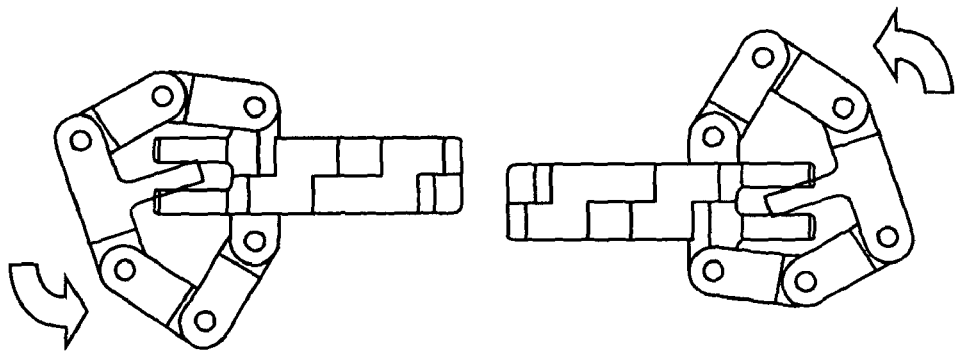
FIGS. 51B, 51C and 51D illustrate the compression structure of FIG. 51A in flexion, extension and lateral bending motions, respectively.
Figure 51C:
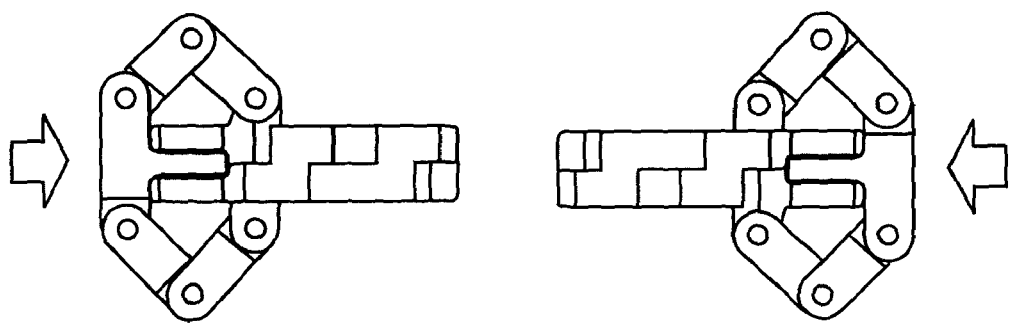
Figure 51B:
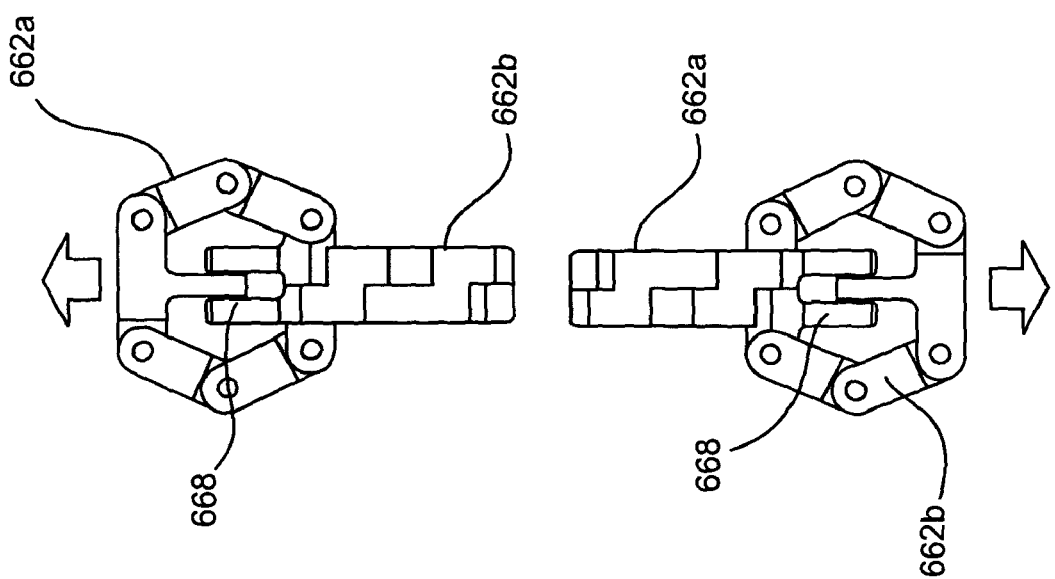

In addition to springs and the like, the present invention further provides for interconnecting members and struts made of other materials and having alternate configurations. For example, FIG. 47A illustrates a polymeric material 590 having a honeycomb structure. Such a structure is ideally suited for use with the interconnecting members of the present invention due its natural compression characteristics. The entire length or a portion thereof, as illustrated in FIG. 47B, may be comprised of the honeycomb structure. Here, interconnecting strut 600 has a central portion comprised of the honeycomb structure which extends between end portions 602a, 602b. FIG. 47C shows a variation of an interconnecting member 610 having a central honeycomb structure 614 extending between end portions 612a, 612b and further having another compression component in the form of spring 614 about the polymeric core 616.

FIG. 48A illustrates a polymeric material 620 having a two-part honeycomb structure in which the honeycomb cells of a top portion 622 are at substantially right angles (or some other angle) to the honeycomb cells of the bottom portion 624. As illustrated in FIG. 48B, the honeycomb structure of FIG. 48A is employed in s a central portion 628 of interconnecting strut 626 having end rigid or solid end portions 630a and 630b. FIG. 48C shows a variation of an interconnecting member 632 having a central honeycomb structure 634 extending between end portions 632a, 632b and further having another compression component in the form of spring 636 about the polymeric core 634.

FIGS. 49A and 49B illustrate another interconnecting strut 640 of the present invention employing a fiber bundle 646 as a compression member extending between rigid ends 642a and 642b. Under compression, as illustrated in FIG. 49B, the fibers bow radially outward. FIG. 50 illustrates a variation of a fiber compression member 654 extending between rigid end portions 652a and 652b of interconnecting strut 650. Here, stays 656 are used circumferentially about fiber bundle 654 to provide additional stability to the compression member.

Figure 52:
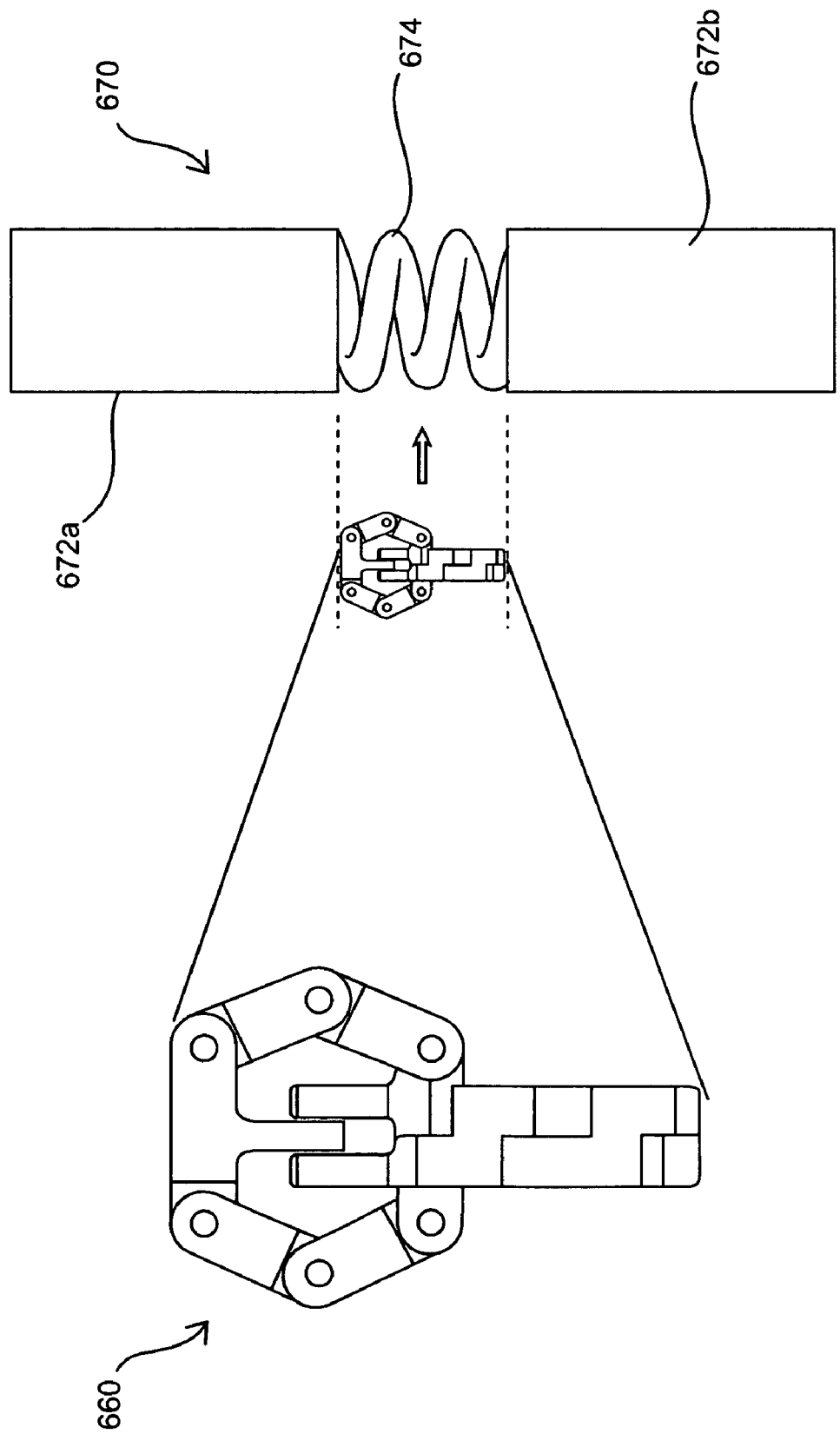
FIG. 52 illustrates another interconnecting strut of the present invention utilizing the compression structure of FIG. 51A.

FIG. 51 illustrates another structure 660 suitable for use as a compression member for the interconnecting struts of the present invention. Structure 660 includes two interconnected components 662a, 662b each comprises of interconnected moving links 664. Within each component 662a, 662b is a tongue and groove mating structure 668 which limits and controls the degree or extent of motion undergone by that component. For example, during flexion motion, as illustrated in FIG. 51B, both components 662a, 662b extend axially until their respective motion limiting structures 668 are fully extended. During extension motion, as illustrated in FIG. 51C, both components 662a, 662b compress radially until their respective motion limiting structures 668 are fully engaged. During lateral bending motion, as illustrated in FIG. 51D, both components 662a, 662b rotate laterally, but in opposite directions until their respective motion limiting structures 668 have reached their full angular rotation. As such, structure 660 may be employed as a compression member within an interconnecting strut 670, as illustrated in FIG. 52. Here structure 660 is positioned centrally at its ends between end portions 672a and 672b and within a secondary compression member or spring 674.

Figure 53A:
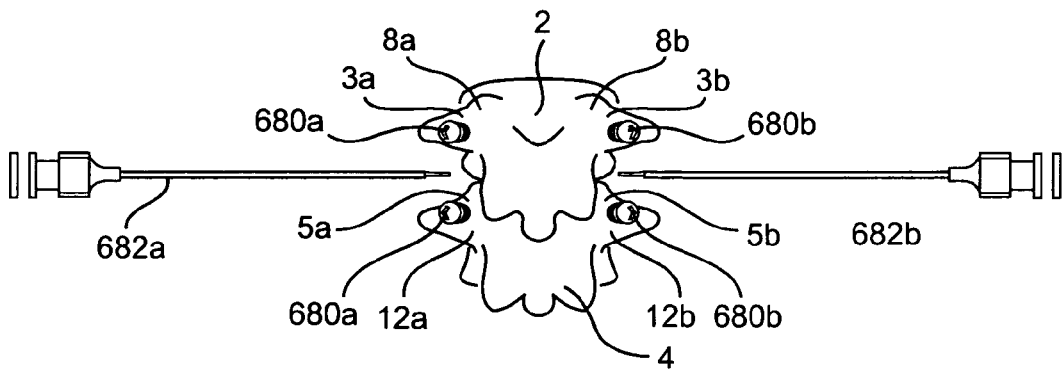
FIGS. 53A-53C illustrate the steps of implanting a dynamic stabilization system of the present invention employing balloon type interconnecting struts.
Figure 53B:
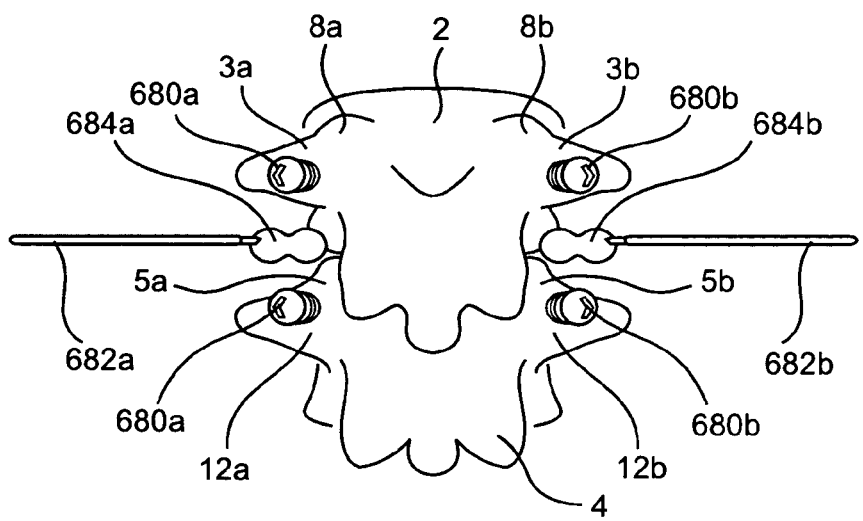
Figure 53C:
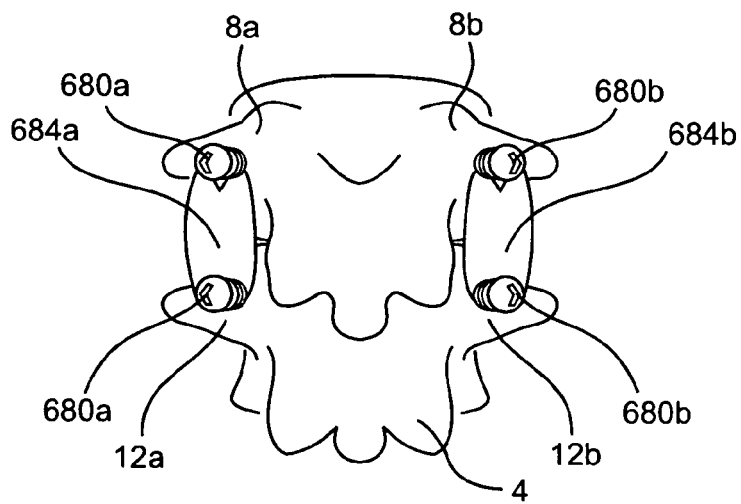

FIGS. 53A-53C illustrate another dynamic stabilization system of the present invention which is implantable in a minimally invasive manner. The system includes an expandable member (or two if doing a bilateral approach) 684a, 684b which may take the form of a compliant or non-compliant balloon which is fillable with an inflation or expansion medium, such as air, saline or a flowable, curable fluid. Each balloon 684a,b is configured to engage with and extend between a pair of pedicle screws 680 that are inserted into the pedicle 3a,b of the superior facet joint 8a,b of superior vertebra 2 and into the pedicle 5a,b of the superior facet joint 12a,b of inferior vertebra 4.

As illustrated in FIG. 53A, using a bilateral approach (although an ipsalateral approach may also be used), pedicle screws 680a,b are inserted into the superior facet joints. Subsequently, cannulas 682a and 682b are inserted on opposing sides of the spinal motion segment being treated. Balloons 684a and 684b are then simultaneously or serially delivered through a respective cannula to between the designated pedicle screws. Once positioned, the balloons are expanded by way of inflation lumens within the respective cannula until the desired level of distraction is achieved between vertebrae 2 and 4. The cannulas may then be removed from the operative field.

The pedicle screws used with the present invention may have any suitable configuration, size and length. For example, the screws may have a polyaxial configuration, as is commonly used in affixing implanted devices within the spine—e.g., rods and plates for fusion. These types of screw allow for customizing the position of the implants for the particular spinal anatomy. While conventional pedicle screws are suitable for use with the systems of the present invention, use of such screws may result in complications when used with dynamic stabilization systems that may not otherwise occur with fusion based systems since the former allows motion which, when repetitive, may result in complications at the screw bone interface, along the screw itself, or at the screw rod interface. To circumvent this problem, the present invention also provides a novel pedicle screw for use with the subject systems.

Such a pedicle screw is illustrated in FIGS. 35A and 35B. Pedicle screw 420 includes an outer screw member 422 and an inner screw member 424. Outer screw member 422 has a fixed proximal portion 422a and an expandable distal portion 422b which includes a plurality of expandable petals or segments. The segments are each interconnected to proximal portion 422a by a hinge segment 426. The external surfaces of both the proximal and distal portions of outer member 422 are threaded along their lengths for anchoring within the vertebral body. The internal surface 428 of the proximal portion 422a is also threaded but with a tighter pitch to threadably receive inner screw member 424. The internal surface 430 of distal portion 422b, however, is not threaded but distally tapers. Inner screw member 424 has a threaded proximal portion 424a and an unthreaded distal portion 424b. Outer screw member 422 has an internal diameter and inner screw member 424 has outer diameter such that inner screw member 424 is insertable or threaded into the open proximal end of outer screw member 422. Upon distal translation of inner screw member 424 into outer screw member 422, the distal end of distal portion 424b abuts the tapered interior walls 430 of the distal portion of outer screw member 422 and flares or dilates the petal segments of outer screw distal portion 422b radially outward and into the bony structure into which it is implanted. The radial anchoring of the screw enables it to better resist loosening as the result of repetitive motions of the system components.

The subject devices and systems may be provided in the form of a kit which includes at least one left-right pair of components of the above described dynamic stabilization systems. As numerous applications require the treatment of more than one spinal segment or unit, the subject kits may include as many sets of components of the subject systems that may be used to treat the application hand. Typically, however, no more than about two to three sets are implanted in any one surgical application. The kits may further include pedicle screws for securing the above-described systems to the vertebral bodies as well as other instrumentation for implanting the systems. The screws may be pre-fixed to the respective superior and inferior components, or may be provided separate from these components and subsequently fixed to the components upon implantation into the vertebrae. Instructions for implanting the various devices and systems may also be provided with the kits. Such instructions may included, for example, the manner in which the interconnecting members of the system components are secured to the respective base members, and may further provide protocols in determining the most suitable length, stiffness/flexibility, shape or the compressive/distractive forces imposed on a strut member of the various system, and making adjustments to these characteristics accordingly.

The devices and systems of the present invention may be implanted through open surgical approaches, minimally invasive approaches as well as percutaneous approaches. Generally, open placement or implantation of pedicle screw-based systems involves dissection of the posterior elements of the affected spinal segments—including the lamina, the spinous process, facet complex, and transverse processes. However, removal of some or all of these parts may not be necessary and is determined by the physician on a case-by-case basis.

In an open procedure, an entry point adjacent to the junction of the transverse process and the pars interarticularis, for each of the pedicle screws of the subject system is drilled. After an entry point is defined, a probe is placed into the pedicle to define the trajectory or angle at which the drill hole is to be formed. Once the desired trajectory is selected, a screw channel is drilled. Each of the system components (typically at least one of the left and right superior components and at least one of the left and right inferior components) is positioned accordingly and a pedicle screw is inserted through the pedicle screw bore within each of the components and into the formed channel.

A percutaneous approach to implanting the subject systems is accomplished by first placing a Kirschner wire within the target pedicle to define the trajectory of the channel to be formed therein. Using a cannulated tap which is translated over the wire, the channel is formed. A cannulated pedicle screw is then placed over the Kirschner wire and delivered inserted through the pedicle screw bore within each of the components and into the formed channel. The lumens of the cannulated screws may be injected with methylmethacrylate or hydroxyappetite to further secure the screw within the vertebrae. It should be noted that any or all of the steps of a minimally invasive or percutaneous approach may be facilitated by endoscopy or fluoroscopy.

With any approach, e.g., open, minimally invasive or percutaneous approach, after insertion of the pedicle screws, the dorsal portion of the dynamic stabilization system is inserted. The engagement between the system components and their respective screws may be accomplished in one of two ways. The connection between the screw and the system components may be prefabricated where the two are provided as an integral unit or the screws may be provided as modular components discrete from the system components.

For systems in which the length, stiffness, shape and/or positioning of the interface or strut member are not adjustable, fixation of the superior and inferior components to the vertebrae on both the left and right sides of the spinal motion segment substantially completes the implantation procedure. For those systems including such an adjustable interconnecting or strut member, the member is engaged with the superior and inferior components (as described above in the respective descriptions of these various systems) and its length, stiffness, shape and/or position is adjusted accordingly. A separate tool may be used to facilitate the adjustments. For example, a device may be employed to selectively tighten he strut segments of the systems of FIGS. 17-19. After the strut characteristics and features are confirmed, the strut is locked into place.

For embodiments of the present invention involving the use of ligament or extension band, such as the embodiments of FIGS. 8-12 and 16, the ligament or band may be implanted and adjustably (in certain variations) coupled with the superior and inferior components by means of the pedicle screw as discussed above. The length or amount of traction/distraction which is placed on the components by the ligament may be selected and adjusted either prior to implantation of the system or subsequently to implantation. In either case, an end portion of the tension band may be cut to size. The proximal end of the ligament is inserted into the superior or rostral component and the distal end of the inferior or dorsal component is inserted into the inferior or dorsal component. Before securing the ends of the ligament, the ligament may be distracted a selected amount by pulling on one or both of the ligament ends. While distracted or stretched, the ends are secured and locked into place by insertion or further tightening of the pedicle screws with the respective components.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A system for stabilizing at least one spinal motion segment comprising a superior vertebra and an inferior vertebra, the system comprising:
    a left and a right superior bone anchor configured to couple to the superior vertebra, each superior bone anchor comprising a first strut having a proximal end and a distal end, wherein the distal end of the first strut includes an abutment having a first engagement portion, and wherein at least the first struts move independently of one another;
    a left and a right inferior bone anchor configured for attachment to the inferior vertebra, each inferior bone anchor comprising a second strut having a proximal end and a distal end, wherein the distal end of the second strut includes a second engagement portion configured to slidably engage with the first engagement portion of the abutment of the distal end of the superior bone anchor, and wherein the configuration of the second engagement portion relative to the first engagement portion limits relative motion between the first and the second strut; and
    a tension band extending between the superior bone anchor and the inferior bone anchor.

2. The system of claim 1, wherein the distal end of at least one of the first struts has a convex surface and the distal end of at least one of the second struts has a concave surface configured to receive the convex surface of at least one of the first struts.

3. The system of claim 2, wherein the convex and concave surfaces are reciprocally rounded.

4. The system of claim 2, wherein the convex and concave surfaces are reciprocally angular.

5. The system of claim 1, wherein the distal end of at least one of the first struts has a concave surface and the distal end of at least one of the second struts has a convex surface configured to receive the concave surface of at least one of the first struts.

6. The system of claim 1, wherein the tension band is positioned posteriorly to the struts.

7. The system of claim 1, wherein the tension band is positioned laterally of the struts.

8. The system of claim 1, wherein the superior bone anchor is configured for attachment at the pedicle of the superior vertebra and the inferior bone anchor is configured for attachment to the pedicle of the inferior vertebra.

9. The system of claim 1, wherein the system is configured for implantation without the removal of any portion of the spinal motion segment.

10. A system for stabilizing at least one spinal motion segment comprising a superior vertebra and an inferior vertebra, the system comprising:
a left and a right superior bone anchor configured to couple to the superior vertebra, each superior bone anchor comprising a first strut having a proximal end and a distal end, wherein the distal end of the first strut includes an abutment having a first engagement portion, and wherein at least the first struts move independently of one another;
a left and a right inferior bone anchor configured for attachment to the inferior vertebra, each inferior bone anchor comprising a second strut having a proximal end and a distal end, wherein the distal end of the second strut includes a second engagement portion configured to slidably engage with the first engagement portion of the abutment of the distal end of the superior bone anchor, and wherein the configuration of the second engagement portion relative to the first engagement portion limits relative motion between the first and the second strut; and
a tension band extending between the superior bone anchor and the inferior bone anchor, wherein the tension band is positioned posteriorly to the struts.

11. The system of claim 10, wherein the distal end of at least one of the first struts has a convex surface and the distal end of at least one of the second struts has a concave surface configured to receive the convex surface of at least one of the first struts.

12. The system of claim 10, wherein the distal end of at least one of the first struts has a concave surface and the distal end of at least one of the second struts has a convex surface configured to receive the concave surface of at least one of the first struts.

13. The system of claim 10, wherein the superior bone anchor is configured for attachment at the pedicle of the superior vertebra and the inferior bone anchor is configured for attachment to the pedicle of the inferior vertebra.

14. The system of claim 10, wherein the system is configured for implantation without the removal of any portion of the spinal motion segment.

15. A method for stabilizing at least one spinal motion segment comprising a superior vertebra and an inferior vertebra, the method comprising:
attaching a superior bone anchor to the superior vertebra, the superior bone anchor comprising a first strut having a proximal end and a distal end, wherein the distal end of the first strut includes an abutment;
attaching an inferior bone anchor to the inferior vertebra, the inferior bone anchor comprising a second strut comprising an engagement portion slidably engaged with the abutment of the distal end of the first strut of the superior bone anchor;
limiting motion between the superior and inferior bone anchors by the configuration of the abutment relative to the engagement portion, wherein the abutment and the engagement portion are in an unconstrained configuration to allow flexion, extension, axial rotation and lateral bending motions while limiting anterior and lateral translation between the superior and inferior vertebrae;
allowing at least the first strut to move independently of one another; and
extending a tension device substantially parallel to the strut between the superior bone anchor and the inferior bone anchor.

16. The method of claim 15, wherein attachment of each of the components to the vertebrae comprises using a pedicle screw.

17. The method of claim 15, wherein the components are attached without resecting any portion of the spinal motion segment.

18. The method of claim 15, wherein the tension device is a ligament.

19. The method of claim 15, further comprising guiding the distal end of the strut through a u-shaped abutment.

20. The method of claim 15, wherein limiting transverse motion between the superior bone anchor and the inferior bone anchor includes a slot shaped abutment configuration.

* * * * *